US012665059B2

(12) United States Patent
Boucher et al.

(10) Patent No.: US 12,665,059 B2
(45) Date of Patent: Jun. 23, 2026

(54) DEVICES, METHODS, AND SYSTEMS FOR ACQUIRING MEDICAL DIAGNOSTIC INFORMATION AND PROVISION OF TELEHEALTH SERVICES

(71) Applicant: Zipline Health, Inc., San Francisco, CA (US)

(72) Inventors: Ryan Boucher, San Francisco, CA (US); Lionel Nelson, Los Altos Hills, CA (US)

(73) Assignee: Zipline Health, Inc, Queensbury, NY (US)

( * ) Notice: Subject to any disclaimer, the term of this patent is extended or adjusted under 35 U.S.C. 154(b) by 0 days.

(21) Appl. No.: 17/336,133

(22) Filed: Jun. 1, 2021

(65) Prior Publication Data

US 2021/0358582 A1     Nov. 18, 2021

Related U.S. Application Data

(63) Continuation of application No. 15/573,432, filed as application No. PCT/US2016/032223 on May 12, 2016, now abandoned.

(Continued)

(51) Int. Cl.
*G16H 10/60* (2018.01)
*A61B 1/00* (2006.01)
(Continued)

(52) U.S. Cl.
CPC .............. *G16H 10/60* (2018.01); *A61B 1/00* (2013.01); *A61B 1/00016* (2013.01); *A61B 1/04* (2013.01);
(Continued)

(58) Field of Classification Search
None
See application file for complete search history.

(56) References Cited

U.S. PATENT DOCUMENTS 5,489,256 A     2/1996  Adair
5,658,235 A     8/1997  Priest et al.
              (Continued)

FOREIGN PATENT DOCUMENTS

FR         2928823 B1     12/2011
JP     H10-258023 A       9/1998
              (Continued)

OTHER PUBLICATIONS

Japan Patent Office, Office Action, JP Patent Application No. 2018-511350, Jun. 23, 2020, five pages.
(Continued)

*Primary Examiner* — Shirley X Jian
(74) *Attorney, Agent, or Firm* — John D. Lanza; Foley Hoag LLP

(57) ABSTRACT

The invention relates generally to various systems, tools and methods for acquiring diagnostic information, including medical information, for a user, transmitting the information to a remote location, assessing the information, and transmitting resulting diagnosis and treatment information to the user and/or a third party for subsequent action. The present invention provides consumer and user-friendly telemedicine systems and procedures which enable health services and/or diagnosis to be provided at a distance remotely.

15 Claims, 61 Drawing Sheets

Related U.S. Application Data

(60) Provisional application No. 62/160,468, filed on May 12, 2015.

(51) Int. Cl.

| | |
|---|---|
| *A61B 1/04* | (2006.01) |
| *A61B 1/06* | (2006.01) |
| *A61B 1/07* | (2006.01) |
| *A61B 1/227* | (2006.01) |
| *A61B 1/233* | (2006.01) |
| *A61B 1/24* | (2006.01) |
| *A61B 1/273* | (2006.01) |
| *A61B 5/00* | (2006.01) |
| *A61B 5/05* | (2021.01) |
| *A61B 7/00* | (2006.01) |
| *A61B 7/04* | (2006.01) |
| *A61B 90/00* | (2016.01) |
| *G16H 30/20* | (2018.01) |
| *G16H 40/67* | (2018.01) |
| *G16H 50/20* | (2018.01) |
| *G16H 80/00* | (2018.01) |

(52) U.S. Cl.
CPC .............. *A61B 1/0669* (2013.01); *A61B 1/07* (2013.01); *A61B 1/227* (2013.01); *A61B 1/233* (2013.01); *A61B 1/24* (2013.01); *A61B 1/273* (2013.01); *A61B 5/0022* (2013.01); *A61B 5/05* (2013.01); *A61B 5/6817* (2013.01); *A61B 5/682* (2013.01); *A61B 5/684* (2013.01); *A61B 7/003* (2013.01); *A61B 7/04* (2013.01); *A61B 90/361* (2016.02); *G16H 30/20* (2018.01); *G16H 40/67* (2018.01); *G16H 50/20* (2018.01); *G16H 80/00* (2018.01); *A61B 2090/036* (2016.02)

(56) References Cited

U.S. PATENT DOCUMENTS

| | | | |
|---|---|---|---|
| 5,701,904 A | 12/1997 | Simmons et al. | |
| 5,830,121 A | 11/1998 | Enomoto et al. | |
| 5,967,969 A | 10/1999 | Enomoto et al. | |
| 5,989,186 A | 11/1999 | Alatriste | |
| 6,319,199 B1 | 11/2001 | Sheehan et al. | |
| 6,450,970 B1 | 9/2002 | Mahler et al. | |
| 7,025,061 B2 | 4/2006 | Haussmann | |
| 7,399,275 B2 | 7/2008 | Goldfain et al. | |
| 7,481,817 B2 | 1/2009 | Sauer | |
| 7,549,424 B2 | 6/2009 | Desai | |
| 7,946,981 B1 | 5/2011 | Cubb | |
| 8,114,105 B2 | 2/2012 | Sauer | |
| 8,602,971 B2 | 12/2013 | Farr | |
| 9,498,112 B1 | 11/2016 | Stewart et al. | |
| 10,973,410 B2 * | 4/2021 | Marsh .................. | A61B 5/0205 |
| 11,298,013 B2 * | 4/2022 | Gilad-Gilor ....... | A61B 1/00142 |
| 12,390,161 B2 * | 8/2025 | Boucher .............. | A61B 5/6844 |
| 2002/0022763 A1 | 2/2002 | Sano et al. | |
| 2002/0038076 A1 | 3/2002 | Sheehan et al. | |
| 2002/0118279 A1 | 8/2002 | Spoonhower et al. | |
| 2003/0016284 A1 | 1/2003 | Squilla et al. | |
| 2003/0100819 A1 | 5/2003 | Newman et al. | |
| 2004/0073455 A1 | 4/2004 | McConnochie et al. | |
| 2004/0249246 A1 | 12/2004 | Campos | |
| 2005/0038317 A1 | 2/2005 | Ratnakar | |
| 2005/0200707 A1 | 9/2005 | Yogesan et al. | |
| 2005/0272975 A1 | 12/2005 | McWeeney et al. | |
| 2006/0149129 A1 | 7/2006 | Watts et al. | |
| 2009/0088611 A1 * | 4/2009 | Buschmann ......... | A61B 5/6817 |
| | | | 600/301 |
| 2009/0198111 A1 | 8/2009 | Nearman et al. | |
| 2009/0203986 A1 | 8/2009 | Winnick | |
| 2010/0191125 A1 | 7/2010 | Foged et al. | |
| 2010/0249513 A1 | 9/2010 | Tydlaska | |
| 2010/0261968 A1 | 10/2010 | Nearman et al. | |
| 2010/0305409 A1 | 12/2010 | Chang | |
| 2011/0224493 A1 | 9/2011 | Oyadiran et al. | |
| 2011/0257481 A1 | 10/2011 | Ogawa et al. | |
| 2012/0253166 A1 | 10/2012 | Ahn et al. | |
| 2013/0014750 A1 | 1/2013 | Etesham | |
| 2013/0027516 A1 * | 1/2013 | Hart ..................... | A61B 5/0071 |
| | | | 348/45 |
| 2013/0035607 A1 * | 2/2013 | Wada ................... | A61B 5/6817 |
| | | | 600/549 |
| 2013/0331779 A1 * | 12/2013 | Dhanasingh ........ | A61M 31/002 |
| | | | 604/93.01 |
| 2014/0073880 A1 | 3/2014 | Boucher et al. | |
| 2014/0138179 A1 | 5/2014 | Burton | |
| 2014/0152970 A1 * | 6/2014 | Wada ................... | A61B 5/1075 |
| | | | 356/3 |
| 2015/0142029 A1 | 5/2015 | Fahn et al. | |
| 2015/0215693 A1 | 7/2015 | Sandanger | |
| 2015/0351607 A1 | 12/2015 | Ruppersberg et al. | |
| 2015/0351688 A1 | 12/2015 | Just et al. | |
| 2017/0020382 A1 | 1/2017 | Sezan et al. | |
| 2017/0325667 A1 | 11/2017 | Babarro | |
| 2018/0000336 A1 * | 1/2018 | Gilad-Gilor .......... | A61B 1/005 |
| 2018/0353073 A1 | 12/2018 | Boucher et al. | |
| 2018/0360295 A1 | 12/2018 | Boucher et al. | |
| 2021/0353230 A1 * | 11/2021 | Boucher .............. | A61B 5/6844 |

FOREIGN PATENT DOCUMENTS

| | | | | |
|---|---|---|---|---|
| JP | H11-113841 A | 4/1999 | | |
| JP | 2002-132958 A | 5/2002 | | |
| JP | 2007-500541 A | 1/2007 | | |
| KR | 2002-0009302 A | 2/2002 | | |
| WO | WO 02/056756 A2 | 7/2002 | | |
| WO | WO 2005/011484 A1 | 2/2005 | | |
| WO | WO-2009055347 A2 * | 4/2009 | .......... | H04R 25/656 |
| WO | WO-2010105649 A1 * | 9/2010 | ............. | A61B 1/008 |
| WO | WO 2012/058641 A2 | 5/2012 | | |
| WO | WO 2014/004905 A1 | 1/2014 | | |
| WO | WO 2014/117954 A2 | 8/2014 | | |
| WO | WO 2016/183389 A9 | 1/2017 | | |

OTHER PUBLICATIONS

Japan Patent Office, Office Action, JP Patent Application No. 2018-511350, Jan. 12, 2021, six pages.

PCT International Search Report and Written Opinion, PCT Application No. PCT/US2016/032223, Oct. 7, 2016, nine pages.

PCT International Search Report and Written Opinion, PCT Application No. PCT/US2018/036715, Aug. 27, 2018, 13 pages.

Canadian Intellectual Property Office, Office Action, CA Patent Application No. 2,877,717, Apr. 5, 2018, five pages.

European Patent Office, Extended European Search Report and Opinion, EP Patent Application No. 20179958.2, Jan. 22, 2021, 13 pages.

European Patent Office, Extended European Search Report and Opinion, EP Patent Application No. 13808431.4, Oct. 7, 2016, 14 pages.

Japan Patent Office, Office Action, JP Patent Application No. 2018-072800, Jul. 2, 2019, ten pages.

PCT International Preliminary Report on Patentability, PCT Application No. PCT/US2013/048316, Dec. 31, 2014, six pages.

PCT International Search Report, PCT Application No. PCT/US2013/048316, Oct. 24, 2013, three pages.

PCT Written Opinion, PCT Application No. PCT/US2013/048316, Oct. 24, 2013, six pages.

United States Office Action, U.S. Appl. No. 13/929,591, filed Jul. 18, 2017, 23 pages.

United States Office Action, U.S. Appl. No. 15/920,208, filed Jul. 23, 2020, 14 pages.

United States Office Action, U.S. Appl. No. 15/920,208, filed Nov. 15, 2019, 15 pages.

United States Office Action, U.S. Appl. No. 15/573,432, filed Mar. 1, 2021, 28 pages.

(56)  References Cited

OTHER PUBLICATIONS

United States Office Action, U.S. Appl. No. 15/573,432, filed Aug. 5, 2020, 26 pages.
United States Office Action, U.S. Appl. No. 15/573,432, filed Dec. 31, 2019, 16 pages.
United States Office Action, U.S. Appl. No. 15/573,432, filed Apr. 24, 2019, 17 pages.
Japan Patent Office, Office Action, Japanese Patent Application No. 2021-098126, Aug. 2, 2022, 8 pages.

* cited by examiner

10
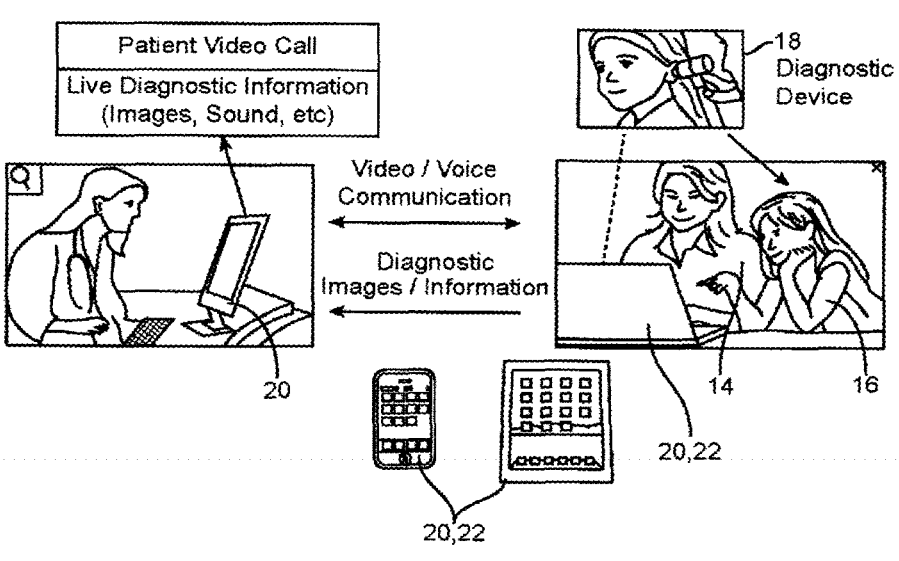
FIG. 1
10
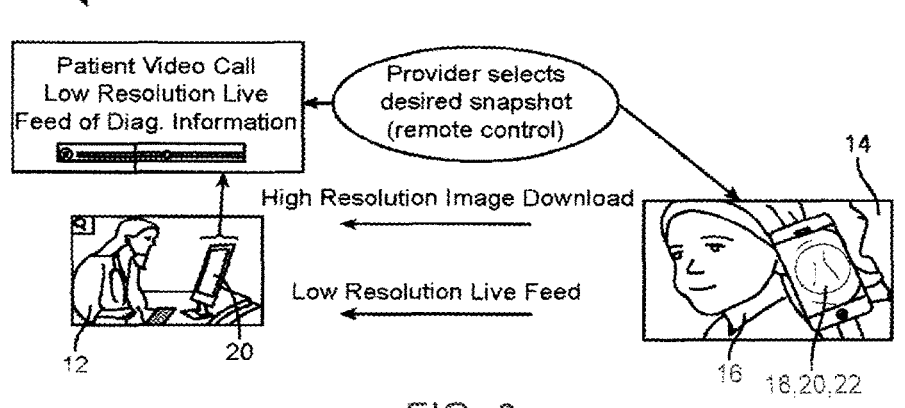
FIG. 2

EXAMPLES OF USER SYSTEMS AND DEVICES (3 different examples)

Horizontal Section, LT Ear, View of
Superior Half – from Gray's Anatomy

Trace of Above Section –
Key Anatomy

EAR IMAGING AND DEVICES:

Strap
28
26,34
Microphones 26,34
Microphone          28
Shirt / Vest

22
To Diagnostic
Processor 24,26
Lens +
Video
Chip

28
Oral Device w/
Digital Imaging          FIG. 34

To Diagnostic
Processor

26

24
28

Ear bud w/ Fibers or
Channel to Interface w/
Diagnostic Processor +
Video Chip

22
Device w/
Video Chip +
Electronics

24

28

Oral Device w / Fiber Optics
or Channel to Interface w /
Diagnostic Procesor and Video Chip

PERTINENT ANATOMY

Ear Canal Shape

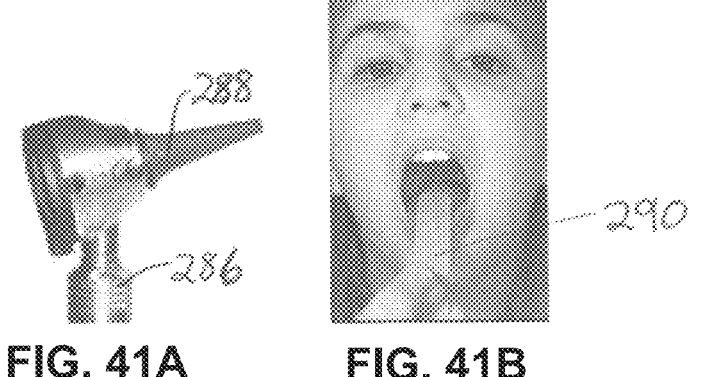
FIG. 41A          FIG. 41B
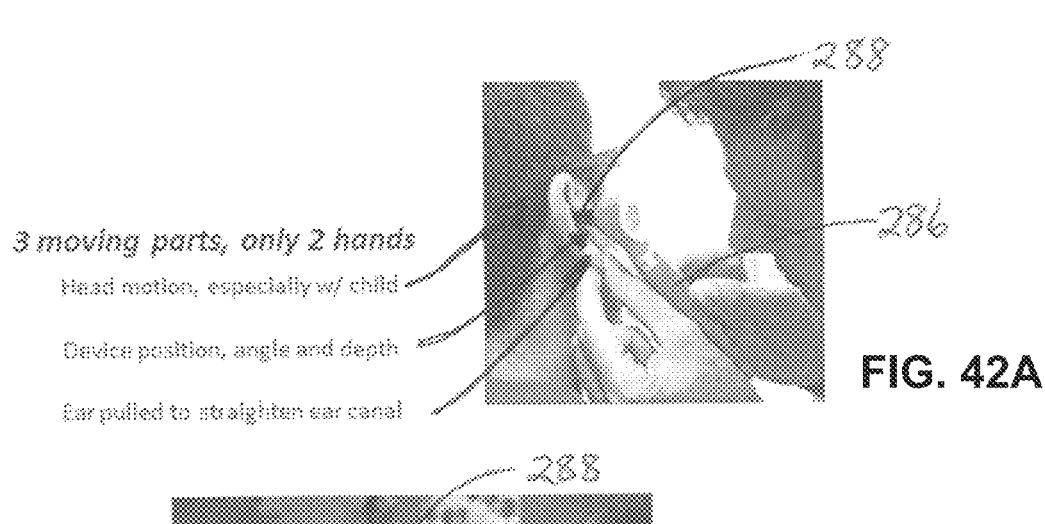
*3 moving parts, only 2 hands*
Head motion, especially w/ child
Device position, angle and depth
Ear pulled to straighten ear canal
FIG. 42A
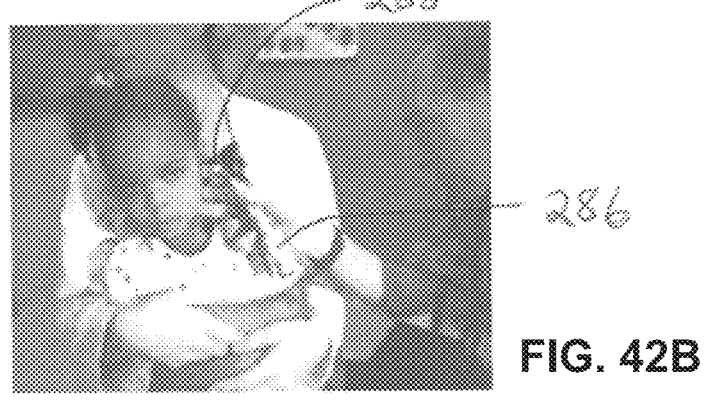
FIG. 42B

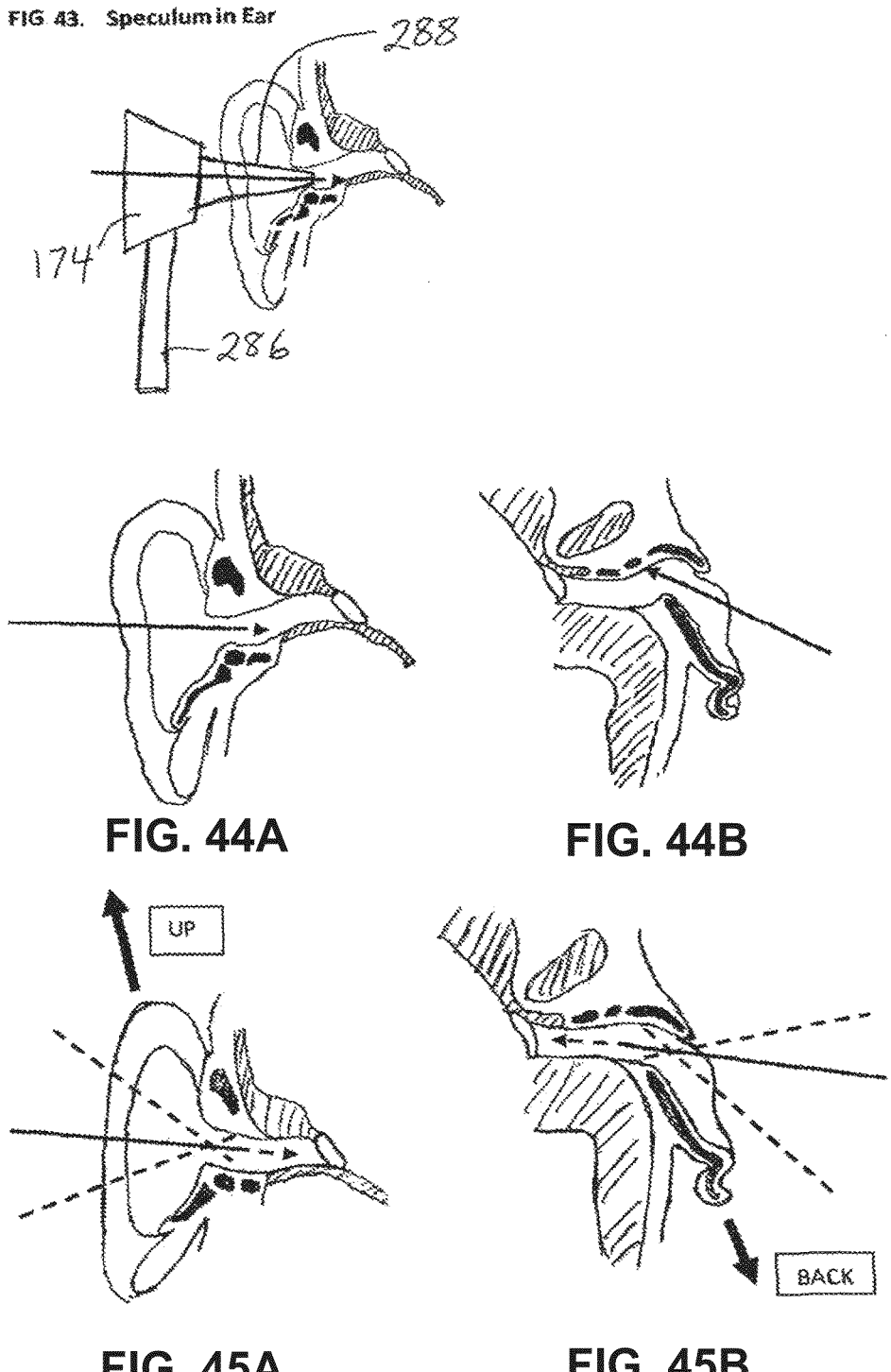
FIG 43.  Speculum in Ear
FIG. 44A          FIG. 44B
FIG. 45A          FIG. 45B

FIG. 46.   Looking in mouth and throat.
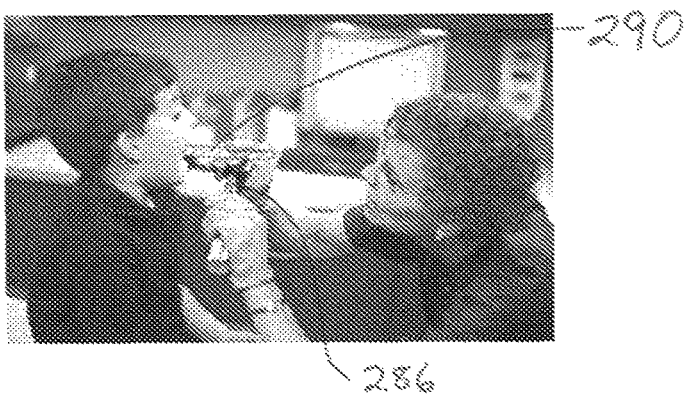
FIG. 47.   Difficulty viewing throat – jaw and tongue position
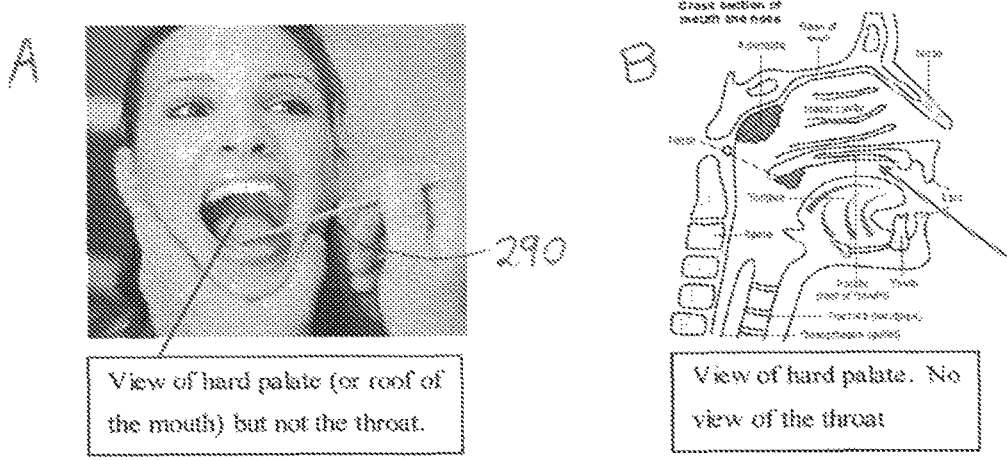
FIG. 48.   Tongue depressed with view of throat
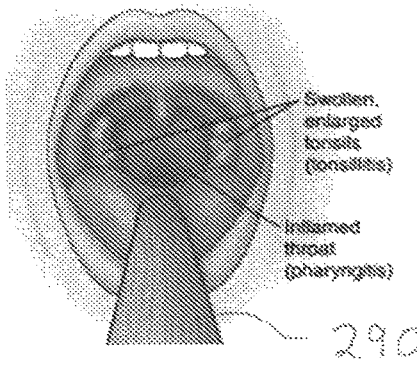

FIG. 49.   Exemplary New Ear Device and Advantages
* Familiar interface for parent and child,
  not an intimidating medical instrument
* Only 1 Moving Part, 2 Hands
     (moves with the ear and head)
* Self-aligning with ear drum
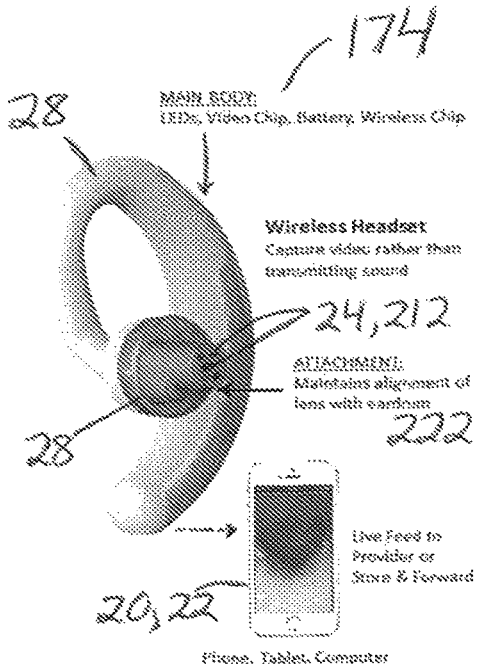

HeadFront: Perpendicular to Head in frontal, or coronal, plane

EarFront: Perpendicular to Ear in frontal, or coronal, plane

EarFront

HeadFront

EarHorz: Perpendicular to Ear in
horizontal, or transverse, plane

HeadHorz: Perpendicular to Head in
horizontal, or transverse, plane

EarHorz          HeadHorz

PREFERRED POSITIONS AND ANGLES
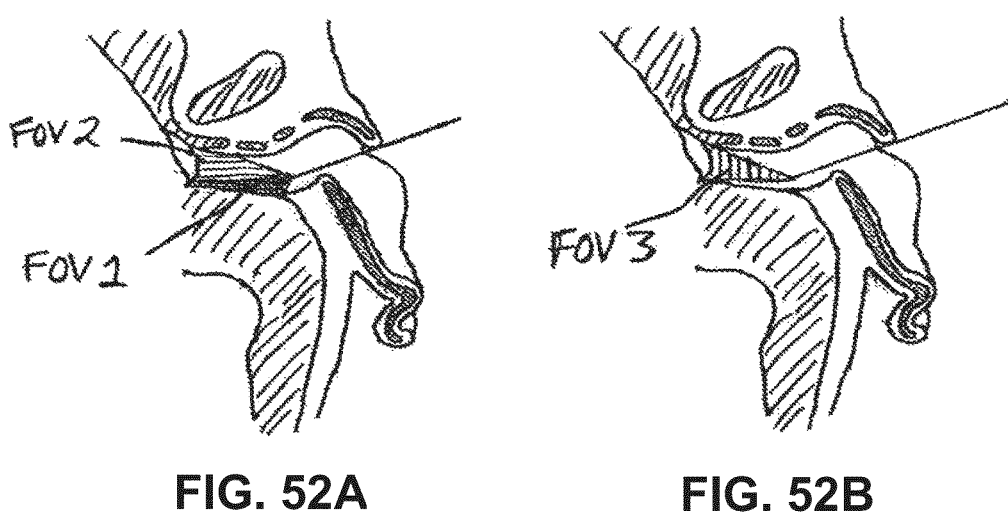
FIG. 52A             FIG. 52B
FIG. 53.   Preferred Positions and Angles – Horizontal Section (Top Section View)
Horizontal Section of Ear Canal (Top View)
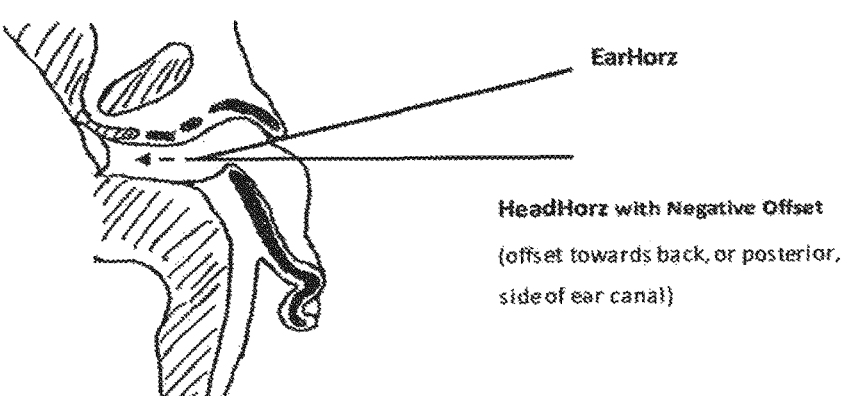
EarHorz
HeadHorz with Negative Offset
(offset towards back, or posterior,
side of ear canal)

FIG. 54.   Preferred Positions and Angles – Frontal Section (Front Section View)
Frontal Sections of Ear Canal
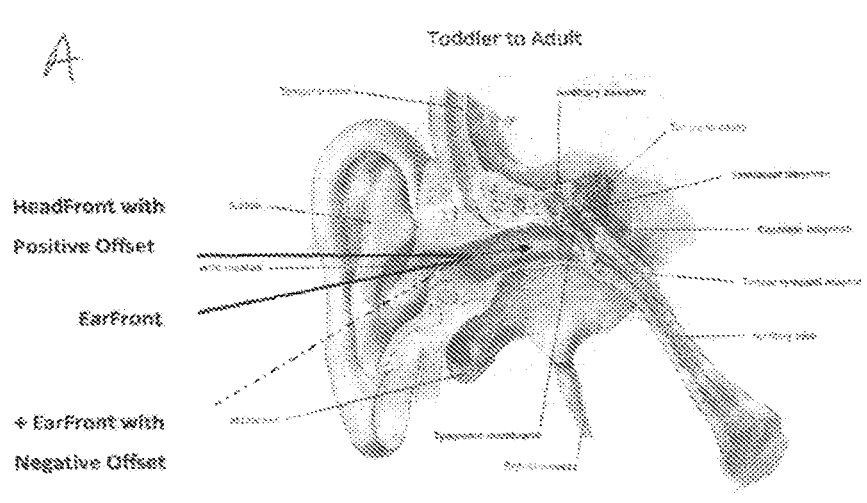
Toddler to Adult
HeadFront with
Positive Offset
EarFront
+ EarFront with
Negative Offset
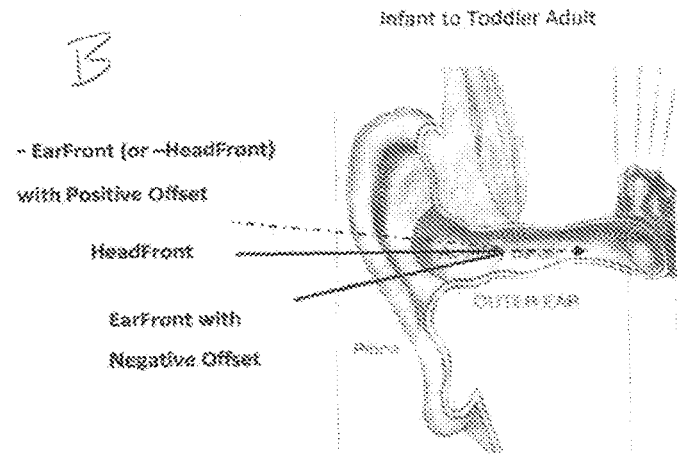
Infant to Toddler Adult
– EarFront (or –HeadFront)
with Positive Offset
HeadFront
EarFront with
Negative Offset Frontal Section: Imaging
Element in EarFront Position
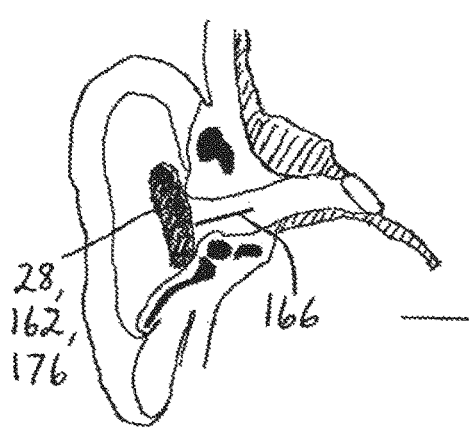
Horizontal Section: Imaging
Element in EarFront Position
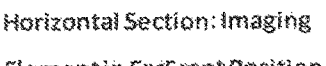
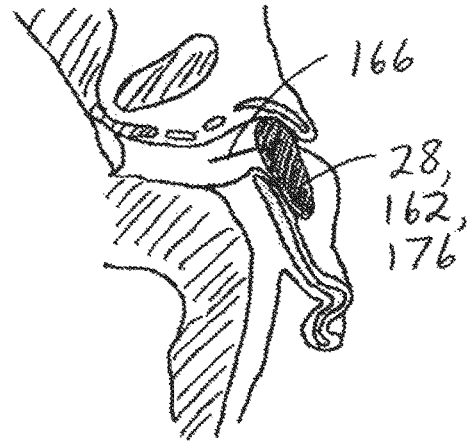
FIG. 55A
FIG. 55B
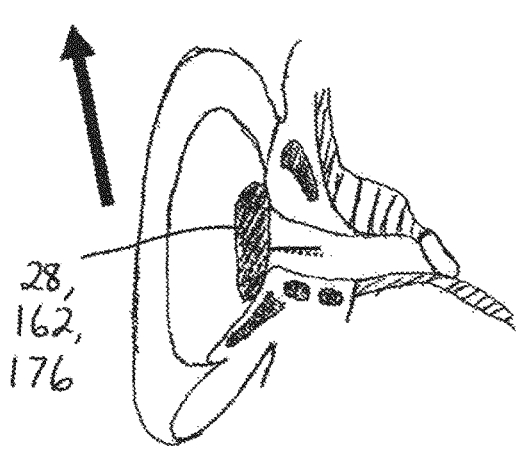
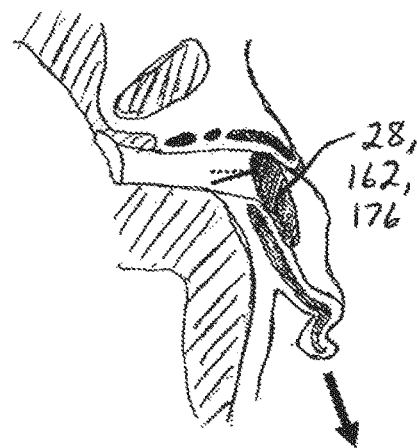
FIG. 56A
FIG. 56B

FIG. 58.   Over the Ear
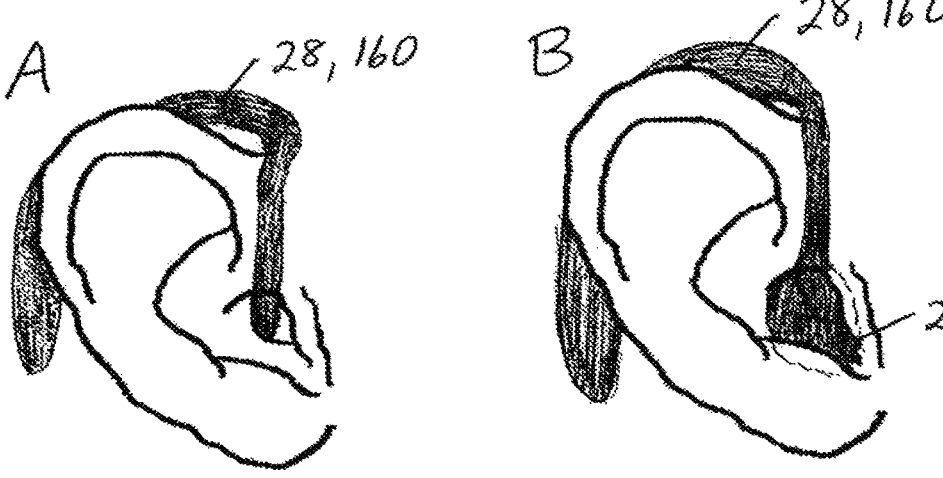
FIG. 59.   Cheek, Head, Neck, or Ear
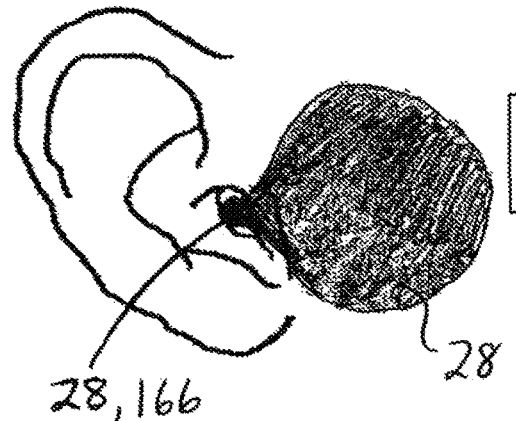
Allows support by the cheek, head, neck or ear depending on rotation.

FIG. 62A                    FIG. 62B

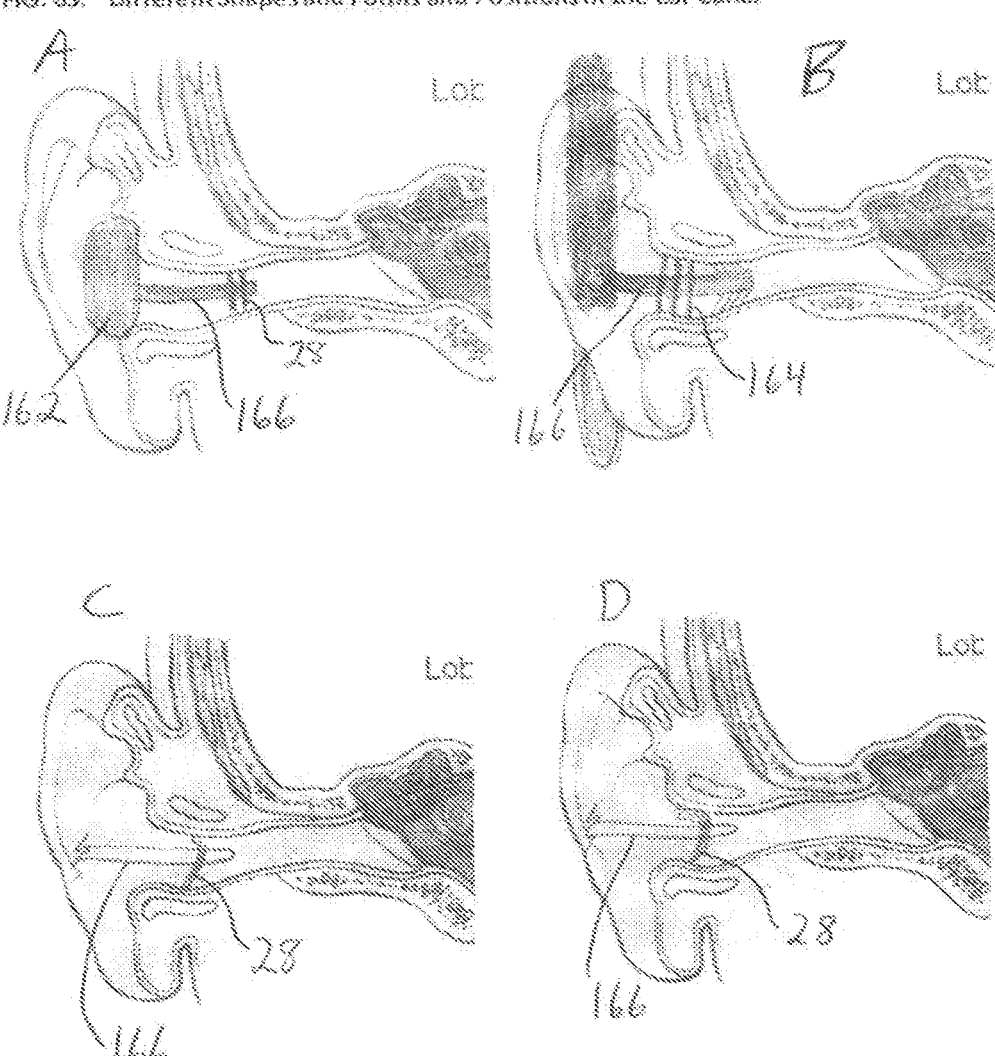
FIG. 63.   Different Shapes and Forms and Positions in the Ear Canal

FIG. 64. Near/In ear canal entrance and concha
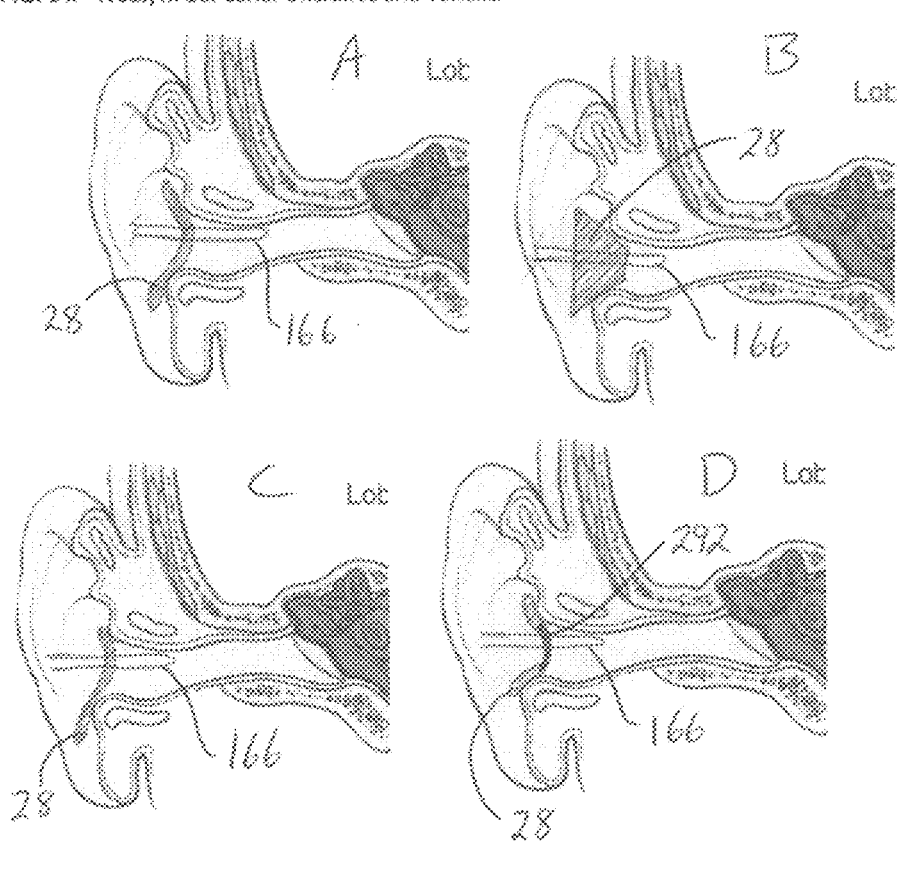
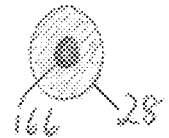
FIG. 65A
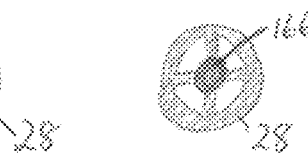
FIG. 65B
FIG. 65C
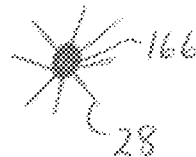
FIG. 65D
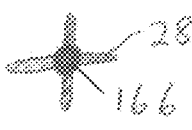
FIG. 65E

DIAGNOSTIC ELEMENTS – EXAMPLES OF POSITIONS AND ANGLES

FIG. 68A          FIG. 68B
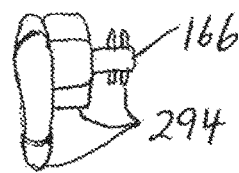
FIG. 69.   Hinged Extension Relative to Bud, moves in contact with tragus
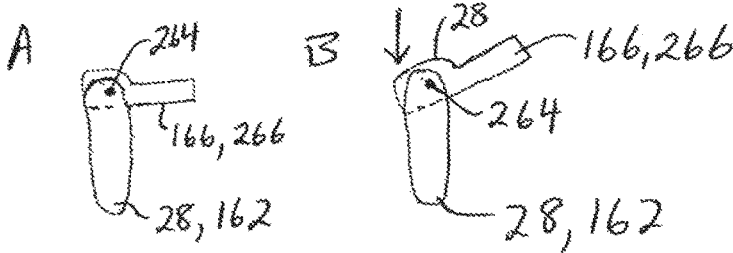
FIG. 70.   Flexible Joints
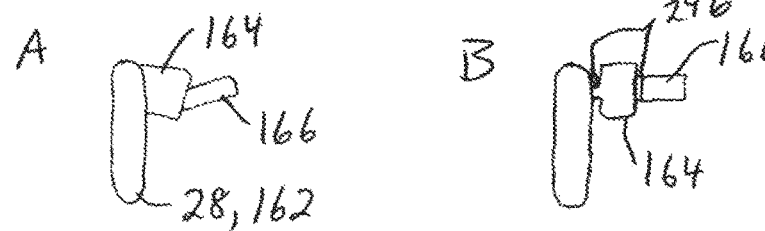
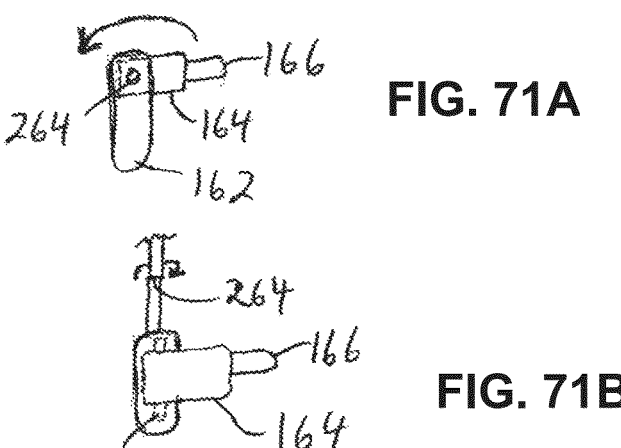
FIG. 71A
FIG. 71B

ANATOMICAL INTERFACES AND ACCESSING AND CAPTURING DIAGNOSTIC INFORMATION IN THE
ORAL CAVITY AND THROAT

FIG. 73. Anatomical Positions and Preferred Positions
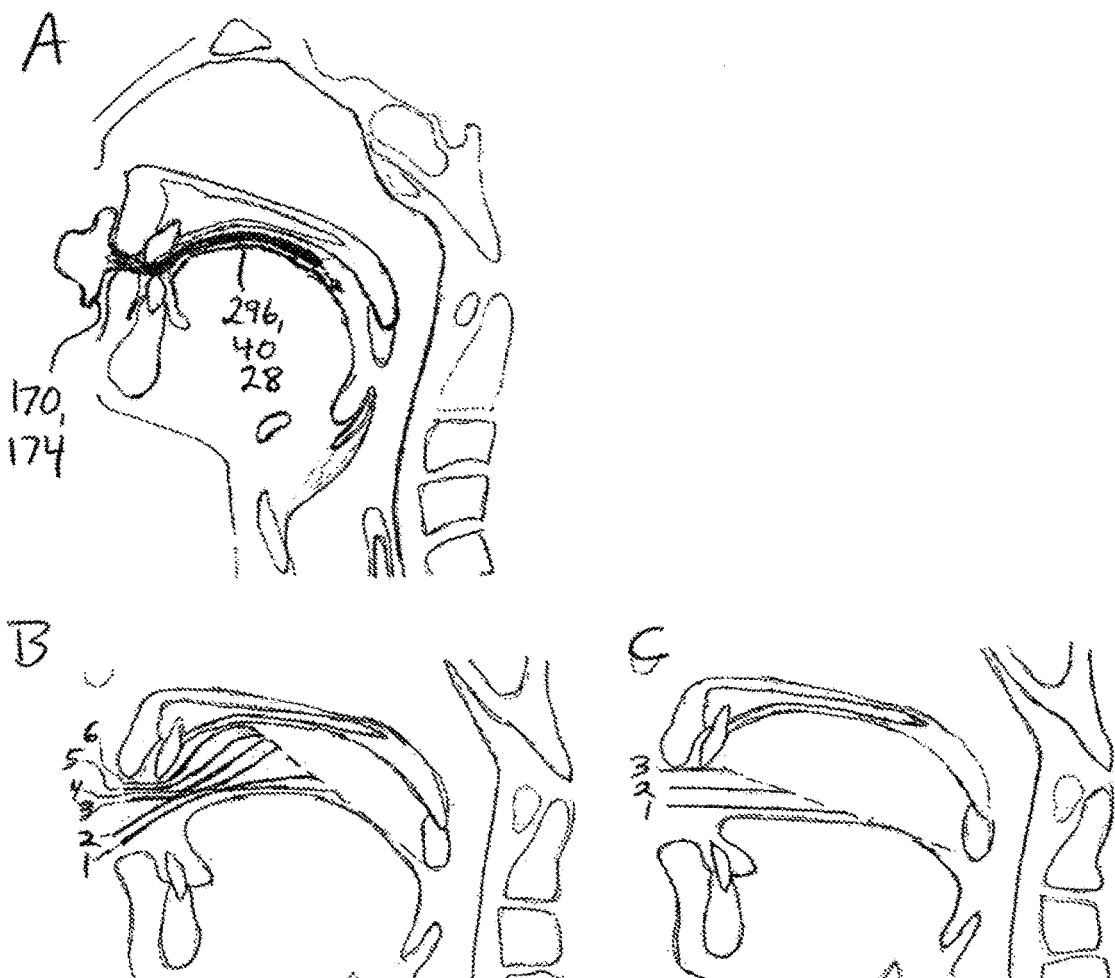

FIG. 74A          FIG. 74B
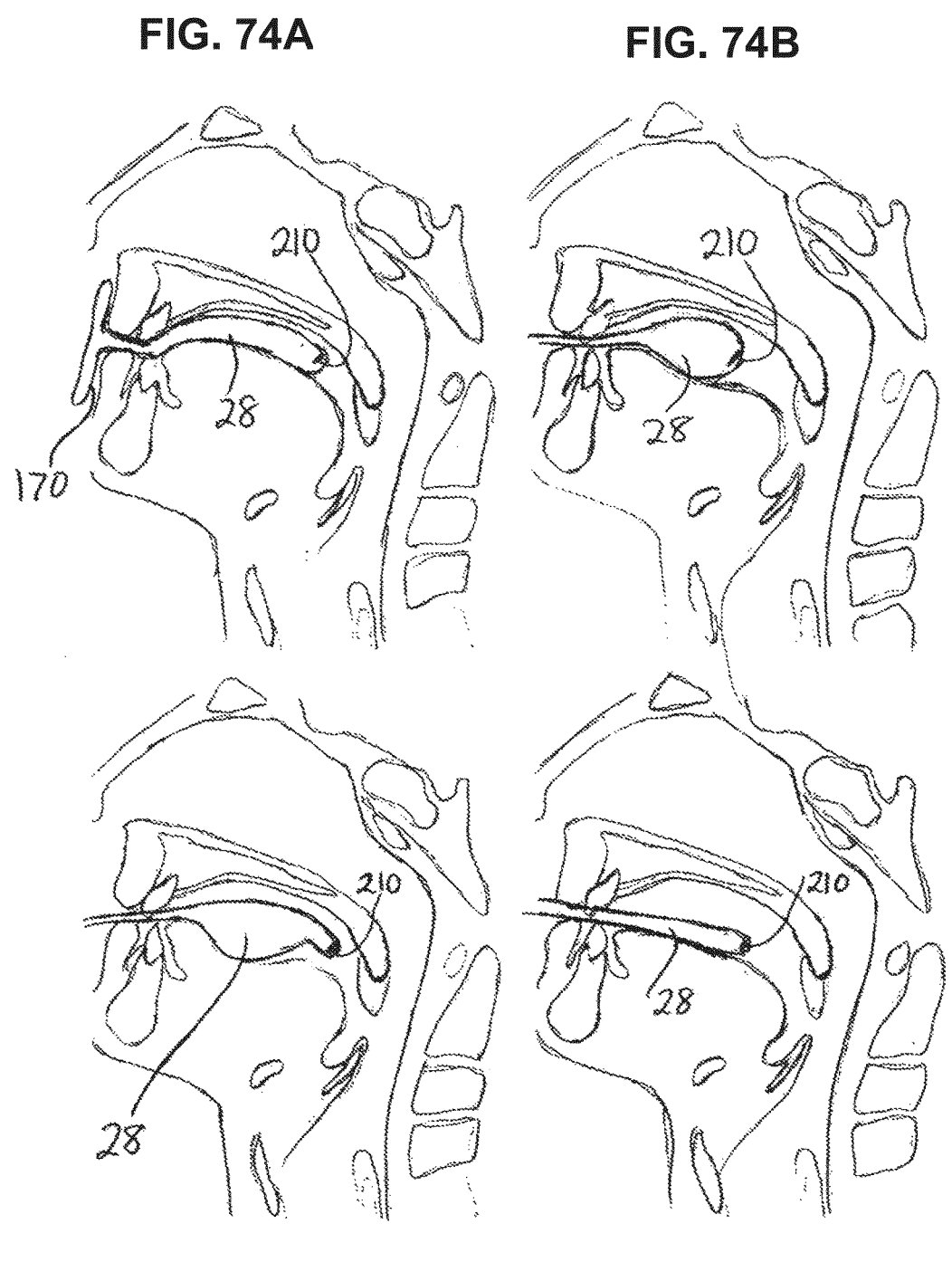
FIG. 74C          FIG. 74D

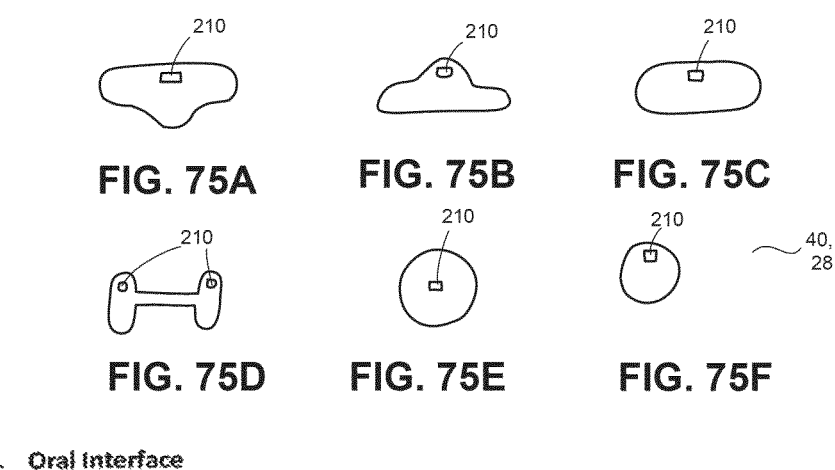
FIG. 75A          FIG. 75B          FIG. 75C
FIG. 75D          FIG. 75E          FIG. 75F
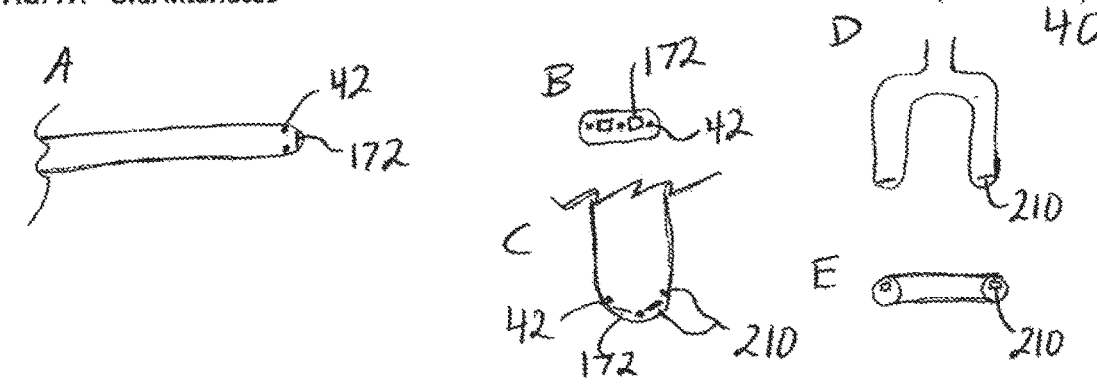
FIG. 76.   Oral Interface
FIG. 77.   Oral Interfaces FIG. 78.    Various Examples of Interfaces – Top Views – with examples of positions of elements

DIAGNOSTIC KITS, DEVICES AND ATTACHMENTS

CONFIGURATIONS OF COMPONENTS AND ELEMENTS IN EXEMPLARY DIAGNOSTIC DEVICES

FIG. 85.   Same device as previous figure or with capturing and light source at end of extension.  Fig. B
is a cross section of an attachment for imaging the ear.
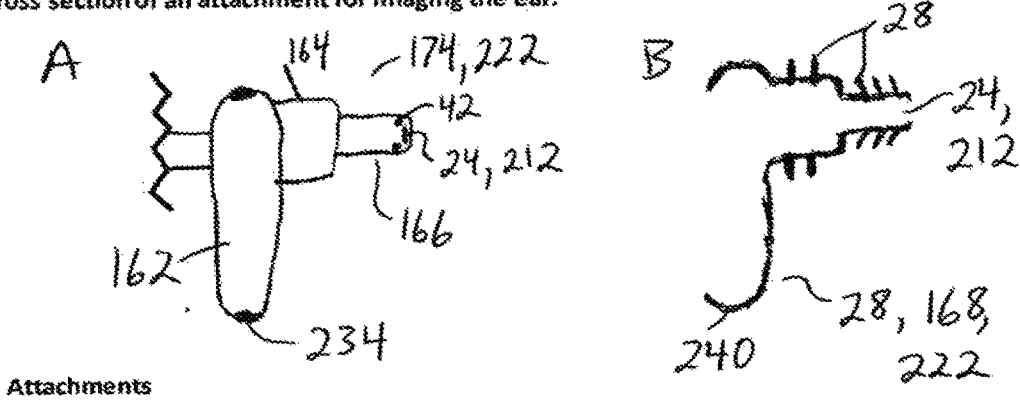
FIG. 86.   Attachments
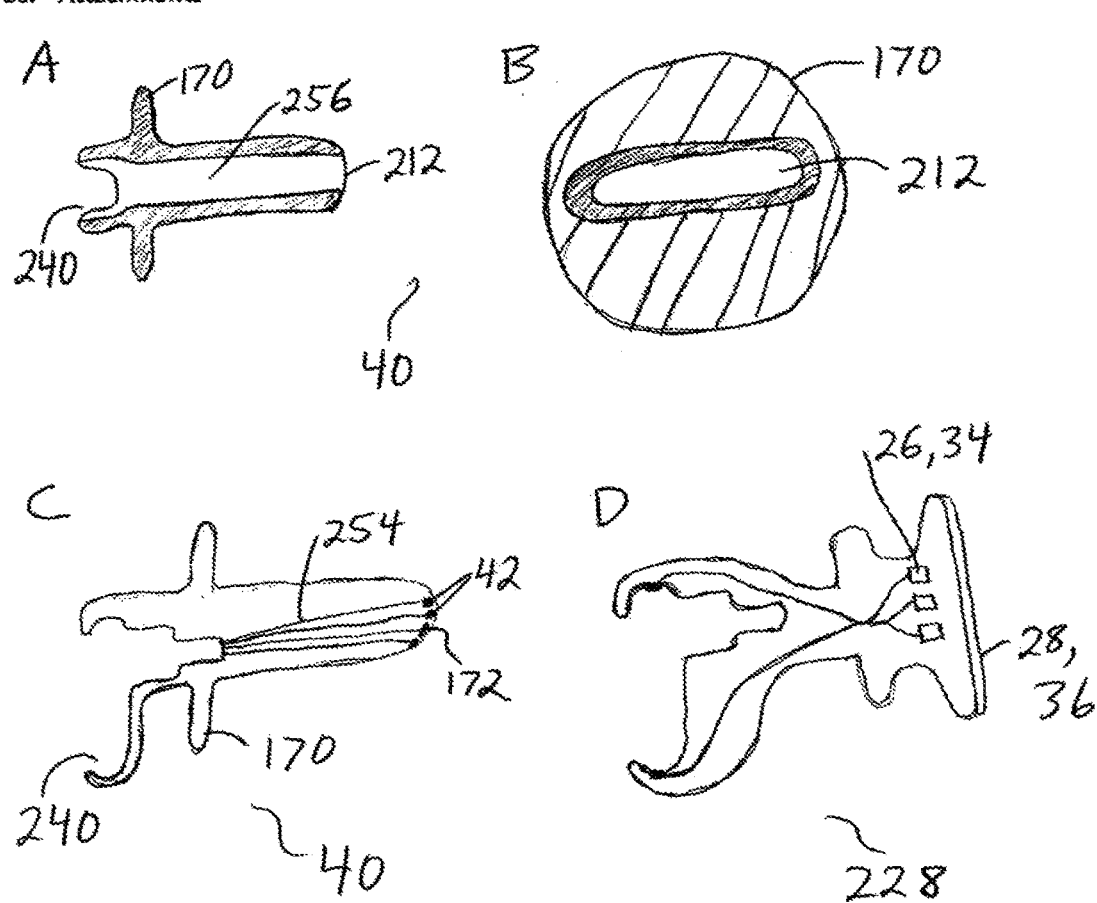

FIG. 87.  An alternative configuration of a main body and attachments.
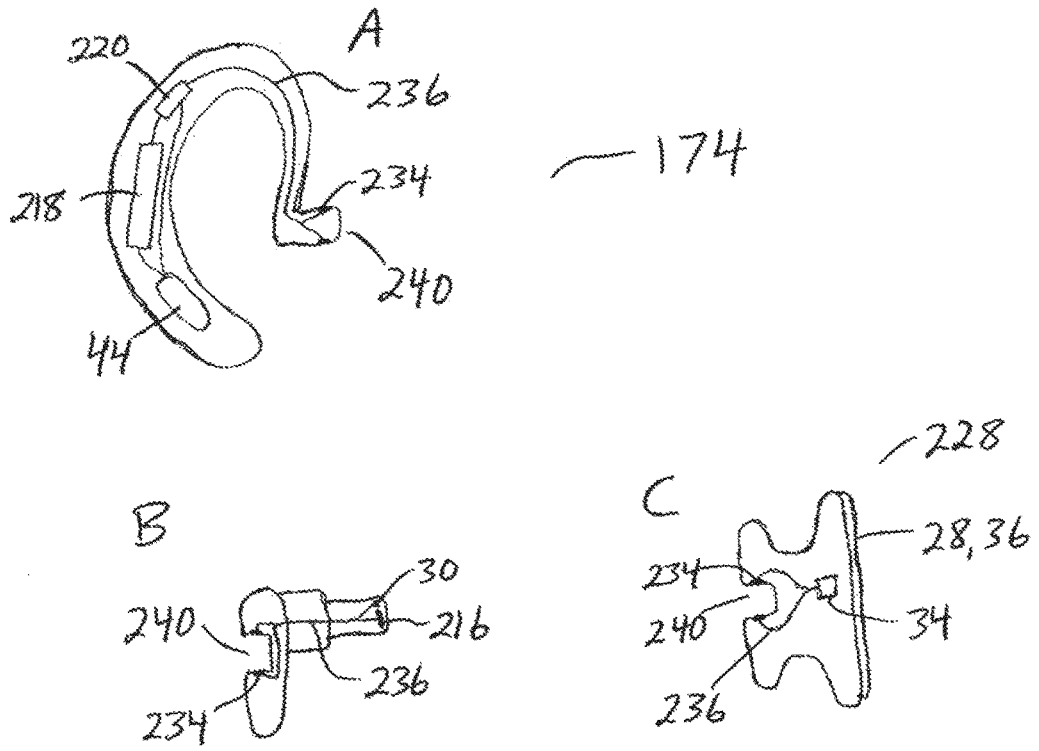
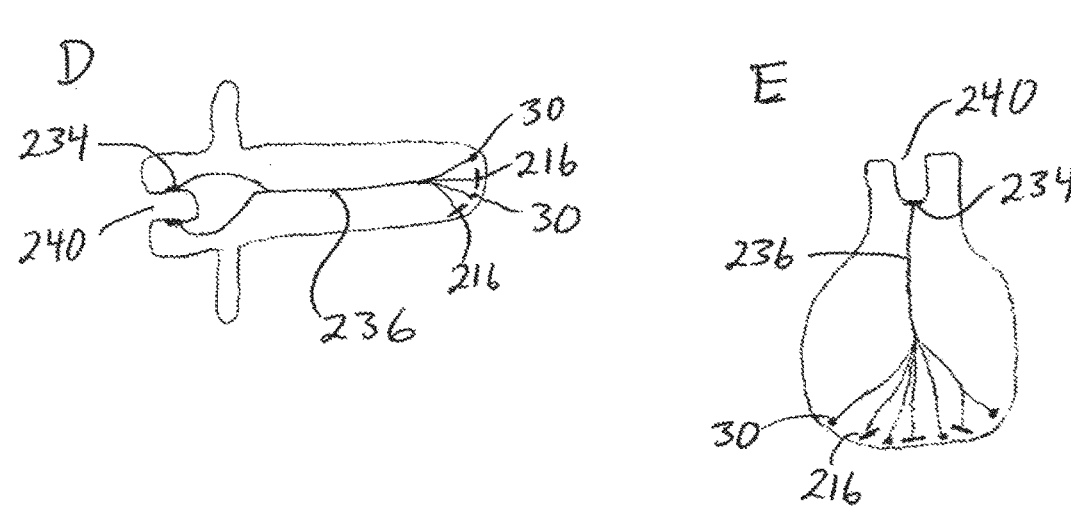

FIG. 88.   Another configuration of a main body and attachments.   This configuration shows capturing elements in both the main body and in the attachments.
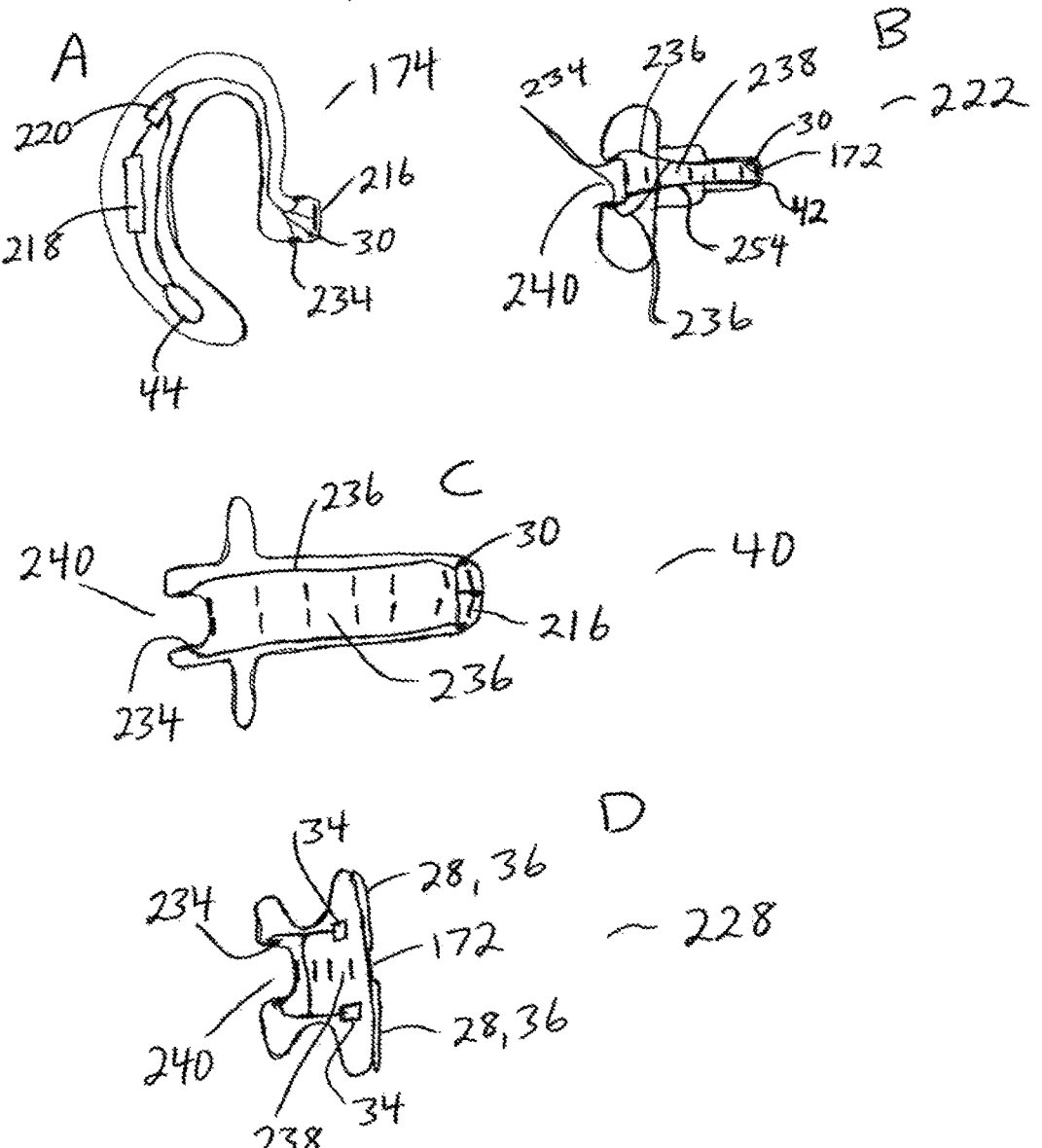

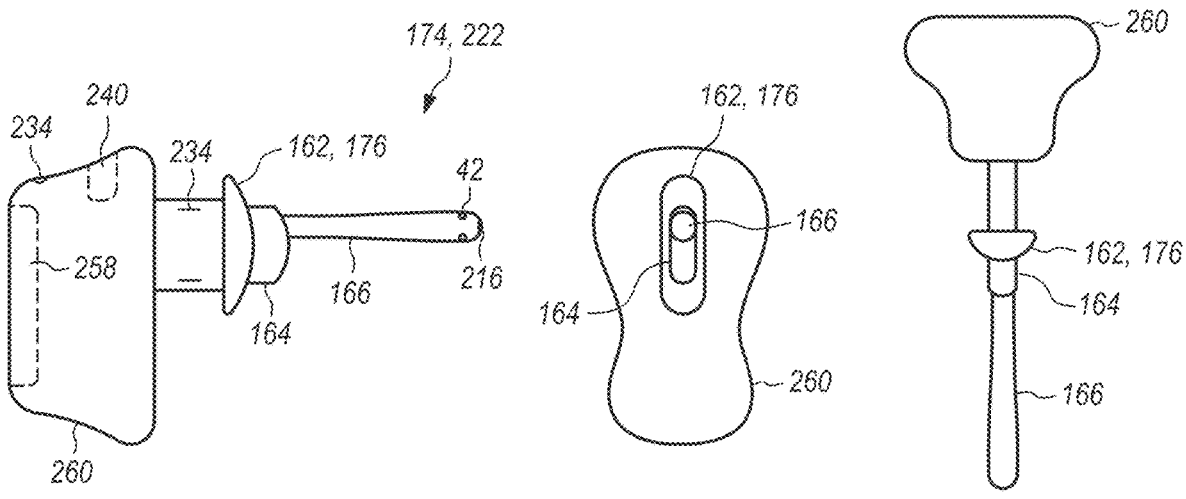
*FIG. 90A*　　　*FIG. 90B*　　　*FIG. 90C*
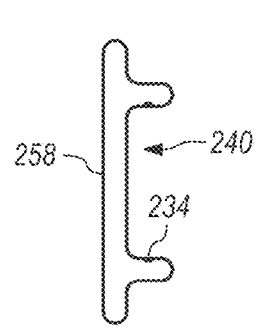
*FIG. 91A*
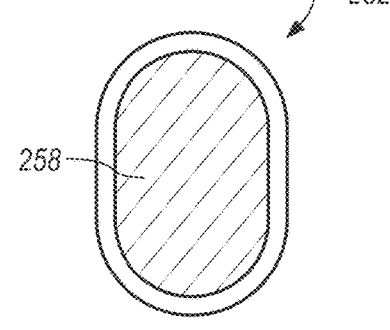
*FIG. 91B*
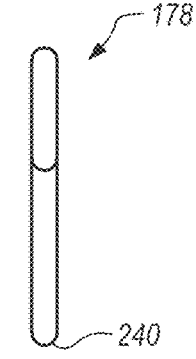
*FIG. 92A*
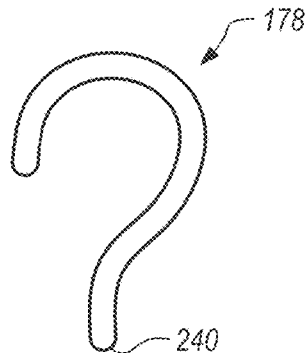
*FIG. 92B*

FIG. 93. Ear bud attachment – fits left and right
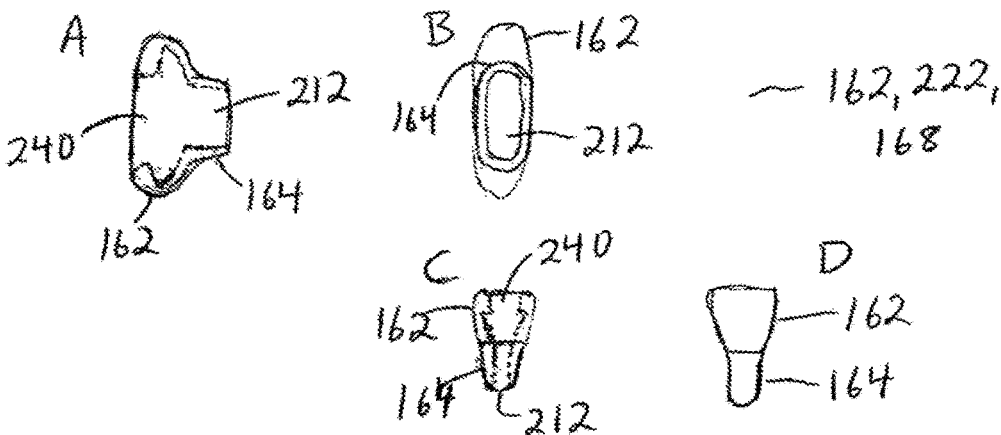
FIG. 94. Ear bud fits one ear – left or right.
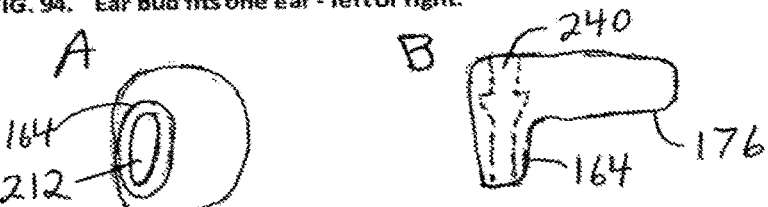
FIG. 95. Lighting configurations – tip view
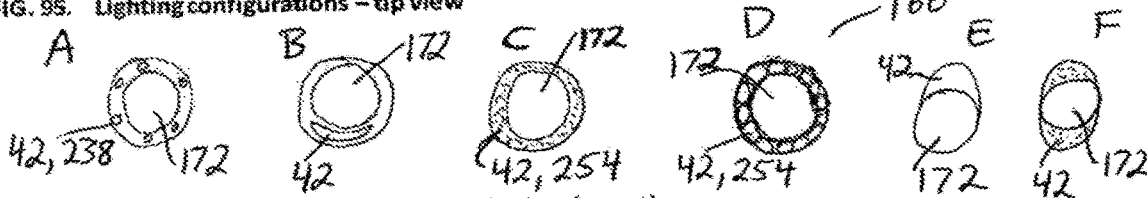
FIG. 96. Lighting and tip configurations – side view (x-sect)
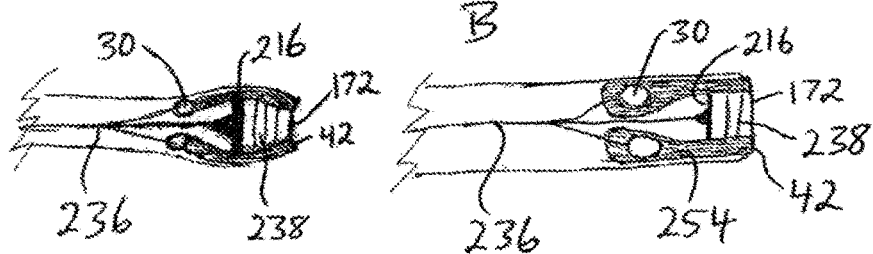

FIG. 97.   Bud with concha retainer that has flexibility to rotate around attachment section of main body
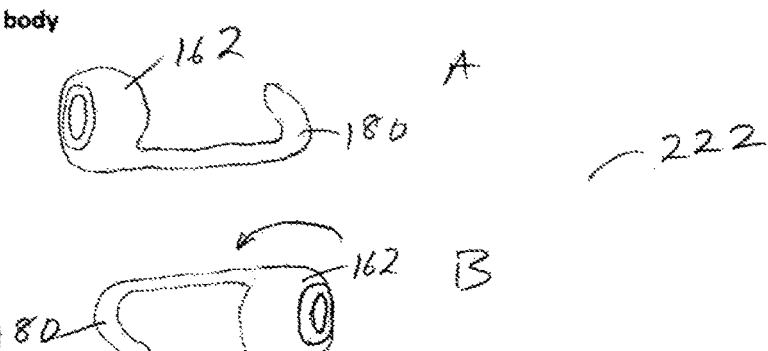
FIG. 98.   Bud with concha piece that rotates
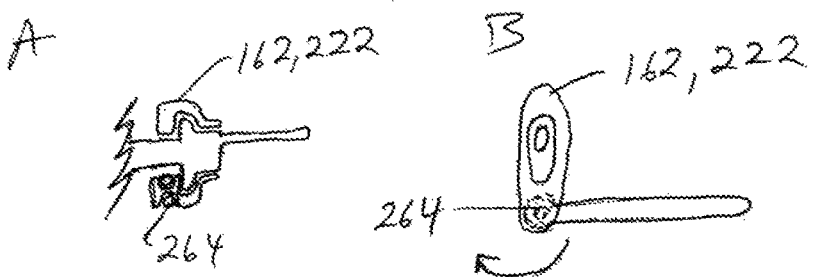
FIG. 99.   Two piece bud with a rotating component
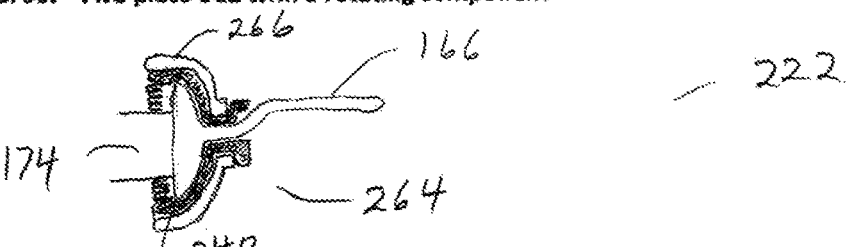
FIG. 100. Bid that snaps in from the side and rotates around neck extension of main body
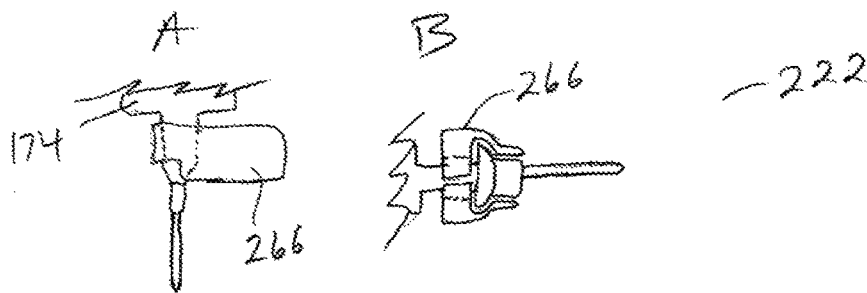

FIG. 101. Alternative configuration of main device attachment and extension and two different rotating bud attachments

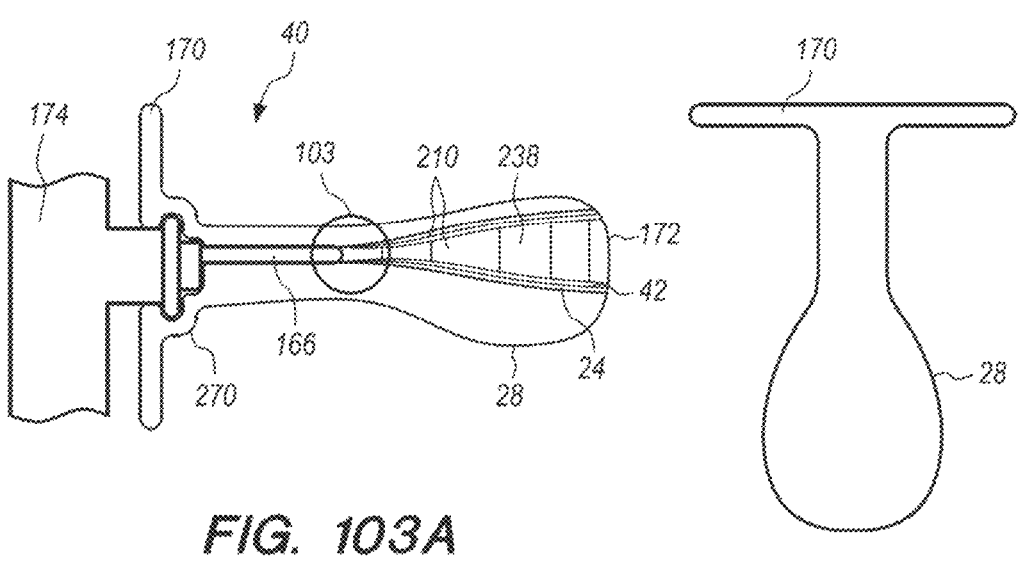
*FIG. 103A*
*FIG. 103B*
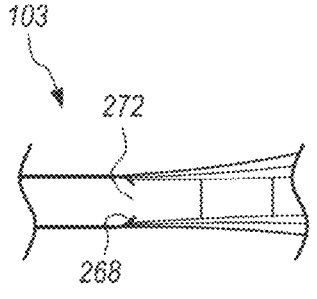
*FIG. 103D*
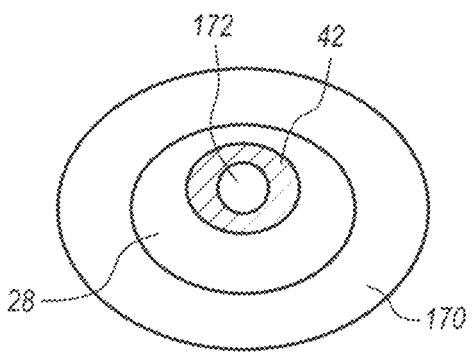
*FIG. 103C*
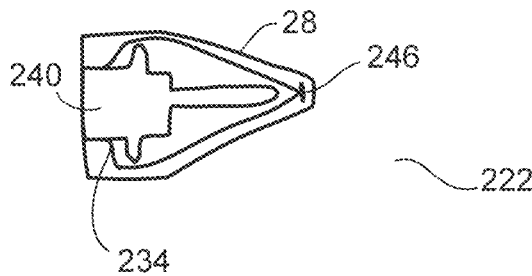
FIG. 104

DEVICES WITH EXTENDABLE OR RETRACTABLE OR MOVEABLE COMPONENTS
FIG. 105. Extendable extension
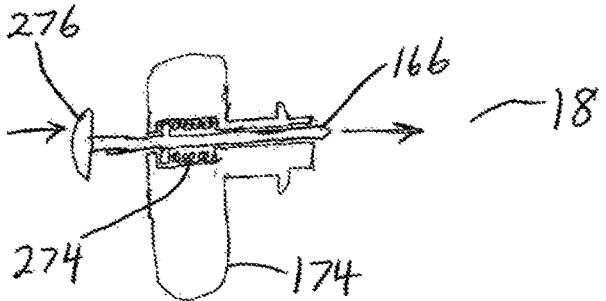
FIG. 106. Compressible attachment (i.e. ear bud) to extend extension
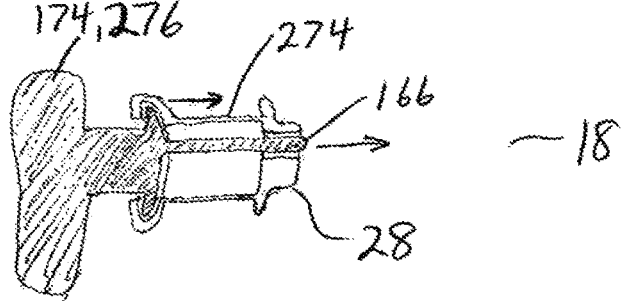
FIG. 107. Extendable and retractable (i.e. for safety) extensions
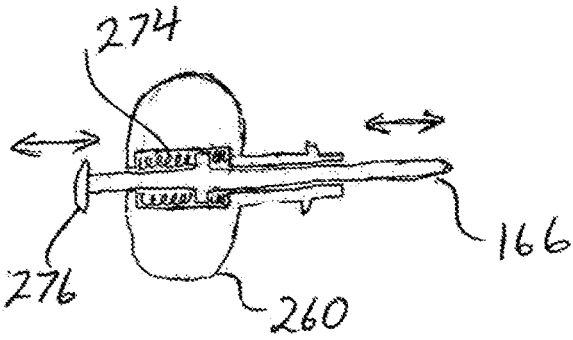

FIG. 108.  Angled Push Rod
A
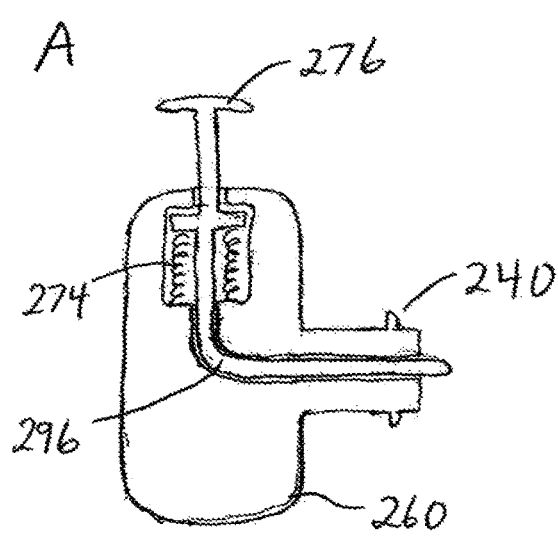
276
274
240
296
260
B
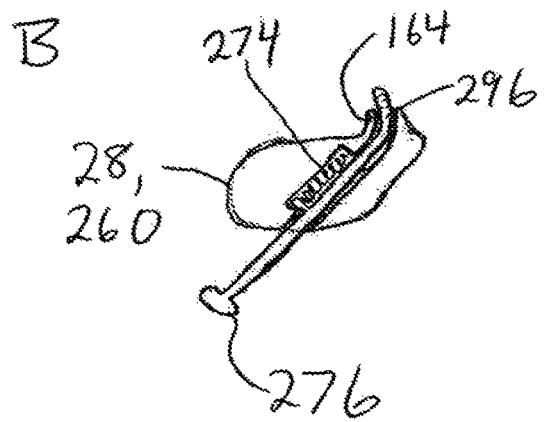
274
164
296
28, 260
276

FIG. 111A
FIG. 111B
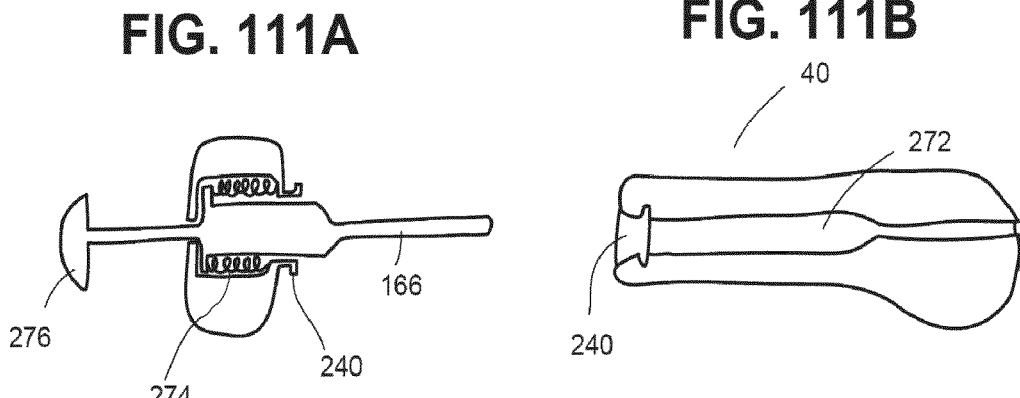
FIG. 112. Extendable and retractable extension to fit two or more attachments requiring different lengths
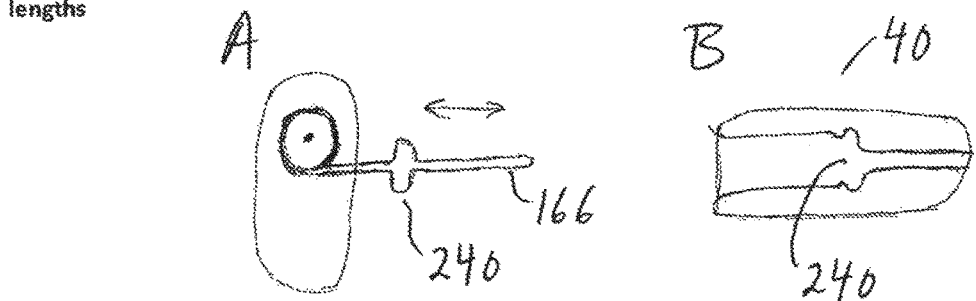
FIG. 113. Extension retracts with attachment of an ear bud and is otherwise positioned to fit an oral attachment or used to image the oral cavity without an attachment
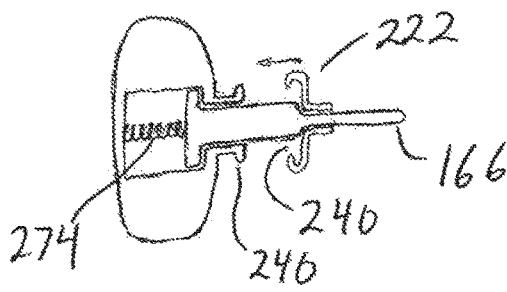

FIG. 115. Extendable and retractable configuration with chip in the main body
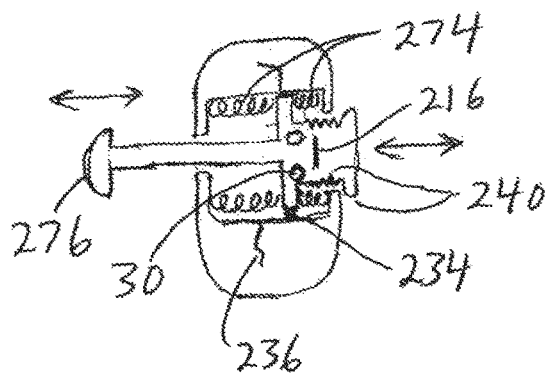
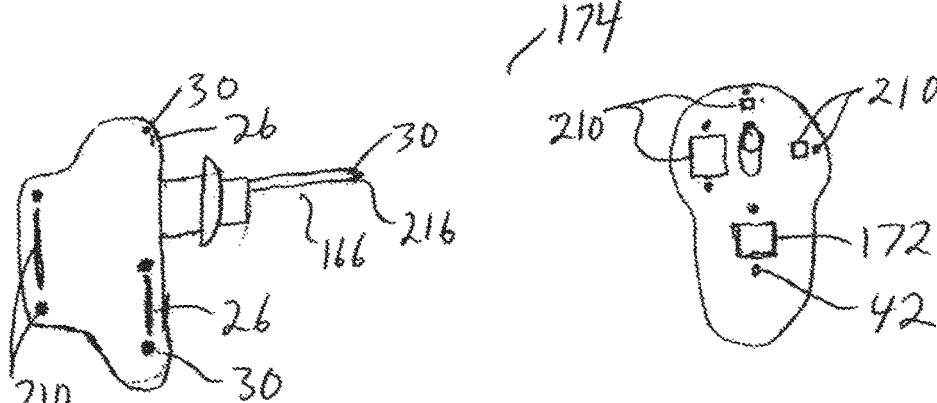
FIG. 116A
FIG. 116B

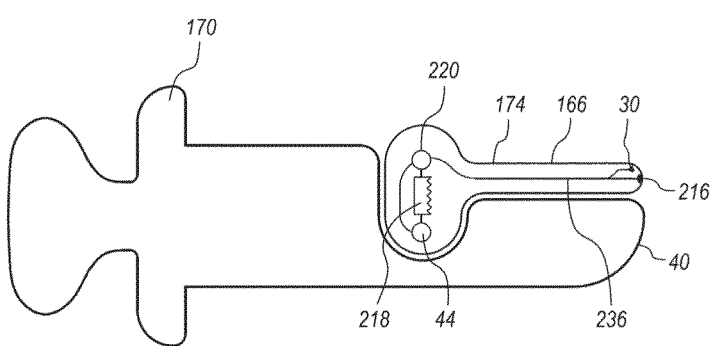
*FIG. 117*
FIG. 118A
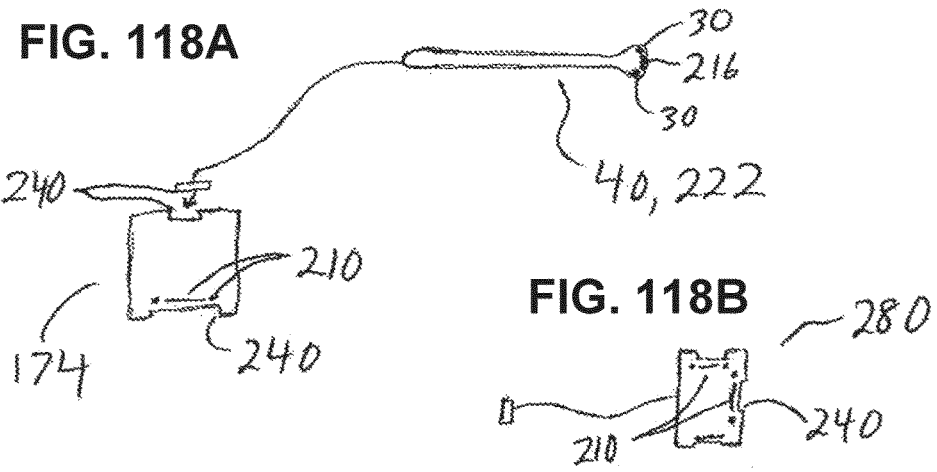
FIG. 118B
FIG. 119. Cotton swab style long extension with a main body housing components. This may attach to or fit into other attachments
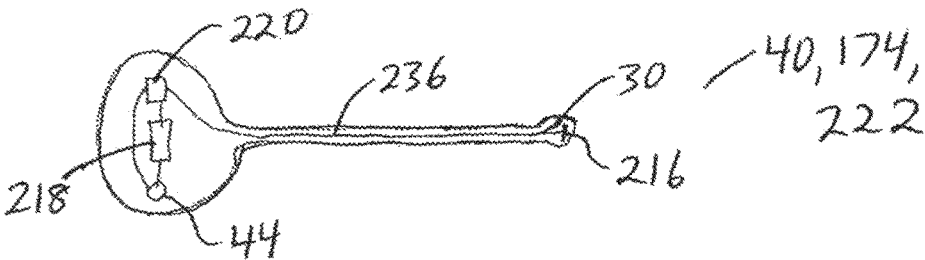

DEVICES, METHODS, AND SYSTEMS FOR ACQUIRING MEDICAL DIAGNOSTIC INFORMATION AND PROVISION OF TELEHEALTH SERVICES

This application is a continuation of prior, co-pending U.S. application Ser. No. 15/573,432, filed on May 12, 2016, which is a national stage application of International Application No.: PCT/US2016/032223, filed on May 12, 2016, which claims the benefit priority of U.S. Provisional Application No. 62/160,468, filed on May 12, 2015, all of which are incorporated herein in their entirety. This application also incorporates herein by reference in their entirety U.S. patent application Ser. No. 13/929,591, filed on Jun. 27, 2013, and U.S. Provisional Application No. 61/664,920, filed on Jun. 27, 2012.

FIELD OF THE INVENTION

The invention relates generally to various systems, tools and methods for acquiring diagnostic information, including medical information, for a user, transmitting the information to a remote location, assessing the information, and transmitting resulting diagnosis and treatment information to the user and/or a third party for subsequent action. More specifically, the present invention relates to consumer and user-friendly telemedicine systems and procedures which enable health services and/or diagnoses to be provided remotely.

BACKGROUND OF THE INVENTION

Currently, subjects with an injury or undiagnosed pain are typically forced to visit one or more physicians or medical treatment centers to have their condition diagnosed. If the subject is a small child, or if the condition is thought to be serious or in need of immediate treatment, the long waiting periods for a physician appointment may seem unreasonable or unacceptable, and the subject often ends up going to an emergency room and/or urgent care center on a "walk-in" basis. At the medical facility, the subject (or his/her guardian or caregiver) fills out medical history forms, answers questions about the condition, and has a clinician perform a physical examination to learn about the condition. In many cases, the waiting period at the facility can consume many hours, depending upon facility capacity and other subject needs (e.g., emergency cases treated as priority, etc.). Ultimately, the subject's visit may have been unnecessary, as the condition was not truly "urgent" or "critical," and thus treatment could have been delayed and/or accommodated at a regularly scheduled appointment, or the condition would have resolved itself with little or no intervention by the physician.

In many cases, the stress and uncertainty associated with the subject's condition can be more debilitating than the condition itself, especially where the subject is a small child, and the caregiver is an inexperienced parent who is anxious about his or her child's condition. Moreover, because emergency treatment centers such as emergency rooms and urgent care centers are operating at or over capacity, the long wait times at such facilities can further exacerbate stress, leading to a wide variety of potential medical situations including hypertension, heart attacks and/or strokes, as well as possible physical and/or mental altercations between subjects and/or caregivers. Moreover, the unnecessary use of emergency and urgent care facilities levies a heavy cost on the nation's health care and health care insurance systems, as such services are generally much more expensive than similar services provided on a scheduled or appointed basis.

SUMMARY OF THE INVENTION

The various inventions disclosed herein include the identification of a need for consumer-/and/or user-friendly devices that can be employed by untrained or semi-trained individuals to safely and effectively capture, store, transmit, display, download and/or update medical or other information, including assessments, examinations, and evaluations, of a subject's condition via electronic media for use by subjects, clinicians, health care providers, and system administrators. In accordance with one exemplary embodiment of the present disclosure, the method includes, without limitation, a non-medical professional (e.g., a consumer or other subject, etc.) utilizing a device to perform an examination protocol for a subject's condition, the device having the capability to store and/or transmit relevant information for use in an asynchronous or other telemedicine environment.

The performing of the examination can include storing information about the subject's condition in a storage medium, include storage media accessed remotely (e.g., USB-accessible, LAN-accessible and/or internet accessible storage devices), as well as localized storage associated with the device (e.g., RAM or flash memory, SD cards, attached smartphone memory, etc.). The device can simultaneously and/or subsequently upload stored data to a general or specialized storage network, or remote access to the electronic storage medium can be provided over a computer or other communication network. The stored data can then be accessed by a competent medical professional or other caregiver, properly assessed, and recommendations regarding the condition and/or treatment can be transmitted or otherwise given to the subject or guardian.

Various embodiments disclosed herein include the manufacture, distribution and use of specialized and/or generalized devices that can be utilized by non-medical personnel (e.g., consumers) to collect subject information in a homecare or non-medical facility location. The information can then be transmitted and/or otherwise accessed by qualified medical and care-giving personnel, and appropriate assessment, condition and/or treatment information can be transmitted or otherwise provided to the subject. In various embodiments, the device can be a part of and/or used in conjunction with electronic communications and/or display systems such as telephones, cell phones, smart phones, computers, wireless radios and/or other communications media known in the art. Desirably, the disclosed systems will allow a subject to transmit sufficient information to the medical professional to enable assessment of the subject's condition, which may include information relevant to immediate and/or critical treatment of the condition that may not be readily apparent to the subject. In various embodiments, the inventive systems allow trained personnel to direct the subject's actions and/or use of the diagnostic tools, such as requesting information regarding specific anatomical features which may be imaged by the diagnostic device in the hands of the subject as requested "real time" by the physician.

In various embodiments, the disclosed systems and methods include the ability to collect subject information at a plurality of times or conditions, whereby the information can be transmitted and/or otherwise accessed by the medical professional and used in the assessment of the subject's condition. Such information may be stored for various periods of time, at differing locations, and previously-stored data can be transmitted and/or made available in conjunction with current subject information and used in the assessment of the subject's condition. Similarly, subject information collected via other methods, including routine physicals and/or during doctor office visits, can be collected and provided with current subject information in a similar manner. If desired, the specialized and/or generalized consumer device (or other device such as a smartphone or computer) can include memory features that collect and store such information, such as the identity and dosages of medicines currently being taken by the subject or the fact that the subject has diabetes or other medical conditions.

Various alternative embodiments include the provision of an internet-accessible healthcare system to consumers, whereby the consumer can provide subject information (as previously described) to the system, and can receive assessment, condition and/or treatment information from a healthcare professional associated with the system. In various embodiments, the system can provide the consumer and/or subject with status updates and/or other relevant information during the process to: (1) confirm receipt and/or integrity of the relevant subject information, including subject medical data and payment information, if necessary, (2) identify various steps of the process, and the subject information's current status (e.g., data assigned to a physician or specialist, data currently being reviewed, medical recommendations being prepared, system scheduling a local physician visit on subject's behalf, system directing subject to a local emergency room, system dispatches an ambulance or paramedics to the subject's location, etc.), (3) request additional information from the subject (either using the current device and/or additional devices, some of which may be immediately available to the subject) which may include initiating a live-call or other communication between the medical professional and the subject, (4) providing assessment, treatment and/or other information to the subject, and (5) forwarding prescription or other treatment information to the subject, hospital, pharmacy or other care-giver as requested by the subject and/or assigned by the system.

In various embodiments, the provision of the type of updates can significantly reduce subject anxiety while waiting for treatment information, as well as confirm to the subject whether the subject information has been received and/or is being reviewed by the system. In addition, in situations where the subject is unable or unwilling to access emergency services directly (e.g., the subject is stuck in an accident on the road, lost in the wildness, climbing a mountain, located in a collapsed building, etc.), the present system and methods described herein can provide critical care data directly to the subject, as well as provide emergency response personnel with detailed information about a subject's condition, that may take mere seconds for the device to collect, allowing responders to prioritize their response and/or equip themselves for specialized medical responses.

In various embodiments, the present system can be associated with various healthcare-providing organizations and/or payors, including clinics, hospitals, insurance companies, employers and/or governmental entities, as necessary and/or allowed by current or future laws (e.g., privacy and health care information accessibility statutes, etc.). The use of such systems by such entities can significantly reduce congestion of existing emergency as well as non-emergency health services (by reducing the number and/or frequency of unnecessary subject visits) as well as significantly improve the provision of health care to the general consuming population in a highly effective and cost-efficient manner. Moreover, various embodiments of the system can significantly reduce the need for medical professionals to be located proximate to their subjects, and can even promote and/or encourage "time shifting" of medical care by subjects and/or medical professionals.

Various technical features of the invention generally relate to devices, systems and methods that facilitate remote connection and communication between two or more parties for medical, health and/or wellness purposes, herein collectively referred to as telehealth. In various embodiments, technical features are disclosed that generally relate to devices, systems and methods for capturing, displaying, recording and/or transmitting diagnostic information, including remote control manipulation of devices and/or diagnostic information. Other technical features of the invention generally relate to devices, systems and methods that provide the infrastructure, logistics and user interfaces to make possible remote or at home diagnosis, advice and/or coaching for medical, health and/or wellness purposes (herein collectively referred to as health purposes). Other technical features of the invention generally relate to devices, systems and methods providing advanced features for a more pleasurable user experience and/or more elaborate telehealth system.

In various embodiments, the systems and methods disclosed herein can facilitate one or more of the following (including various combinations thereof):

A. Reduction of health care costs for both payer and subject/consumer;

B. Providing adequate subject access to primary care physicians. The invention desirably accommodates reducing the number of primary care physicians and increasing the number of subjects able to be served;

C. Early diagnosis focusing to help minimize disease progression;

D. Accommodation of modern fast-paced life/culture. Modern communications methods and widespread internet/wireless connections have created consumers' expectations for more convenient and more rapid answers and access to information, including 24-hour and/or "real time" access to services;

E. Consumer-friendly and/or ruggedized information capture devices: The invention provides access to telemedicine and creates a need for the ability to capture diagnostic information remotely; and F. Reduction of the number of high-cost visits to an emergency room or facility/urgent care.

The present disclosure relates to devices, systems and methods to capture diagnostic information for health and wellness. As one example of a system, a parent uses a device to capture an image of a child's eardrum while at home. The device transfers the images to a local computing device, such as a laptop, tablet or smart phone. If the parent is using the computing device for a live video or chat consultation with a provider, the images may be sent to the provider in real time. An alternative method does not require the images to be sent in real time. The store and forward method allows a user to send the images to a provider at any time for review without a communication connection between the user and provider. Current home diagnostic devices and attachments are typically modeled after doctor instruments. These devices often require training and practice and are typically awkward, unfamiliar and uncomfortable. This disclosure describes devices, systems and methods to improve tolerance, safety, ease of use and portability (for example, a compact kit). Some features which serve to accomplish this are the use of familiar interfaces (for example, comparable to a BLUETOOTH headset or a pacifier), providing support and/or alignment and the use of flexible and/or soft portions which interface with the body.

Other features to increase the ability to capture this information may also be incorporated. For example, a speaker may be incorporated to emit pleasant sounds to calm the subject, which may be especially useful when capturing images of a child's ear drum. Oral attachments or sleeves placed over attachments or devices may be chilled or flavored for a more pleasant experience for the subject. Additional diagnostic elements may be included with any of these devices. For example, a thermometer or sensors (i.e. for oxygen saturation, pulse etc.) may be incorporated into the main body of the device and/or incorporated into an ear or oral device or attachment. Similarly, a single device may incorporate one or more features of the present disclosure. For example, a device may have a built in component which serves as a stethoscope to listen to the heart and lungs (i.e. it does not require an additional stethoscope attachment) and also have a camera to look into the ear and throat. This camera may be at the tip of an extension or at the base of an extension. In this case it may be possible to capture images of the ear and throat without additional attachments, but attachments may be supplied as optional accessories, for example to allow easier, more reliable or more comfortable use. Alternatively, a kit (device and/or attachments) can be provided for capturing other diagnostic information, such as images of the eye and skin or a device or attachment can be supplied to capture information at only one location.

In various alternative embodiments, similar systems and methods as described herein may have varying levels of utility in non-health care applications, including the collection of relevant data using similar devices and/or the provision of "expert" advice for various other purposes, including non-medical diagnostics such as carpentry, plumbing, auto repair, etc.

It is to be understood that a reference to an individual encompasses singular and plural instances of the individual. For example, a medical care professional or provider may be a single person providing medical care, or multiple individuals working in concert to provide complementary service(s) to the subject or caregiver. Similarly, a caregiver can be a single individual such as a parent, or multiple individuals such as attendants at a nursing home.

In certain instances herein, components of the invention may alternatively be referred to as elements. These terms, as well as other comparable terms, are to be considered as interchangeable.

An embodiment of one aspect of the present invention is directed to an imaging apparatus for obtaining images inside a subject's ear canal. The imaging apparatus according to this embodiment comprises a main body and an extension having a central axis structurally configured for insertion into the subject's ear canal. The imaging apparatus comprises an imaging element for obtaining images which are angled and/or offset relative to the central axis of the extension into the ear canal. Alternatively, the imaging apparatus may be configured to obtain images in line with the central axis of the extension but where the extension is offset and/or angled relative to the ear canal central axis. Further, the imaging apparatus may obtain images which are angled and/or offset relative to the central axis of the extension and angled and/or offset relative to the central axis of the ear canal. The main body and/or extension may engage with the outer ear or ear canal to encourage these positions.

The imaging apparatus may comprise an engagement member which is structurally configured to be supported in-use by a subject's ear or head so that the user, provider, or caregiver does not need to support or hold the apparatus in position.

The imaging apparatus may comprise a wireless transmission element for wirelessly transmitting the obtained images to a processing or computing device. Alternatively, the imaging apparatus may communicate with a processing or computing device via a wired connection. A non-limiting list of examples of computing devices include mobile telephones, smartphones, laptop computers, tablet computers, desktop computers, servers, mainframes, and dedicated hardware computing devices. These devices can operate using mobile operating systems such as iOS (from APPLE INC.) and ANDROID (from GOOGLE INC.), desktop operating systems such as OSX (from APPLE INC.) and WINDOWS (from MICROSOFT CORP.), or any other kind of operating system or platform. The computing device can also be custom-designed and manufactured for use specifically with the imaging apparatus.

The extension portion of the imaging apparatus may have a soft outer surface for improved subject comfort during insertion of the extension into the subject's ear canal.

An embodiment of another aspect of the present invention is directed to an oral imaging apparatus in the shape of a pacifier. The imaging apparatus may comprise an imaging element configured for taking an image of the oral cavity of a subject; and a transmission element for transmitting the image to a processing or computing device.

An embodiment of another aspect of the present invention is directed to a kit for collecting diagnostic information of a subject. Although different embodiments of the kit may contain different components, a useful combination comprises a main body and one or more attachments. The main body comprises diagnostic equipment, such as processing and/or computing elements, for obtaining medical diagnostic information of the subject, and a transmission element for transmitting the diagnostic information via wired or wireless connection to a computing device.

A useful first attachment for the main body comprises an imaging element structurally configured for imaging the ear canal and/or the ear drum of the subject. A useful second attachment for the main body comprises an imaging element structurally configured for imaging the oral cavity and/or throat of the subject. The kit may also comprise a third attachment having a sound accessing element structurally configured to obtain internal sounds of the subject's body. The kit may comprise any combination of first and/or second and/or third attachments.

The transmission element in the kit may be configured to transmit the diagnostic information in real time as the device is in use, or the diagnostic information may be transmitted upon receipt of an instruction from a user or provider. The transmission element may have the capability of transmitting the diagnostic information in a plurality of image resolutions, image sizes, or transmission speeds, or combinations thereof. For example, the transmission element can be configured to send images at VGA, SVGA, HVGA, or another resolution, or video at 12 frames per second, 24 frames per second, or another frame rate.

Any of the components of the kit such as the main body may be structurally configured as a hands-free unit while in-use, or as a handheld unit while in-use.

Another aspect of the present invention provides for a method of remotely providing medical information to a subject by a health care professional. The method may comprise the steps of:

a. providing, via a remote connection, the subject's current medical data to the health care professional;

b. optionally providing the health care professional with the subject's medical history;

c. causing the health care profession to develop an assessment of the subject's current physical condition on the basis of the current medical data and the medical history if available; and d. communicating the assessment to the subject or subject's caregiver over an electronic communications channel.

The method may also include providing, by the health care professional, the subject or subject's caregiver with treatment information (but not limited to). The treatment instructions can include any kind of medical advice or instructions, such as providing the subject with a prescription for a drug or a laboratory procedure; or directions to visit a medical care provider, pharmacy, hospital, or laboratory. Multiple instructions can also be given to multiple parties. For example, the health care professional can provide (a) the subject's caregiver with verbal medical care instructions; (b) a pharmacy with a prescription for filling; and (c) a laboratory with advance notice that the subject will need a certain kind of test to be performed.

Another aspect of the present invention is directed to a method of remotely providing medical information by a health care provider to a subject. The method may comprise the steps of:

a. providing, via a remote connection, instructions to an untrained or semi-trained consumer to perform an examination protocol for a subject's condition using an examination device which stores and/or transmits current subject medical data for use in an asynchronous or telemedicine environment;

b. transmitting, by the consumer, the examination protocol data to the health care provider;

c. causing the healthcare provider to develop an assessment of the subject's current physical condition on the basis of the data obtained by the examination device; and d. communicating the assessment to the subject or the subject's caregiver over the remote connection.

The method may further comprise providing, by the health care professional, the subject or subject's caregiver with treatment information for the subject.

The examination protocol data can be transmitted to the health care provider in real time, as the data is acquired, or not in real time, for example, upon receipt of an instruction or request from the provider or health care professional for this data. In such embodiments, the examination protocol data can be stored in a storage medium such as a flash drive in a device participating in the performance of the invention. The examination protocol data can also be saved in a computing device, or be uploaded to a cloud-based data storage facility for retrieval by the health-care provided in real-time or upon issuance of an instruction.

An embodiment of another aspect of the present invention is directed to an examination device for performing an examination protocol for a subject's condition. The examination device can comprise:

a. an anatomical interface structurally configured for application to a predetermined area of the subject's body;

b. an accessing and capturing component which obtains current medical data of the subject after application of the anatomical interface to the subject's body;

c. a diagnostic processing component which processes the medical data obtained by the accessing and capturing component; and d. a communications link over which the processed medical data is transmitted to a communications component for viewing and interpretation by a medical care provider.

The anatomical interface is structurally configured for application to the subject's ear, nose, throat, eye, wrist, skin, head, skin, extremities, torso, or into a body orifice such as the inside of the mouth or nose. In this manner, the anatomical interface of the device will facilitate providing accurate subject medical status information.

Any of the disclosed devices, systems, or components may comprises a remote control component which is structurally configured to respond to control signals sent remotely by the medical care provider or a caregiver over a communications link. The communications link can transmit the obtained medical data in the form of still images, a video feed, an audio feed, a data stream, or a combination thereof, to the medical care provider.

Any of the disclosed devices, systems, or components may comprises a port or jack configured for attachment to a computing device such as a mobile telephone, laptop computer, tablet computer, or desktop computer. The port or jack may be conventional such as a minijack, USB port, APPLE iDevice port (such as an IPHONE or IPAD), or custom-designed by the manufacturer.

Examples of the accessing and capturing component of the present invention include a mobile telephone, laptop computer, tablet computer, desktop computer, or a custom-designed hardware element.

Examples of the diagnostic processing component of the present invention include a mobile telephone, laptop computer, tablet computer, desktop computer, or a custom-designed hardware element. In certain embodiments of the invention, the accessing and capturing component and the diagnostic processing component can be the same hardware element. That is, the hardware element can have multiple functions as discussed and provided in this specification.

An embodiment of another aspect of the present invention is directed to a telehealth system for remote diagnosis of a subject's medical condition. The telehealth system can comprise elements such as:

A. a user subsystem configured for receiving a subject's current medical data, the user subsystem comprising:

1. a communication device;

2. a diagnostic processing device; and 3. a diagnostic capture device;

B. a provider subsystem configured for communicating with a health care provider, the provider subsystem comprising:

1. a communication device; and

C. an infrastructure subsystem configured to process and store medical data and diagnostic information received from the user subsystem and the provider subsystem, the infrastructure subsystem comprising:

1. an application server comprising computer instruction code configured to communication with:

a. a database configured to store a subject's personal information and electronic health record;

b. diagnostic computer instruction code configured to receive current subject medical information and to provide diagnostic information concerning the subject's medical condition; and c. a database configured to store archived diagnostic information;

2. a server comprising computer instruction code configured to communicate with one or more third-party subject personal information or electronic health record databases; and 3. a server comprising computer instruction code configured to communicate with a third party telehealth system, wherein the user, provider, and infrastructure subsystems are structurally configured to communicate information over an electronic data network.

Another aspect of the present invention is directed to an imaging apparatus for obtaining images within a body cavity of a subject, the imaging apparatus comprising a main body, an extension having a central axis structurally configured for insertion into the body cavity, and an imaging element structurally configured to facilitate the capture of images from a perspective offset from the extension. In an embodiment of the invention, the body cavity is the ear canal of the subject.

Another aspect of the present invention is directed to a medical diagnostic device comprising at least one anatomical interface and which is structurally configured to position, align, or stabilize the device or a subject's tissue when the device is applied to the subject's body.

Another aspect of the present invention is directed to an attachment for a medical diagnostic device, the attachment comprising at least one anatomical interface and which is structurally configured to position, align, or stabilize the device or a subject's tissue when the device is applied to the subject's body.

Another aspect of the present invention is directed to a medical diagnostic device comprising at least one anatomical interface and which is structurally configured to position, align, or stabilize the device or a subject's tissue when the device is applied to the subject's body, wherein the anatomical interface has an extendable structure having a variable length for adjustment of position of diagnostic elements when applied to a subject's body.

Another aspect of the present invention is directed to an attachment for a medical diagnostic device, the attachment comprising at least one anatomical interface and which is structurally configured to position, align, or stabilize the device or a subject's tissue when the device or attachment is applied to the subject's body, wherein the anatomical interface has an extendable structure having a variable length for adjustment of position of diagnostic elements when applied to a subject's body.

Another aspect of the present invention is directed to an imaging apparatus structurally configured for application to a subject's oral cavity or throat, wherein the apparatus comprises a light input and/or output which is positioned within the oral cavity during use.

Another aspect of the present invention is directed to an attachment for an imaging apparatus, the attachment structurally configured for application to a subject's oral cavity or throat, wherein the attachment comprises a light input and/or output which is positioned within the oral cavity.

Another aspect of the present invention is directed to a stethoscope device comprising a camera structurally configured to assist a user to position the device and/or to confirm correct positioning of the device.

Another aspect of the present invention is directed to a stethoscope attachment for a device, the attachment comprising a camera structurally configured to assist a user to position the stethoscope attachment and/or to confirm correct positioning of the stethoscope attachment.

Another aspect of the present invention is directed to a medical device structurally configured for placement into a subject's ear canal for imaging of the ear canal or ear drum, wherein the device is configured to obtain an image of the ear canal or ear drum without substantial manipulation of the subject's outer ear during use.

Another aspect of the present invention is directed to an attachment for a medical device, the attachment structurally configured for placement into a subject's ear canal for imaging of the ear canal or ear drum, wherein the attachment is configured to obtain an image of the ear canal or ear drum without substantial manipulation of the subject's outer ear during use.

DEFINITIONS

For convenience, further information regarding the following terms is provided below. Other and equivalent terms in this description may be used to describe similar concepts.

Subject: One or more individuals desiring or needing health advice. A subject may be a group, e.g. exercise class or sport team.

Caregiver: One or more individual(s) that assist the subject with his or her health concern. This individual is usually known to the subject, e.g. a son or daughter or parent or coach.

User: One or more subject(s) and/or caregiver(s).

Health Professional: Any individual certified or experienced within a health related field. Examples include a physician, surgeon, nurse, physician assistant (PA), nurse practitioner (NP), physical therapist, nutritional expert, medic, paramedic, EMT, etc.

Nurse Hotline: A service provided by an insurance company or health-related entity that provides health advice or helps connect an individual with the appropriate health professional.

Call Center: A service, that may be provided by a non-health related entity, that provides health advice or helps connect an individual with the appropriate health professional.

Provider: One or more health professional(s), nurse hotline and/or call center.

DESCRIPTION OF VARIOUS EXEMPLARY EMBODIMENTS

Although the disclosure hereof is detailed and exact to enable those skilled in the art to practice the invention, the physical embodiments herein disclosed merely exemplify the invention, which may be embodied in a manner not expressly described. While the preferred embodiment has been described, the details may be changed without departing from the invention, which is defined by the various disclosures and claims provided herein.

BRIEF DESCRIPTION OF THE FIGURES

FIGS. 1 and 2 illustrate exemplary embodiments of a telehealth system in use.

FIGS. 32-35 illustrate exemplary embodiments of medical diagnostic instruments for collection of subject medical information.

FIGS. 39A-40B illustrate the basic anatomy of the ear canal and oral cavity, respectively.

FIGS. 41A-41B shows embodiments of interfaces for the oral cavity.

FIGS. 42A-42B illustrate difficulties associated with use of an otoscope which are addressed by the present invention.

FIGS. 43-45B illustrate ear position and speculum positioning during an examination with an otoscope.

FIGS. 46-48 illustrate visualization of the throat using conventional diagnostic instruments and techniques.

FIG. 49 illustrates an exemplary new device for accessing and capturing diagnostic information in the ear.

FIGS. 52A-56B show examples of preferred positions and angles for obtaining diagnostic information in the ear.

FIGS. 57A-61B show examples of anatomical interfaces which help to support, stabilize, position, and/or align devices, components or attachments in, on or near the visible portion of the ear, head, neck or cheek.

FIGS. 62A-65E show examples of anatomical interfaces which help to support, stabilize, position, and/or align devices, components or attachments in or near the ear canal.

FIGS. 66A-67B show examples of light output locations and image/light input locations for diagnostic elements intended for the ear.

FIGS. 68A-71B show examples of inflatable, expandable, or hinged components for use with diagnostic elements.

FIGS. 72A-74J show various positions of devices and configurations of imaging elements, including angle and field of view, for viewing the oral cavity and throat.

FIG. 75A-79G show various profiles of devices and examples of positions of diagnostic elements; examples of anatomical interfaces with different configurations and profiles; and exemplary shapes of anatomical interfaces and positions of imaging elements.

FIGS. 82A-83C show examples of anatomical interfaces for imaging the nose or nasal cavity and eye.

FIGS. 84A-89C show elements of diagnostic kit devices for imaging the ear canal and ear drum, and including a main device and various attachments.

FIGS. 90A-90C illustrate a main diagnostic device with an extension that contains diagnostic elements at the tip to emit light, and a video chip to capture light.

FIGS. 91A-104 show attachments for a main device and examples of configurations of the main device. FIG. 91A-91B show a display attachment that can connect to the back of the main device. FIG. 92A-92B illustrate a slim ear bud sleeve that can connect to the main device and allow imaging of either the right or left ear. FIGS. 93A-101B illustrate ear bud attachments to the main device, including attachments which have light source and light measurement capabilities, and attachments which rotate.

FIGS. 103A-103D illustrate an oral attachment which attaches over a diagnostic extension of a main device.

FIG. 104 illustrates an ear temperature attachment for connection to a diagnostic extension of a main device.

FIGS. 105 through 109C show various configurations of extendable, rotatable or moveable diagnostic sections or extensions of a device.

FIGS. 111A through 113 show devices with diagnostic extensions that can fit attachments with different lengths.

FIG. 115 shows an example of a configuration with diagnostic elements in the main body of a device that allows extension and retraction.

FIGS. 116A-116B shows a device with various diagnostic elements at different locations in a device.

FIGS. 117-119 show various other configurations of devices and kits, including long extensions which can attach to other attachments or elements.

DETAILED DESCRIPTION

This disclosure discusses and describes devices, methods, systems and features which reduce or eliminate the safety, tolerance, comfort or usability issues that exist with current diagnostic devices and allow for an easier and more comfortable experience, even if the user has minimal or no training. The preferred device designs perform the same function as instruments found in a doctor's office, but are packaged in forms and shapes which are more familiar and/or more comfortable to both a child and parent. These features reduce nervousness for subjects (especially children) whose senses are usually naturally threatened by medical instruments, and also reduces nervousness for the user, who has more confidence using the more familiar and comfortable device.

I. Pertinent Anatomy of the Ear, Oral Cavity and Throat

It will be useful to provide a brief summary of the pertinent anatomy of the ear, oral cavity, and throat, as embodiments of the invention will be described with reference to such anatomical features.

A. Outer Ear and Ear Canal

1. Outer Ear Anatomy

Figure 8:
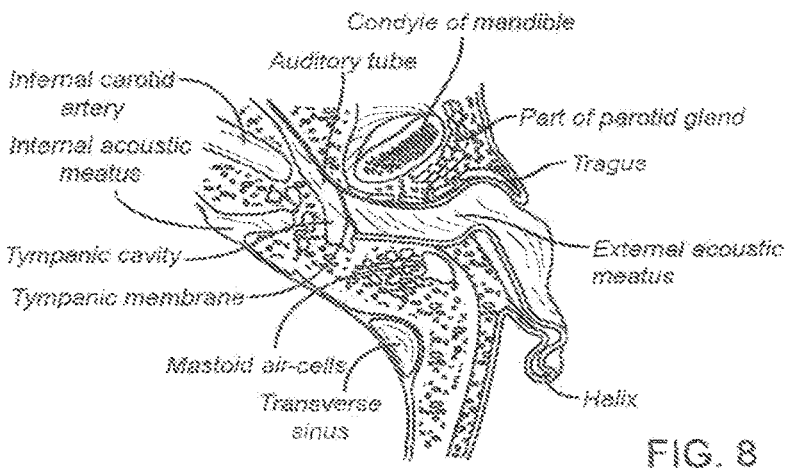
FIGS. 8 and 9 show a cross-section of the ear region of a subject's head for purposes of reference.
Figure 9:
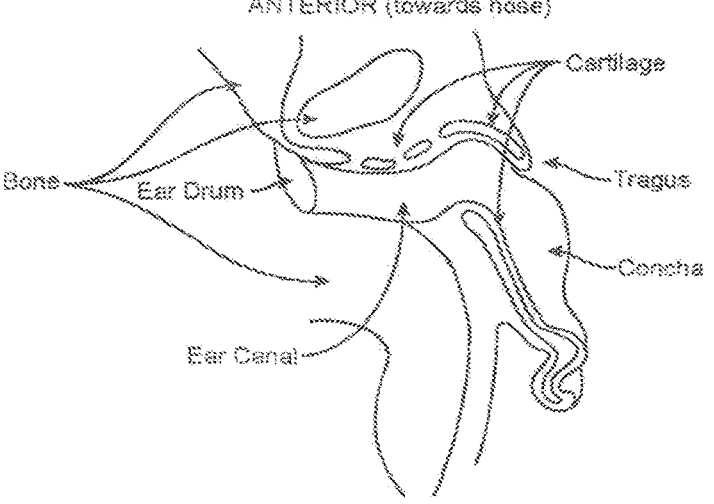
Figure 21:
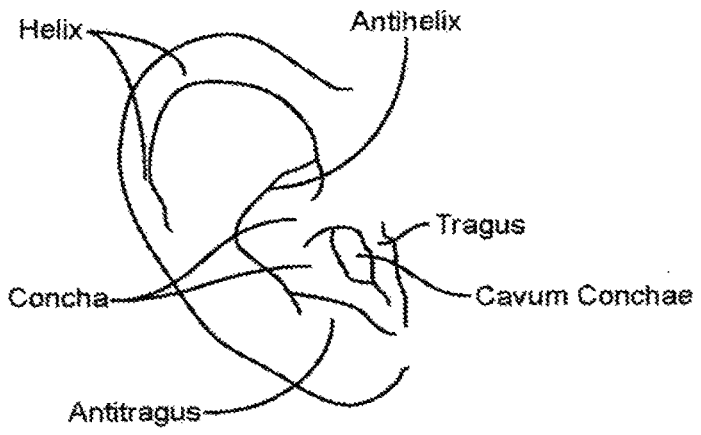
FIG. 21 illustrates features of the outer human ear for purposes of reference.

The outer ear consists of the visible portion of the ear, called the pinna or auricle, as well as the external acoustic meatus, or ear canal, which leads to the external surface of the tympanic membrane, or ear drum (see FIGS. 8,9,21). The tympanic membrane is translucent and part of the middle ear may be visualized through the membrane. The most prominent feature is the malleus. The condition of the tympanic membrane and ability to view the malleus are often used to diagnose ear problems. In an unhealthy ear, the tympanic membrane may be bulged or cloudy in appearance and it may be difficult to distinguish the malleus. The visible portion of the ear may also be referred to as the external ear. The pinna contains the concha, the tragus, the antitragus and the antihelix as well as other features. The concha is the bowl shaped part of the ear and leads into the ear canal. The tragus is located at the front of the concha and the antitragus is located below the concha. The antitragus is located behind as well as above the concha. The cavum concha is the inner portion of the concha that leads into the ear canal.

It will generally be clear in the following disclosure and on text as to whether the visible portion of the ear is intended, or whether the discussion is also applicable to or the entire outer ear which also contains the ear canal. However, the context of the description should be taken into account.

2. Ear Canal

Figure 39A:
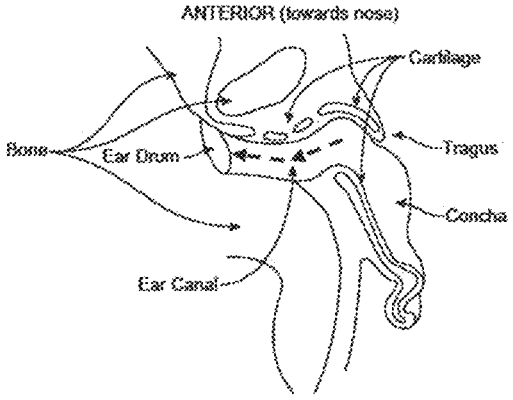

The external acoustic meatus, or ear canal, is generally oval shaped and largest at the entrance. The ear canal is curved in an S shape, directed superiorly and posteriorly (up and back) in the first section and then moving inferiorly and anteriorly (down and forward). The canal is straighter in newborns, gradually taking on the general shape of an adult's ear canal through growth, and the ear canal is generally shaped similarly to an adult after 12 months of age. The canal entry is generally in the range of 9 mm vertically (inferior/superior direction) by 6.5 mm horizontally (anterior/posterior direction) for adults. The canal length varies from about 1.5 cm in infants to approximately 2.5 cm long for adults. The ear canal diameter then decreases to an average diameter of approximately 6-7 mm in adults and 3 mm in infants. The ear canal consists of a cartilaginous section and a bony section. The cartilaginous section extends for almost the entire length in newborns and for approximately the first ⅓ of the length in adults. This outer portion the ear canal is where longer hairs are located, as well where wax is secreted. FIG. 39A is a horizontal, or transverse, section (upper, or superior, half shown) of the ear and ear canal showing the different parts of the ear as well as the curvature of the ear canal. The ear canal first runs posteriorly (to the back) and then anteriorly (to the front), as shown in FIG. 39A. The horizontal (anterior/posterior) dimension of the ear canal is shown to be similar throughout the length, which is approximately 6-7 mm on average in adults.

Figure 39B:
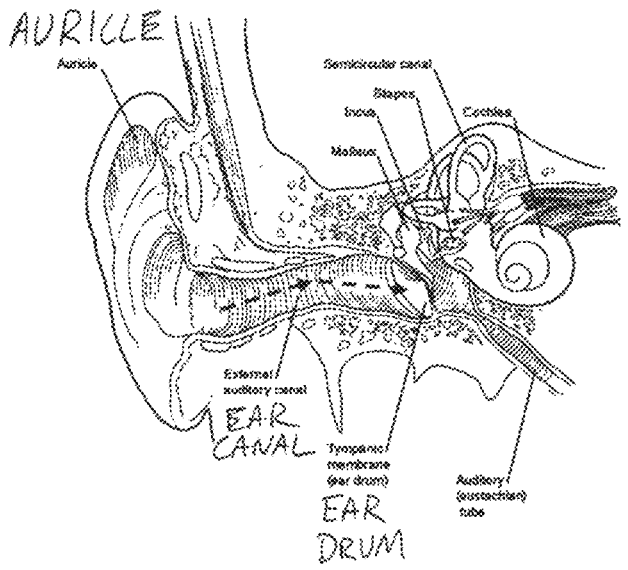

FIG. 39B is a frontal, or coronal, section (back, or posterior half shown) and shows the superior and then inferior shape of the ear canal (up and then down). The beginning section of the ear canal has a larger dimension in this section. The starting vertical (inferior/superior) dimension is approximately 9 mm on average in the adult and decreases to approximately 6-7 mm for the remaining length of the canal. Note that the sections may not be exact frontal and transverse sections showing the center of the ear canal due to the curvature of the ear canal in both directions.

B. The Mouth, Throat and Oral Examinations

1. The Mouth, or Oral Cavity

Figures 40A, 40B:
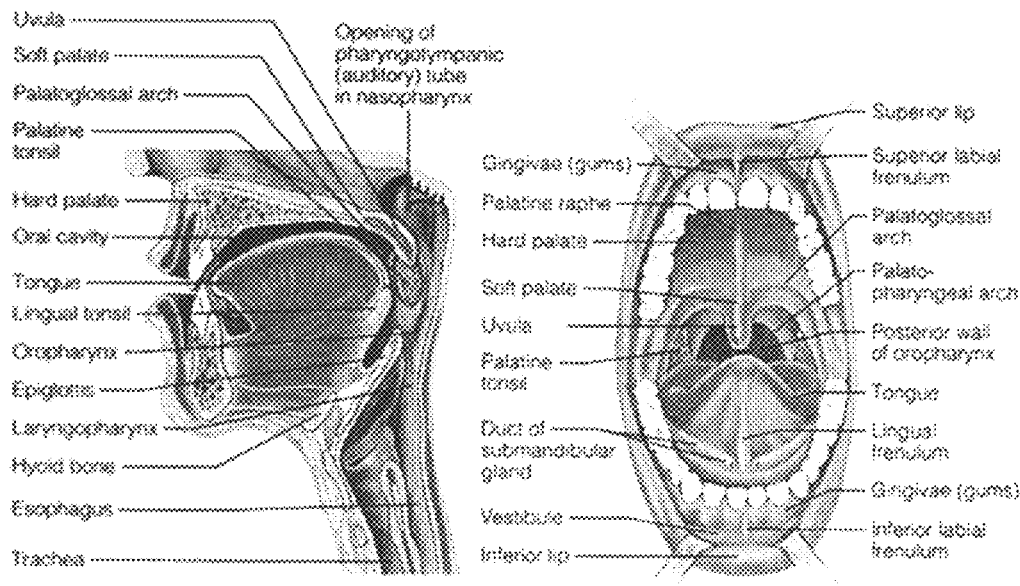

The main structures of the mouth, or oral cavity, are the teeth, the tongue and the palate (see FIGS. 40A, 40B). The oral cavity is connected to the outside by the lips at the front, or anterior end, and connects to the oropharynx (part of the throat) at the back, or posterior end. The oral cavity consists of two parts, the vestibule and the oral cavity proper. The vestibule is the area between the teeth, lips and cheeks. The inside of the cheeks are lined with the buccal mucosa. The top and part of the back of the oral cavity is formed by the palate, which separates the oral and nasal cavities. The front, or anterior, two thirds of the palate is the hard palate and the back, or posterior, third is the soft palate. The uvula extends down from the middle of the soft palate. The top, or superior, surface of the tongue is called the dorsum. The front two-thirds of the dorsum are part of the oral cavity. The oral cavity contains many small glands that, along with the three major salivary glands, produce saliva to keep the mouth moist and help keep the body healthy. These glands lubricate the mouth, help with swallowing, protect the teeth against bacteria and aid in the digestion of food.

2. The Oropharynx (Part of the Throat)

The oral cavity is connected at the back to part of the throat called the oropharynx (See FIGS. 40A, B). The oropharynx is connected to the nasopharynx at the top, which then connects to the nasal cavity. The bottom, or inferior border, of the oropharynx is defined by the epiglottis, at which point the hypopharynx (also called the laryngopharynx) begins. The side, or lateral, walls of the oropharynx contain a triangular recess which is defined by the tonsillar pillars. The front (anterior) pillar is called the palatoglossal arch and the back (posterior) pillar is called the palatopharyngeal arch. The palatine tonsils, or just tonsils, are contained within this triangular recess in the lateral walls of the oropharynx. The back wall of the oropharynx, or throat, is called the posterior pharyngeal wall. The back, or posterior, one third of the tongue surface (dorsum), or base of the tongue, forms part of the front, or anterior side, of the oropharynx.

3. Oral Examinations

Many structures may be visualized through the mouth to help a health care professional determine overall health and diagnose conditions. The general condition of the teeth and mucosa of the cheeks, gums and tongue are often inspected during a checkup at the doctor's office. The condition and size of the soft palate, tonsils, uvula, back wall of the throat, and opening of the throat are often helpful to indicate, diagnose or differentiate many conditions such as a cold, flu, sore throat, strep throat or tonsillitis. These structures, as well as the size of the tongue, are also important in determining the size of the airway and may be inspected to help determine if a sleep condition such as sleep apnea may exist.

II. Current Devices and Diagnostic Methods

A. Usability, Safety and Tolerance of Devices and Methods

1. Safety and Tolerance

Current diagnostic devices and methods often incorporate intimidating interfaces that are unpleasant and can create tolerability and safety problems, especially when in the hands of an inexperienced consumer rather than a trained professional. Examples of these interfaces are speculums and tongue depressors (see FIGS. 41A-41B). Tongue depressors are usually used when viewing the oral cavity and throat in order to depress the tongue, which usually blocks the view of structures such as the throat and tonsils. They can be uncomfortable and can cause safety problems, especially if used at home, for example, if the depressor is inserted too far or the child moves his or her head quickly and the depressor hits the back of the throat. Speculums are cone-shaped extensions on otoscopes which are inserted into the ear canal in order to visualize the ear drum. A speculum is typically inserted far enough into an ear canal to see beyond the hairs and wax inside the ear canal. The walls of the ear canal may be delicate and sensitive, especially when an ear infection is present. The bony portion of the ear canal, which runs the last ⅔ of the length of the ear canal, is especially delicate and sensitive and can be injured by objects such as the tip of a speculum. Tolerability problems can make it very difficult to view the ear drum and sometimes it is not possible at all. This situation is most common in younger children who are scared and uncooperative.

Forced use of these uncomfortable devices may cause at least a mild traumatic experience and even more difficulty diagnosing the child in the future due to the memory of the experience and refusal to cooperate when a similar situation presents itself. While these problems may be partially overcome through training and practice, as is done by providers such as physicians and nurses, they do not go away. While this training and practice is practical for a provider such as a nurse or physician, it is not practical to expect such training from the majority of consumers, for whom the risks and problems may still outweigh the potential benefits. In addition, the design of current diagnostic devices are unfamiliar (resembling medical office instruments) with intimidating interfaces that are inherently uncomfortable and which may seem to be threatening to the senses. Children are usually cautious of such devices and scared of them and a parent or other user does not feel confident using them. Training and practice do not eliminate these underlying factors which at best create an unpleasant experience.

2. Usability

Current devices are typically difficult to use and usually require training and practice. In order to image the ear drum with an otoscope, several variables need to be controlled. There are three parts (head, ear and otoscope) which move relative to each other. One hand is used to pull the ear back relative to the head in order to straighten the ear canal. The other hand is used to hold and position the otoscope. In order to maintain the position of the ear and otoscope relative to the head, one hand is often braced against the head and usually also against the otoscope which is being held in the other hand. All of these variables, as well as the orientation and depth of the tip of the speculum (portion of the otoscope which is inserted into the ear canal), are adjusted and controlled by the user in order to safely use the device and image the ear drum. A user should be able to see or feel the position of these moving parts while looking through a lens or at screen to know if the ear drum is in view. This is a difficult enough operation to describe, let alone to perform, and usually requires training, practice and "feel."

FIGS. 42A-42B show an otoscope in use. The user's left hand is pulling the ear to straighten the ear canal with some of the fingers braced against the upper neck. The otoscope is being held with the right hand, and it is also braced against the left hand while the user controls the orientation and depth of the speculum while looking through the viewing piece. This procedure is difficult enough to perform on an adult (as shown in FIG. 42), let alone on a young scared, child. Even a trained professional can sometimes have difficulties managing these variables in particular cases.

Similar difficulties exist when imaging the oral cavity and throat. The mouth is kept opened, the tongue is held down (usually achieved using a tongue depressor as shown in FIG. 41B) and an imaging device is oriented to capture the desired anatomy while the user looks through a viewfinder or at a screen (see FIG. 46). In this case, variables include head position, jaw position, tongue position and device position, as well as palate position in some cases. The user or medical provider may also look inspect the device or subject's oral cavity with his or her unaided eye, usually while shining a light into the mouth and throat.

B. Visualizing the Ear Drum and Diagnosing Ear Infections with Existing Diagnostic Instruments 1. Overview As previously discussed, current otoscopes consist of a hand held device with a cone shaped extension called a speculum. In order to visualize the ear drum, the ear is pulled back and up in order to straighten the ear canal. In babies under 12 months, the ear may be pulled back and down as the canal is straighter in newborns. The tip of the speculum is then inserted into the ear canal to visualize the ear drum. Caution must be used to not insert the speculum too far as well as to avoid pressure of the tip against the walls of the ear canal. The speculum is moved and angled in order to direct the axis of the speculum toward the ear drum in order to get a straight view to the ear drum. Otoscopes usually have magnification to be able to view a close up of the ear drum, making alignment even more difficult as the field of view is limited. The otoscope is usually held with one hand with part of the hand resting against the head or cheek in order to stabilize the device, while the other hand is used to pull the ear to straighten the ear canal. Users need to practice and become skilled in order to view the ear drum. Skill is even more important to perform the task rapidly and as comfortably as possible, especially since the ear is more sensitive when an ear infection is present. Children are especially difficult to examine due to discomfort and fussiness, fear of devices and/or the doctor office, and often being uncooperative. Devices and speculums are unfamiliar and intimidating devices which are perceived as being threatening.

2. Ear Position and Speculum Position During an Examination.

Solid lines and dotted lines with arrows will be used in the figures to represent imaging instrument positions and general viewing directions.

FIG. 43 shows an otoscope in use with the speculum inserted into the ear canal. The position of the imaging instrument, in this case an otoscope and speculum, is indicated by the solid black line and the general viewing direction is indicated by the dotted line and arrow. FIGS. 44A, 44B, 45A, and 45B show cross sections of the ear and ear canal and positions/angles of a speculum inserted into the ear canal, and the position of a cone shaped speculum is represented by the solid black lines. FIG. 44A is a frontal section, showing the upward and then slightly downward curvature of the canal. FIG. 44B shows a horizontal cross section of the ear, showing the back and then forward curvature of the ear canal. These figures show an ear in a normal anatomic position. Speculums inserted into the ear canal are generally correctly oriented to view the ear drum with the ear in this position, especially with magnified devices. This is why the ear is pulled back and up to straighten the ear canal for examination. Both two-dimensional views should be considered to determine the proper position of an imaging instrument relative to the 3D structure of the ear canal and ear drum, and whether there is an unobstructed or obstructed path towards the ear drum.

FIGS. 45 A,B show the ear position, ear canal shape and position of a speculum when the ear is pulled back and up for an otoscopic examination. (For an infant, the ear may be pulled back or back and down due to the different shape of the ear canal as previously discussed.) With the ear pulled back and up, the tip of the speculum is usually angled forward and downward (anteriorly and inferiorly) in order to align with the axis of the ear canal and provide a view of the ear drum.

As discussed earlier, the angle of the speculum attached to the otoscope that the user holds must be controlled in order to view the ear drum. The large dashed lines show examples of variability of the speculum direction and position. Small variations from the desired position/angle may still allow an image of the ear drum to be captured but the user should achieve and maintain a position close to the desired angle (i.e. less variation than is shown by the dotted lines). The depth also needs to be controlled, so that the instrument is deep enough to acquire an adequate image and not so deep as to injure the ear drum or walls of the ear canal that are more sensitive closer to the ear canal. The side to side and up and down motion must also be controlled to limit the discomfort and potential injury by hitting the ear canal walls, especially with the tip of the device.

3. Visualizing the Throat with Existing Diagnostic Instruments and Techniques.

When a person opens his or her mouth wide, the features that are usually seen are the teeth, the tongue, the hard palate and part of the soft palate. The tongue usually blocks the view back into the throat (see FIGS. 47 A,B). In order to visualize the back of the throat and the tonsils, a health care professional or other observer, such as a parent, usually shines a light into the back of the mouth, usually while looking through a viewing instrument, and the subject opens his or her mouth and says "aah" (see FIG. 46). Sometimes this action lowers the tongue and elevates the soft palate and uvula enough to see the posterior pharyngeal wall (back of the throat) and the tonsils. However, it is often necessary to use a tongue depressor to push down on the tongue in order to see past it into the throat. In this case, proper positioning of the tongue depressor is important. It should be placed far enough back to depress that portion of the tongue that is blocking the view into the throat but not so far back that it causes a gag reflex. FIG. 48 shows a tongue depressor in use and a view of the throat and tonsils.

Having the tongue depressed is typically an uncomfortable experience. While it can often be performed routinely in older children and adults (although it is still unpleasant), younger children are often not cooperative, especially if they are sick or have a sore throat.

In addition, an inexperienced person may have difficulty depressing the tongue enough to see into the throat without causing a gag reflex, or worse, may induce injury to tissues while using the tongue depressor, especially if it is inserted all the way into the throat. An inexperienced person may also require more time and number of attempts to see into the throat, causing discomfort or distress to the subject.

III. Telehealth System: An Overview

The current invention overcomes, or at least greatly reduces, the problems associated with prior art diagnostic visualization methods. In various embodiments, the disclosed systems and methods include the ability to collect subject information at a plurality of times or conditions, whereby the information can be transmitted and/or otherwise accessed by the medical professional and used in the assessment of the subject's condition.

The various figures described herein depict a variety of telehealth and/or other systems for remote diagnosis of health concerns. It should be understood that, while these exemplary systems include many different elements, which will be described in the sections that follow, various other embodiments of such system(s) may also include additional or fewer elements, as desired by the user and contemplated by the present disclosure. Some of these simpler or more complex systems will be discussed later.

A. Introduction and Exemplary System

FIG. 1 shows an exemplary telehealth system in accordance with the invention. A consumer contacts a healthcare provider to request advice or diagnosis for a health ailment, for example using a video call. The consumer explains the problem and provides background health information. The consumer then uses a device to collect diagnostic information and send it to the provider. The provider may view this information live on a portion of the monitor or display screen while also seeing and communicating with the consumer on the remaining portion of the monitor or display screen. Information may be transmitted in a lower resolution than it is collected in depending on the data speeds available. Higher resolution data can still be collected and maintained on the user side and selected segments or the entire length of the video can be transmitted to the provider during or after the live transmission (see FIG. 2). The provider reviews the information and data and provides advice or a diagnosis which may include a request that the consumer comes into the doctor's office, a referral for the subject to see a different provider, or a prescription for medicine.

A system (see FIG. 3) typically consists of one or more of the following subsystems: 1) A user system, 2) a provider system and 3) a logistics and infrastructure system. For example, a user opens a software application on a communication device such as smartphone. This software establishes a link over the internet with an application server which enables the user to further establish a link through the internet with a provider whose information is stored in a database connected to the application server. The user's information and health records may also be obtained through the server. The user may then communicate with the provider who is using a device such as a tablet, smartphone, laptop or desktop computer. The provider may request additional diagnostic information, such as images of the user's ear drum. The user then captures these images with a diagnostic device which sends the information over the internet to the application server which stores the information and relays it to the provider. The user and provider may communicate via a video call and the provider may view the diagnostic information in real time and/or remotely control aspects of the diagnostic device (such as zooming, angling the camera, adjusting lighting, etc.).

B. Other Examples of Systems

A user may collect images or a video which is analyzed by software that provides advice or a diagnosis. This software may reside locally on the user's device, such as a smartphone, or remotely on a server. A virtual provider produced by the software may communicate with the user.

Multiple providers may be involved. For example, a provider may forward information to a specialist who then communicates with the user and provider. Alternatively, a specialist or other additional provider may join the communication between the primary provider and user, and all parties may view diagnostic information in real time.

A system may be used to monitor conditions and alert a user or provider if certain conditions exist. A user may collect this information periodically, or a device may continuously or periodically collect information without the user's input. The provider may then initiate contact with a user when notified of certain conditions.

A user may send information to friends, family or other users for input or advice. The information may be sent to a group of users or all users on a system who can then provide feedback. Such transmissions will be conducted in accordance with applicable regulations regarding sharing of medical information.

C. Communication Component and Remotely Linking One or More User(s) and/or Provider(s)

A telehealth system will preferably include a method to remotely link one or more parties through communication devices and enable voice, video and/or text communication. Alternatively, a system may employ communication devices to allow a user to record and/or upload video, voice, text, background health information and/or diagnostic information, and enable a provider to evaluate and provide a diagnosis or advice without live communication with the user.

The communication component(s) may take a variety of forms. For example, the user may communicate with a computer, a tablet, a landline phone, a standard mobile phone, a smart phone such as the APPLE IPHONE, a unique communication device specialized for use with a telehealth system, or any other device that allows recording, transmission and/or uploading of voice, video, text, files and/or diagnostic information. In various embodiments, the device will desirably allow receiving of similar information and enable the user to receive a diagnosis or advice from the provider. In one embodiment, the provider communication component is of similar design and capability. Although in other embodiments, the user and provider can have dissimilar communications devices and components which still communicate and allow for sharing of text/voice/data as may be applicable.

Desirably, the provider communication device will be able to receive information from the user and transmit a diagnosis or advice to the user. The user and/or provider may use more than one communication device concurrently or sequentially. For example, a user may use a landline phone to communicate by voice with a provider and use a computer to receive and transmit diagnostic information. While the device that transmits diagnostic information may also have (or may be) a communication device, it will also be described as a diagnostic processor, which may be separate from the communication device(s).

The link between the user and provider may be created using a variety of methods. A user(s) can initiate a telehealth session by submitting a request for care. This request may be directed to a specific provider (for example, the subject's primary care physician), a limited network of providers, or it may be "crowd-sourced" to any available provider, which may facilitate a more rapid response. In addition, the request may be routed to a nurse hotline or call center that may provide a preliminary evaluation and as necessary forward the connection to an appropriate provider, such as a doctor or medical practitioner.

A provider then accepts the request for care and, in various embodiments, a secure link between the user(s) and the provider(s) can be established. This link may be as simple as a phone call but more desirably includes a video link between the user(s) and provider(s). Also, as previously stated, the secure link may only involve the transmission of information (e.g. video, voice and/or diagnostic information) and not require "real time" live communication. The diagnostic information and/or other information such as a recorded voice and video transmission may be reviewed by a provider and/or software analysis tool offline from the user and a diagnosis or advice forwarded to the user.

D. Collecting and Transmitting Diagnostic Information and Relevant Medical History The provider(s) then collect and/or review the relevant health history from the user(s) and a description of the health issue that the user(s) requires help for. If some or all of this information is contained in the user's account or available for retrieval from a remote location, the user may elect to directly share this information with and/or authorize release of this stored data to the provider(s). In addition, it may be desirable for the user to share up-to-date (current) diagnostic information with the provider. This information may have been collected recently, over time, or during the call through the use of various home diagnostic devices. Examples of subject information can include blood pressure readings or blood glucose levels. These devices may provide the data only to the user, and the user can then share this data with the provider, or the devices can allow the data to be sent or shared directly with the provider through a communication channel. This diagnostic information may also be collected through the use of diagnostic devices described herein.

Ideally, the diagnostic device is connected to a communication channel which gives the provider one or more feeds of the diagnostic data and (when applicable) the ability to control or refine diagnostic feeds or download snapshots or segments to allow high resolution or more precise information to be viewed. Relevant health history information may also include information or data stored or otherwise obtained from the diagnostic device or a linked device, such as geographic location data from a smartphone GPS and/or credit card, payment information from an electronic wallet, etc.

The next step is for the provider to determine a diagnosis or give advice to the user. This may include an e-prescription (which may include directions to a local pharmacy identified using GPS geographic information from the user), scheduling a follow-up consultation and/or recommending the user proceed to a doctor's office, urgent care or emergency room (which may include directions to a local service provider based on the subject's location). The user and provider then agree that a sufficient resolution has been reached. A third party may be contacted to help reach a satisfactory outcome if there is disagreement on the resolution.

The final step of subject care under this exemplary system can involve termination of the consultation (e.g. provision of subject care instructions) and completion of logistics. This may include submission of an e-prescription for subject collection, processing of payment, electronic links to or emails containing the details or summary of the call, and/or creation and submission of insurance forms or other formal documentation.

E. Accounts, Logistics and Infrastructure

In various embodiments, it may be preferred that one or more user accounts of some type are created prior to the initiation of the communication. Desirably, a user account should contain sufficient information to verify that the subject or other responsible person is able to pay for access to a provider. This account may be anonymous in nature, containing as little as payment information only, or may contain detailed information on subject history and/or a link to a subject's Electronic Health Record (EHR). Desirably, the provider account should contain sufficient information to ensure his/her identity and expertise in order to provide the requested care. This account may be part of a larger account established and maintained by a physician group, an insurance company, or other similar responsible group.

F. Telehealth Systems and Additional Features

There are several types of systems and features which may be incorporated into a telehealth system. The telehealth system may be as simple as a phone call between a user and a provider, or include videoconferencing and live transmission of diagnostic data such as images being captured in real time by the user with a device. The system may also allow text and file sharing as well as links and updates to a subject's electronic health record (EHR). The provider may simply give advice or provide a formal diagnosis and submit an e-prescription. The system may also incorporate computer analysis of diagnostic data, for example, to give the user probabilities of certain conditions, or to provide a provider with a more thorough analysis.

Multiple types of connections will be described, including the ability to connect a caregiver at one location, a subject at a second location, and one or more providers on the same "call". The user may select specific physicians based on a ranking and pay appropriately, or offer a specific amount of money and wait for a provider to accept the fee. There may also be social/gaming/educational elements built into the system. For instance, users may wish to "crowd-source" their health issues for comments and advice from other users. Users may be offered discounts for achieving a certain level of accuracy in their feedback to other users. The system may include video-game type three-dimensional tours through or around the body with examples of health ailments and ways to prevent or treat these issues. Users may be given points and increase their status based on correct identification for exemplary health ailments.

IV. Components of Telehealth Systems

Several embodiments of devices, methods and systems which help facilitate the described telehealth system as well as simpler and more complex systems are described herein. It should be noted that that diagnostic embodiments may be used without a telehealth system, and that telehealth embodiments may be utilized without the use of diagnostic devices.

A. User Subsystem for Remote Monitoring and Diagnosis: An Overview

Devices, systems and methods of the invention will typically be described from the perspective of use by consumers but such aspects of the invention may also be used by providers. It is preferable that higher end devices and components, such as better lenses, higher intensity lighting, higher resolution video chips, more sensitive microphones, additional options for manipulating data (for example, modifying images and filtering sounds) are incorporated for use by providers. It is also preferable that devices allow for more fine control by a skilled provider with fewer limitations for placement and location. For example, a device may allow a provider to angle an extension in the ear canal to a greater extent and to place it deeper than a similar device intended for use by a consumer.

A user system (see FIG. 4) typically consists of one or more of the following components: 1) a communication component, 2) a component for accessing and/or capturing diagnostic data and 3) a component for processing diagnostic information. Many configurations of systems and these components, as well as other components and features, are possible. For example, a system can include one diagnostic device which contains all three components. Alternatively, a system can include 1) a diagnostic device which contains an accessing and capturing component and a component for partial processing of diagnostic data (for example, transmitting data to a smartphone or directly to a provider and/or recording data) along with 2) a computing device such as a smartphone which includes a communication component for voice, video or text communication with a provider as well as a component for processing diagnostic information (receiving from the diagnostic device and transmitting to a provider and/or analyzing data).

B. Communication Component

A communication component allows the user to connect with another party, such as other users or a provider, to share information, and to request and receive advice or diagnosis. Examples include a laptop, tablet, cellphone or smartphone and landline phone. Communication may occur by one or more methods, for example via text, voice or video.

C. Accessing and Capturing Component

The accessing and capturing component typically consists of one or more of the following: 1) an accessing element, 2) a capturing element, and 3) an anatomical interface. Accessing and capturing elements are collectively referred to as diagnostic elements and are used to access and capture diagnostic information.

1. Accessing Element

Accessing elements transfer diagnostic information to and from capturing elements and areas of the body. Access elements include inputs and outputs such as lenses that transmit light from a light source towards an object as well as lenses that collect light and channel it towards a video chip to capture the light. Access elements include any means to access, collect and transfer diagnostic information between an area of the body and a capturing element. These include open channels, reflective surfaces and mirrors, fiber optics, lenses, diaphragms and other means to collect and transfer energy including heat, sound, electricity, light, motion, and magnetic fields. Access elements may also be used for tissue or fluids of the body. Access elements may conform to an area of the body where the shape, texture or other characteristic is of interest.

2. Capturing Element

Capturing elements include elements which are used to create and/or capture diagnostic-related information. These include source elements, such as light sources and pressure sources, as well as destination elements such as video chips. For example, an LED uses electricity to produce light which can be transmitted towards an ear drum. This light is then absorbed or reflected back towards a lenses which focuses the light onto a video chip which translates the information into electricity to be processed (stored, recorded, output on screen etc.). A capturing element can also be a user's or provider's eye or ear, for example, for gathering light or sound which is then processed by the brain. Pressure transducers may be used to capture force in order to reproduce a tactile feel which is similar to nerve receptors on fingers.

3. Anatomical Interface

An anatomical interface may serve many purposes. In general, an anatomical interface contacts an area of the body to help facilitate accessing and capturing diagnostic information. For example, a feature may fit into or on the ear or ear canal to help align lenses in the ear canal so that the lenses transmit light towards the ear drum and collect it from the ear drum. A feature may also be used to help position anatomical structures so that diagnostic information is better captured, for example, by depressing the tongue for a view of the throat. Anatomical interfaces may also serve as accessing elements. For example, part of a diaphragm or a balloon in contact with the body can collect and transfer sound. The interface may also be used to conduct electricity to or from the body. Interfaces may also help with safety, tolerance and comfort.

D. Processing Component

The processing component includes elements which convert or process signals or transmit, receive, record, or output diagnostic information. For example, an image processor and wireless chip may be included in an ear bud for imaging the ear. After the signal is captured by a video chip, it is processed and wirelessly sent to a computing device such as a smartphone. This smartphone receives the information and records it, displays it on the screen, and sends it to a provider. Both the ear bud and the smartphone will typically have processing components.

V. Overview of Various User Devices and Systems

An anatomical interface is provided which serves as a guide for devices. For example, an ear bud may have a support surface or through hole to guide an existing otoscope and speculum.

Attachments or supplies are provided for existing instruments/devices. Examples of attachments are: a speculum with an anatomical interface, such as an ear bud molded onto it, that is attached to existing instruments; an ear bud may be separately formed and slipped onto or otherwise connected to a speculum; a curved or flexible speculum structured to fit onto a standard camera or smartphone; a flavored sleeve that is slipped over an oral scope for imaging the throat, or a soft sleeve that is placed over a tongue depressor or a semi rigid tongue depressor with a soft outside.

Diagnostic devices are wired to a small "box" which then processes diagnostic information. Multiple devices may be supplied which can attach to and be detached from the box. The box may send information to a computing device such as a smartphone or directly over the internet to a server. This box may be rigidly attached to some diagnostic devices (for example, with wireless contacts into an oral device) and connected by wire to other devices, such as a small ear bud for imaging the ear. Devices may also send information wireless to the box for further processing.

A single device may capture and process information. For example, an ear device may capture images from the ear and send the information directly over the internet to a server. Alternatively, the device may also send the information to a computing device, such as a smartphone, to output or record information, and to a local "box" to other wise process information, such as sending it directly over the internet to a server. The device may also have communication elements, such as a microphone and speaker. This device may link to a smartphone via BLUETOOTH for communication. Alternatively, the "box" may contain communication elements and serve as a standalone communication device or be linked to a smartphone which establishes the communication.

A device may have multiple diagnostic elements and anatomical interfaces built into it, so that it can be used to access and capture one or more types of diagnostic information at one or more locations of the body. The device may alternatively have processing elements and be supplied with attachments that have diagnostic elements, there may be a combination of the two. For example, a device can be supplied with multiple capturing elements such as a video chip and other sensors (such as MEMs, or microelectromechanical sensors). Some interfaces built into the device allow the use of some of the sensors to collect information from the body. Other attachments with anatomical interfaces help access additional diagnostic information at other locations. Still other attachments can be supplied with sensors to capture information and can also include anatomic interfaces.

VI. Communication Devices, Systems and Methods

A. Communication Component

Subject/caregiver communication devices can have any kind of structure, and can include devices which allow connection to a distant location, ideally allowing video, text, file sharing and/or other data connection. A plurality of communication devices can also be used in tandem. For example, one communication device may be used for video/voice communication, and a second communication device may be used as a channel to display and/or transmit diagnostic information to the medical services provider. Also, users may be more comfortable speaking over a landline telephone but can see the provider on their computer (a communication device) which also serves as the data diagnostic processing unit to transfer data to the medical services provider. Examples of communications devices are provided below, and they may be used alone or in combination with other communication devices, for example:

landline telephone, which can be used for a simple phone call or with a diagnostic device with wireless/wifi capability or other internet connection which connects to a conference call with, and feeds information to, the provider. A user can also use a landline phone with a computing device to provide video capability;

mobile telephone; computer and telephone; tablet and telephone; tablet only;

computer only (with a standalone diagnostic device as applicable);

supplied device specifically for communicating with this system. Such devices are ideally suited for the elderly and they may also serve as the diagnostic computer. The device may be connected cellularly or have an RF or other wireless transmission mode for connection to the Internet or to a base station connected to internet or wireless; and monitoring device or system set up in a bedroom having wide view or zoom capabilities, which may be initiated by a caregiver (e.g. for elderly subjects).

The system may comprise one or more cameras located in one or more rooms of the house. Users may be connected to these communication devices in a variety of ways. One method, especially useful in case of an urgent issue, is a push button device worn on the body (such as a watch, bracelet, or necklace).

Examples of a provider's communication device include:

telephone only (landline);

telephone and computing device for video or other data connection;

mobile phone only;

tablet only;

computer only;

video conference room; and simultaneous feeds to other providers for training or additional physician (e.g. a specialist).

A communication device preferably has software providing a user interface to facilitate communication, provide a user experience, transfer of diagnostic information, recording, output/display, and/or other features to aid in the telehealth service.

A communication device may also serve as a diagnostic processor (further described below). This device may output diagnostic information (e.g. display images) and transfer the diagnostic information to the provider. When used in this fashion, the device may switch from video/voice communication to a voice call only while collecting and transmitting diagnostic information.

B. Systems and Methods for Remote Linking of One or More Parties

A connection between the subject/caregiver and the provider(s) may include any of the following steps, which may be performed in any order:

1. Request connection time, for example, as soon as possible while waiting, request first available appointment, request appointment at specific time, or within a particular date or time window;
2. Select preferred provider (e.g. primary care physician);
3. Select preferred group (e.g. primary care and associates). Groups of medical practitioners may be available for selection, or a consumer may be able to select several individual physicians;
4. Select crowd source option, e.g., for instantaneous access, or for first to respond;
5. Select tier base of providers, wherein users pay more for higher credentials or higher ranked providers;
6. Select tiered approach for provider selection. For example, if the primary care physician is not available, the request for medical care will then pass to the next larger group after a predetermined time period, then to associates, then crowd-sourced;
7. Triage by an instant connection with a nurse hotline, and then routed to an appropriate provider (e.g., physician assistant, nurse practitioner, primary care, pediatrician, dermatologist, etc.);
8. Call center to answer and route call;
9. Emergency/distress request. This urgent request for assistance may be initiated with a panic button or a device worn on the body with a distress button. This button initiates a call and/or enables video devices in the area of the user. The button may also directly contact 911 services or other emergency response services. Upon initiation, the system may automatically collect data, download relevant information (e.g., GPS location information, current medical conditions such as diabetes, or current medication and prescription information) and/or maintain connection/control by remote user (e.g., medical personnel or police) throughout the entirety of the call to monitor the emergency situation and/or provide assistance.

Any of these options may be first initiated by a caregiver, and then the subject can be linked to the communication.

A connection between a caregiver and a subject may be received in any number of ways. For example, there may be a request from a subject to one or more caregivers. A request could be sent out to a single person, a few select people, or to many caregivers. Alternatively, there may be a request from a caregiver to a subject. The caregiver could open a video or communication connection without the need for the subject to "answer". For example, the caregiver can activate multi-room cameras or a camera in the bedroom or a bedside device.

C. User Interface and Software

A provider or other party can be provided with the ability to remotely select snapshots or a short segment of a video feed (or other type of diagnostic data such as sound) for high resolution download.

The user interface of the present invention allows for a simple and fast method of establishing a connection with a provider in the user's preferred method (e.g. crowd-sourced or only to primary care physician, etc., as discussed earlier). This software may be part of a standalone system, or the software may be provided as an interface for the user which links with third-party telehealth services. This option may be especially useful when the user's insurance company already has a contract with a telehealth service but the user (and optionally the insurance company as well) desires the use of diagnostic devices described herein. The user interface would establish the easiest and clearest way for the user to manage the call and diagnostic devices while still using the third-party telehealth system as the "backbone" of the communication.

VII. Features and Advantages of New Diagnostic Devices, Systems and Methods

The subsequent discussion focuses on the different techniques used to gather diagnostic information, such as imaging and sound, as well as devices that incorporate these methods and which interface with the human anatomy to allow reliable data capture; and connecting these devices to diagnostic processing components to transmit, output, record, and/or upload the data and techniques used to manipulate or remotely control the data and/or device for higher quality or more efficient viewing of data for a more accurate diagnosis. Diagnostic devices may be fully or partially composed of one or more features discussed in this section, including: 1) accessing and capturing components, 2) anatomical interfaces, and 3) diagnostic processing components. For example, a diagnostic device may incorporate a lens and fiber optics (accessing), which channel images to a video chip (capturing) which is encapsulated within a thermoplastic shape, which fits into the ear canal (anatomical interface) and attaches to a small external ear component which records images and sends the information via BLUETOOTH (diagnostic processing) to a smart phone for display, recording, and transfer to the internet (diagnostic processing). In this example, the smart phone may also be used as the communication component.

A. Overview

Devices, systems and methods are described which enable a user, especially an untrained consumer, to more easily capture health and diagnostic information; allow for safer use and provide a more tolerable and comfortable experience for the subject; enable or facilitate remote assessments or diagnoses; or perform data analysis to give a probability that a certain condition exists or help a provider determine the correct diagnosis. Features and methods are described which reduce or eliminate relative motion between the device and the body part being examined, reducing user error and making it easier to collect diagnostic information. Certain positions and angles and methods of achieving these positions are described which are advantageous for capturing desired data. Additionally, structures are described which position or align devices or elements into (or close to) these desired positions. Familiar structures that are used in a similar fashion as existing consumer devices (such as an earphone) are described which enable a user, especially a consumer with limited experience, to use the devices with limited or no training or practice. These and other features may also provide for safer use, better tolerability, and an overall more comfortable experience for the subject. A subject is more comfortable seeing a familiar device and knowing, at least generally, how it will be used and what to expect. Softer, conformable and better fitting structures also provide a more comfortable experience, as do features which stimulate other senses, for example, a speaker in a device for imaging the ear, or a pleasant tasting oral device warm/cool/cold oral or ear device. Other features prevent or reduce the likelihood of injury to the subject. Existing devices, such as a smartphone or tablet, may be positioned so that the subject sees what is happening, if he or she if so desires. This feature may be especially beneficial for a single user trying to capture images under the thigh or on the back with a device that transmits signals to a computing device, (such as a smartphone), for viewing.

These and other features help to empower consumers, making them more likely to address health ailments, and also to do so sooner than they might otherwise have. These devices, systems and methods may also be used by providers such as nurse and doctors. Although many features are described as serving a particular purpose, the features may have additional or alternative functions.

B. Anatomical Interfaces

Devices, including attachments, may be constructed with one or more components or features which are structured for contacting parts of the body, creating an interface between the device and the body. These interfaces can make it easier to use a device or provide for improved safety, tolerance or comfort. For instance, interfaces may provide support or stability and reduce relative motion between components and the subject; help to encourage or achieve preferred positions and angles for accessing and capturing diagnostic information; reduce potential for injuring tissues; or provide soft and/or conforming interfaces for comfort. Interfaces may position a device with diagnostic elements in a pre-ferred position or close to or within a window around preferred positions, thereby reducing the amount of user input or manipulation required to achieve a preferred posi-tion (a position capable of capturing desired diagnostic information). Interfaces may serve as locating features which help position a device at or close to a desired location or position prior to final positioning of other components or parts of the device, diagnostic elements, additional anatomic interfaces, or other accessing and capturing components. For example, an ear bud component with a through hole can be positioned in the ear prior to deploying an extension, attach-ment, or other part of the device through the ear bud into the ear canal. Similarly, an ear bud with a partially deployed extension may be positioned in the ear and ear canal respectively, which may then be in a position to capture diagnostic information or may require additional manipula-tion, extension or other positioning. Similar devices may be structured for capturing diagnostic information at other areas of the body, for example in the mouth, or oral cavity.

C. Usability

1. Positions and Angles

Preferred positions are positions and angles of the device, components and/or elements which enable the desired diag-nostic information to be captured. Several preferred posi-tions and angles will be described for components and elements which are involved in accessing and capturing diagnostic information. These positions may allow more relevant, accurate, reliable, easier, comfortable and/or safer collection of diagnostic data such as images, sounds and electrical signals. Methods of using devices and components as well as features of devices, components or elements help to access and/or encourage these positions. Preferred posi-tions may be achieved in a variety of ways. For example, with anatomical interfaces can help to position sections of a device, attachment, diagnostic element, in conjunction with the shapes of extensions or other sections of devices, (for example, as shown in FIGS. 17, 19, 99 and 101), attach-ments.

2. Support and Stability

Features may provide for anatomical interfaces which help achieve preferred positions and/or provide support or stability to the device or parts of the device. These interfaces may directly help to encourage a preferred position. For example, an oval feature can be shaped to fit into the entry of the ear canal with a smaller profile extension extending further into the ear canal. This extension may be offset and/or angled from the center axis of the oval part or may also be located in the center of the part and extend straight out (for example, see FIGS. 27 and 28). The oval feature may be part of the device, an attachment for the device, or a guide placed into the ear/ear canal prior to using a device. This guide may have a through hole, or part of the oval may be cut away so that an extension of a device with diagnostic elements, or another component for diagnosing conditions (such as a speculum), may slide through or past the guide and be encouraged into a preferred position. This oval (which can be part of the device, an attachment, or a separate guide), as well as other features described throughout, may serve other or multiple purposes, such as protecting the tissue in the ear canal walls from being injured or preventing over-insertion and injury to the ear drum.

An interface may also indirectly help a user to maneuver the device into a location that is capable of capturing the desired diagnostic information (a preferred position) by providing support to help stabilize the device, and reduce or eliminate the relative motion (up/down, side to side, in/out, rotation etc.) between the device and the ear or other body part. For example, a cheek pad or an over-the-ear retaining component similar to an ear phone may help to both support and stabilize a device. A stabilizing component can support all or part of the device weight.

Interfaces may both directly and indirectly encourage a preferred position. For example, an ear bud may be struc-tured to fit within the concha in a certain position to provide support and stability to the device and to have an extension extending at a certain position (from the center or offset from the center) or angle relative to the ear bud. Part of the ear bud may also be structured to fit into the ear canal. This interface may be thought of as a combination of structures, one fitting into the concha and one fitting into the ear canal.

The ear bud, with or without a part that fits into the ear canal (or other support structure such as a cheek pad) may be compressible or have a compressible member (such as a spring) joining it to other part(s) of the device to provide stability and support prior to the device being moved into a position to collect diagnostic information, thereby helping with both usability and tolerability of the apparatus. For example, an ear bud with a certain width may have a hole through which a small diameter extension or speculum may pass through. The ear bud is attached to the device, exten-sion or speculum at the side furthest from the ear canal. When the ear bud is placed into the concha, the extension or similar component is positioned at or near the entrance to the ear canal. When the device/extension is moved towards the ear, the ear bud compresses to less than the original width, allowing the extension or similar component to move further into the ear canal, and preferably into a more anatomically-suitable position.

Another example of an interface is a structure which fits fit into the oral cavity and has diagnostic elements for imaging the throat which are positioned at the end and near the top (posteriorly and superiorly). Preferably, the elements are angled slightly downward. This structure positions ele-ments away from and above the tongue in order to see towards the back of the throat and down and behind the tongue.

3. Variations of Anatomical Interfaces for Improved Usability

Other features or variations of anatomical interfaces may also be incorporated to facilitate positioning of the device, components or elements into a position capable of capturing desired diagnostic information (a preferred position), or otherwise make the device more usable. Examples included flexible or conformable anatomical interfaces, such as a small diameter flexible tube placed in the ear canal, which conform to the body or passageways into the body (such as the ear canal or oral cavity and tongue), angled elements, such as at the end or tip of extensions or attachments and/or combinations of multiple elements in different positions or placed at different angles. Sections or extensions may also be shaped or curved to help achieve preferred positions. Flexible or elastic structures, such as extensions, can be formed with a certain shape to help achieve preferred positions, and which can move to conform or partially conform to anatomy to also help achieve preferred positions. For example, such structures can contain a shape memory structure that helps the component return to the original shape when forces are removed. Examples of shape memory structures include wires or coils, for example, those made with a shape memory plastic, stainless steel, or nickel titanium (nitinol). Examples of shaped components which can also be structured to flex or bend and which can return to their original shape are shown in FIGS. 17, 19, 99 and 101. A device, component, or attachment may also have a portion which may be extended by the user, or it may have a hole through which a component is extended through, optionally requiring a compression force to be applied by the user in order to extend the element. For example, a spring mounted extension (for example, a speculum or a device which fits into the oral cavity) may be deployed by the user after positioning a device with an anatomical interface (for example, an ear bud with a through hole for the speculum or a mouth or oral piece with a through hole for a smaller extension to extend through) by pressing a button in. This extension may extend straight out or extend at an angle, possibly being placed at a position or in a configuration that would have been difficult to insert if the components were fixed relative to each other. This feature may also provide for increased tolerability and comfort by allowing rapid insertion, data capture, and retraction. Another feature which may allow positioning a device in a desired position or location is a camera mounted in, on or near a diagnostic accessing or capturing component/element. For example, a camera at the edge of or near an opening in a diaphragm for a stethoscope can allow a remote provider to guide the user in positioning the stethoscope or allow the provider to confirm the correct positioning of the stethoscope.

Another example of a feature to help improve usability is the addition of small screens or speakers on devices in order to see or hear the information that is being collected. A device may also have features which allow attaching it to an existing device, such as a smartphone or tablet, to which the information is being transferred and by which the information can be seen or heard. A device may also be tethered to the component which is close to the body and which collects the diagnostic information. For example, a small ear bud containing one or more video chips and LEDs is connected by a flexible wire, (which may be retractable,) to a separate component which houses the battery, electronics and wireless chip. This separate component may also incorporate a screen and/or be able to be secured to a smartphone or tablet to help view or listen to the diagnostic information being collected.

D. Safety, Tolerance and Comfort

1. Position and Depth Control to Reduce or Prevent Possibility of Injury

Features or components which control the position or depth can be used in order to help avoid sensitive areas or to reduce the likelihood of causing an injury. For example, a feature can provide for an anatomical interface to prevent the tip of a device from being forced into the side wall of an ear canal or into the ear drum. Alternatively, features can prevent over-insertion into the oral cavity and contact with the posterior (back) wall of the throat by being stopping against the outside of the mouth or against the teeth or gums.

2. Familiar or Benign Devices

Devices and components which are more familiar and/or benign looking to the user and subject can be used for an improved subject experience. Such components may reduce the anxiety and stress commonly induced by foreign-looking objects and instruments such as those typically found in a doctor's office. Examples of more familiar devices or components are structures which resemble an earphone or pacifier. An extension into the ear that is closer in form and shape to a cotton swab than a speculum is preferred. An extension into the mouth which resembles a pacifier, a popsicle, or other object commonly inserted into the mouth is preferred over an instrument which looks like a tongue depressor or endoscope.

3. Soft Outer Surfaces

Soft outer surfaces (such as urethane, silicone or thermoplastic elastomer) are preferred on components which contact the body, i.e. anatomical interfaces. These surfaces are preferably slightly compressible if room allows and any edges are contoured or rounded.

E. Portability and Modularity

The present invention allows for compact and modular devices. One or more features may be combined into a single device to perform one or more diagnostic procedures (i.e. capturing an image). This device may allow for attachments to perform additional diagnostic procedures or to improve the capturing of diagnostic information, for example, to create a safer, more accurate, or more comfortable device. Attachments may also be created for existing devices or attachments using described features. For example, a flexible optical extension coupled to a smartphone camera or an attachment for a speculum can be used to that help achieve a preferred position.

F. System, Functions and Processing

The device, alone or in combination with a separate processing unit (such as a smart phone, computer or tablet), may provide functions which allow easier or better capturing, processing and/or output, as well as storage, of diagnostic information. For example, lights may automatically be adjusted for intensity or angle, or can be turned on and off to capture a better image of the desired object or location. Lights with different wavelengths may be turned on or off to collect different types of diagnostic information. An image may automatically, or upon a user's (consumer, provider, etc.) request be enlarged and cropped to display the object or location of interest. This feature would make it easier to use a wide angle to capture an image and allow for a larger margin of error when using a device, while still showing a detailed image of the desired object or location. A user may be guided with images, video and/or sounds during placement or while adjusting the position of a device to help achieve a position to collect the desired diagnostic information. Sounds or images and video may be analyzed with software to autodiagnose conditions, give a probability that a certain condition exists, or help a provider determine the correct diagnosis.

G. Diagnostic Information

Various types of diagnostic information may be useful to help provide a provider give a diagnosis or medical advice to a user. For example, a user may be concerned that his or her child has an ear infection. The provider may desire images of the ear drum, body temperature, and medical history. In this case, a light sensor (e.g. CCD or CMOS video chip) may be used to image the ear drum. A standard thermometer or a device with a temperature sensor may be used to record the body temperature and transmit the data to the provider.

Another example of an illness where telehealth systems may be helpful is an upper respiratory infection. In this case, the provider may wish to know how the upper airway and/or oral cavity appears, as well as obtain lung sounds and heart rate. A device with a light sensor may be used to collect images from the upper airway and a device with a microphone may be used to listen to lung sounds as well as the heart rate. This information may then be transmitted live to a provider or uploaded for review at a separate time by a provider. The medical test data or diagnosis information may be stored locally by the user, by the medical practitioner, or by the medical care facility. The data may also be transmitted to a medical data storage location, or saved in the cloud as is known in the art.

Various other potential ailments may be evaluated. For example, images of the skin may be useful for diagnosing rashes, skin cancer or poison ivy. Images of the eye may be collected for eye problems such as red eye or foreign bodies. Images inside the nose may be useful for evaluating potential allergies or nasal infections. Sounds of the knee joint or other musculoskeletal areas may be recorded to help diagnosis arthritis or other ailments.

As will be discussed, a multitude of other data types (light, sound, electrical, temperature, strain, etc.) may be useful to examine an individual for an untold number of potential ailments.

H. Accessing and Capturing Diagnostic Data or Information

Capturing devices can include a data capturing element such as a microphone or light sensor (i.e. CMOS or CCD chip). Examples of capturing devices include commercially-available and standard off-the-shelf devices as well as specialty devices. Examples of standard devices are those which may readily purchased from vendors and include smart phones, tablets and computers. Specialty devices are devices built or supplied specifically for purposes of the invention as described herein or supplied by other vendors for purposes similar to that described herein. Examples of specialty devices include devices which are similar in form to a smart phone as well devices which are incorporated into an anatomical interface and/or processing unit, which will be described in further detail below. Examples include speakers incorporated into a belt, such as those which are similar in form to a heart rate monitor; and a video chip incorporated into an earphone device that is similar to an earbud or a device that includes an over ear retaining piece.

1. Imaging

Accessing and capturing light for displaying images can be a very useful diagnostic tool. Light is emitted by a light source (for example, a light bulb, flash, ambient, or LED) and then reflected or absorbed by the environment (for example, the atmosphere, skin, or mucous) prior to being captured, for example, using a film camera, CCD or CMOS chip. Lenses and similar components are considered herein as accessing elements. Light continues to be modified or transmitted until it hits the capturing/sensor element, for example, a CMOS or CCD chip. The light may be accessed, focused, and transmitted prior to reaching the capturing element by means of devices such as lenses, fibers, mirrors, and filters. The captured image may differ depending on the light source. For example, in the morning and evening, the ambient light from the sun is different and the scene viewed by an observer is different. Likewise, different LEDs or filters may be used to provide light of different wavelengths. Wavelengths outside of the visible spectrum may also be emitted, filtered or captured. For example, certain wavelengths may be useful in distinguishing whether there is biofilm present, which is indicative of an infection, or be absorbed or reflected differently when there is fluid behind the ear drum. Variations of these features and/or methods may be incorporated into a diagnostic device.

Light may be captured by any light capturing device at any location on the device, for example, near the end of the device, using a video chip (e.g. CMOS or CCD), or accessed at any location on the device, for example, by means such as lenses, fibers and/or mirrors and channeled to a light capturing element. Devices containing light capturing elements may take many forms. For example, light may be channeled to a light capturing element in an existing device such as a smart phone, tablet or computer. Light capturing elements may also be incorporated into specialty devices such as an earphone-type device or a specialty diagnostic instrument which may have a form factor similar to that of a smart phone. Light may be captured/accessed directly in from the end of the device, or capturing/accessing elements may be configured at an angle or to the side of the end of the device.

Multiple accessing and capturing elements may be incorporated into a device. For example, two or more fiber bundles may be configured so that their ends are at different angles or locations. These fibers then channel the light to one or more light capturing elements (e.g. CCD or CMOS chip). This configuration will allow different images to be seen. If the light is channeled to a single capturing element, two different images may be seen in the same display. Software may be used to alternate the display the desired portion of the image on the full screen. Alternatively, a mirror may rotate to alternate the displayed images from the two or more different fibers. If the fibers are positioned at left and right positions, the two images may be combined in order to create a 3-D image. If a single capturing element is used, software may be used to differentiate the images and then create the 3-D image. Alternatively, straight channels and/or channels and mirrors may be used to transmit the light to the light capturing element without the use of fibers. In other embodiments, light capturing elements may be located the end of the device and capture the light at that location, at multiple locations and/or multiple angles.

Light may be supplied in a variety of ways as well. Light may be emitted from a light source (e.g. LED) at the end of the device or light may be transmitted to the end of the device. For example, fibers, mirrors, or straight channels may be used to transmit the light to the desired output location. Various filters may be used to change the emitted wavelength, and more than one color or wavelength light source may be incorporated into a device. Filters may also be placed just in front of the capturing element and/or software used to modify the exposure so that certain wavelengths, brightnesses, or other types of image variables are modified or restricted from the image. Light may be output in a variety of geometric shapes or configurations as well. For instance, light may be output in a ring surrounding the video accessing and/or capturing elements; emitted from a single location adjacent to the accessing/capturing element(s); or emitted from a plurality of locations relative to the accessing/capturing elements.

Multiple accessing and capturing elements may be positioned to image different areas. For example, the user or practitioner may desire to see an image of the skin, throat, or ear while also seeing a more contextual image, such as how the device is being used and positioned. An example of one configuration is using one of the cameras of a smart-phone to capture an image of a child, and channeling light using fibers from the child's ear to the second camera on the smart phone. Imaging accessing and capturing elements may also be positioned to capture images in different locations of a desired target area, for example, in the oral cavity and then further away in the back of the throat. Imaging elements may also be located close to one another while still capturing images at different locations by having different focal lengths. This may be accomplished using lenses or other components, for example, software that can focus an image after capture in conjunction with a capturing element that identifies angles of captured light, e.g., using Lytro camera technology.

Various methods may be used to maintain a clear image. For example, air or water may be channeled to or away from the end of the device to maintain a clean and clear end of the accessing element (such as a lens), or air and water can be circulated around or behind the lens or other accessing or capturing element to prevent condensation or fogging. Anti-fogging fluid may also be applied to the device prior to use.

An accessing element may also be expandable. For example, a tube may be compressed for accessing a location and then expanded (for example, by inflation) to expand its diameter or size and thereby access a greater imaging area. Another example of an expandable device is one constructed of a central expandable member with accessing and/or capturing elements surrounding this member. When the central member is expanded, the surrounding elements are pushed out, accessing a larger area. Expandable members may also be used to change the position or angle of the accessing/capturing elements. For example, an expandable member may push the accessing/capturing elements up into the top of the oral cavity or to one side of an ear canal. Similar techniques may also be used for light sources.

Accessing and/or capturing elements may be configured for flexibility to allow conformance to a desired location (for example, an ear canal) and/or incorporate elements that allow the flexible elements to be manipulated. For example, a fiber bundle may be steered by a user in a fashion similar to endoscopes, or be remotely steered by a provider or other person. Alternatively, just the tip elements (such as a lens, mirror and/or light sensing chip) may be steered or manipulated Manipulation of the elements may include modification of the focal length.

Other imaging techniques may also be incorporated into diagnostic devices. One example includes ultrasonic imaging. Combinations of multiple imaging techniques are also with the scope of the present invention.

2. Detection of Sound

Sound can be detected using a diagnostic by any number of techniques. Sound may also be accessed and captured by a variety of methods. In contrast to light, sound may be captured through the air, or captured after being transmitted through fluids or tissue or devices. Microphones may be mounted on probes to record sounds when the probe is in contact with the body or when placed into cavities such as the mouth. These microphones may be placed at the tips of the probes or away from the tips, and they may record vibrations transmitted through the probes. Microphones may also be mounted on or in surface-mounted devices. Examples of these devices include pads placed on, attached to, wrapped around, or worn on a body part, such as a knee brace, belt, or vest. These devices may be designed to capture sounds such as those emitted by joints, the heart and/or the lungs or airway. Microphones located at or close to the surface of the device near tissue may capture more localized sound while microphones located deeper in devices and further from tissue may capture sounds from a larger area. Sound may also be accessed at a distance and channeled through one or more tube(s) to a microphone in a capturing unit.

Sound accessing elements may be "open", or natural, or constructed similar to a diaphragm. This diaphragm may be designed to conform to the desired area for a more thorough and reliable contact area, or to amplify the sounds or to collect sound from a broader area. The diaphragm may be similar in configuration to that of a stethoscope. It may attach to a capturing device with a microphone, such as a smart phone or a small unit with a microphone that transmits the sound, preferably wirelessly, to a diagnostic processing device such as a smart phone. Alternatively, the diaphragm and microphone may be incorporated into the same unit which attaches to a diagnostic processor which transmits the data, preferably wirelessly, to another diagnostic processing unit such as a smart phone which may output and/or store and/or send the data through the internet. This diaphragm, with or without microphone, may attach to the same diagnostic processor as the light accessing element.

Sound may also be filtered and/or amplified. For example, when using a diaphragm and stethoscope-type device, sounds related to heart and/or lung ailments may be filtered and amplified while other sounds may be filtered and discarded. This filtering may be done by the diagnostic processing unit or at the provider end and may be controlled by the provider. Also, microphones with different sensitivities may be used in order to collect a larger range of frequency of sounds and/or larger range of amplitudes. Once again, filters may then be used if desired or appropriate.

The invention also provides for a heart rate (HR) type belt or similar device (FIG. 32) which can be used to detect breathing sounds and to listen to the lungs as well as to check the heartbeat. For example, the capturing elements can include microphones for sound and sensors for electrical activity, as well as other sensors such as accelerometers which may be useful to capture motion (i.e. body movement or chest movement for breathing) while awake or asleep. Other examples of devices to detect sounds are a vest with microphones (FIG. 33); and a small interface similar in size to the end of a stethoscope which is attachable to a smart phone or other device with a microphone (FIGS. 31A,B) or containing a microphone and interfacing with an adapter to send the sounds to a computer. These devices may also contain various types of capturing elements (i.e. electrical sensors, accelerometers).

One or more of various types of microphones (capturing elements) can be contained in a stethoscope-type device or attachment to convert sound into an electric signal, for example, a dynamic, condenser or piezoelectric microphone. A typical diaphragm consists of a thin walled polymer with space behind it (i.e. similar to a balloon) or other structure that allows motion or transmits pressure changes, can be used to access sounds of the chest cavity or other areas of the body. These materials or diaphragms can also access and transmit electric signals, for example, when formed from or containing conducting materials or elements such attachments may also contain or connect to sensors, for example, in order to detect electrical signals of the heart. Diaphragms, a conforming polymer material, or other materials which access or capture electrical signals can be structured for application to various areas of the body, including the forehead, wrist and hand. Microphones may be set at a distance from the diaphragm, as may be preferred with a dynamic microphone, or in direct contact with a material or matrix of materials which includes the diaphragm or sound/pressure/movement accessing material. For example, a piezoelectric microphone may be mounted on a piece of rubber which is connected to a diaphragm.

Microphones may have different sensitivities when there is more than one microphone in a device or attachment. A camera may be positioned in a location to view the placement of the device (i.e. by the provider), for example in the center of the device or near the outside of the device. The diaphragm may be offset under a camera, structured to surround the camera, or multiple diaphragms or sections of a diaphragm can surround the camera. A light pointer can also be used to help with placing a device. For example, a focused beam of light can be emitted from the device to show where the device or diaphragm or other accessing component is facing. A provider may then direct the user to move or position the device as desired. Software may also be used to detect the position of this light beam (by analyzing the image viewing with a camera in the device or attachment) and to direct the user to the correct or desired location.

A doppler stethoscope attachment which both transmits and receives sound, such as case ultrasonic waves may also be supplied. A plurality of types of sound sensing techniques may be incorporated into a signal attachment and used at the same time or at different times. Alternatively, sound may be collected by an attachment and transferred, for example through open sound tubes or through vibrating material(s), to the main device which houses the capturing element(s). FIGS. 31, 38E, 86D, 87C, 88D and 102 show exemplary embodiments of various stethoscope attachments.

Certain embodiments of the invention provide for a method to detect internal sound by external diagnostic equipment. One goal of such embodiments is to give the practitioner or user a sense of what the subject feels, and such embodiments are particularly useful for orthopedics.

An example of a device having sound capture features is a brace for the back, knee or other area to pick up sounds (preferably internal) that may provide a diagnosis when used alone, or which provide reassurance when combined with other diagnostic data such as images. Similar methods and structures as discussed for stethoscopes can be used to pick up these other internal sounds of the body, such as the sounds of joints that are moving. Microphones located away from the surface of the body may also be used to pick up the external sound of joints.

3. Movement or Motion

Movement can be detected or captured using any kind of motion-detecting device. Examples of such devices are strain gages and accelerometers. Pressure in tubes can also be used to detect expansion/contraction, and pressure or sound changes in bags/compartments can be used to detect motion, for example, devices placed under a mattress. Such devices can also be placed around a subject's legs, knees, or other body part for detection of muscle or limb motion.

In certain embodiments, GPS units can be used to detect motion. External stereotactic devices, which devices track three or more points, can be mounted on various worn items;

or wrapped on or affixed to a subject's legs, vest, belt, or other part of the body or clothing.

4. Other Measurements

Muscle spasms or tension can be monitored to detect or diagnose conditions such as headaches which are often musculoskeletal.

Headband or bandage-type devices which contain strain gauges or other mechanisms can be used to detect motion and/or strain. Video cameras or motion sensors such as the Kinect device can also be used. Microelectricalmechanical (MEMS) sensors and devices worn on the body containing MEMS sensors (e.g., vest, belt, wraps, leggings, etc.) are also useful.

Reflexes can be detected or captured, for example, by determining a subject's quickness in pushing buttons or other responses. The responses can be tested in a gaming environment which can be hardware or software-based. Devices can also have a mechanism for hitting nerves or other tissue to elicit a reflex response. The diagnostic instrument may be integrated into a knee or elbow wrap or mount.

Subject health can be assessed using electrical-based diagnostic equipment to detect or diagnose conditions such as eye movement; hydration (resistance), and fat content (resistance), via electrooculography, electroretinograms, EEG, EKG, and/or EMG.

Temperature can be detected using various methodology, such as infrared, e.g. ear temperature or skin surface; or conductance; for example, using a standard thermometer. Relative temperature can also be used between different body surfaces or regions.

Touch and pressure can be sensed using gloves with pressure sensors to indicate how hard a subject is pressing on something. Such sensors may give a numerical or other scale feedback or provide a tactile output through device on the provider end. For example, a glove with pressure compartments may be modified to duplicate the pressures felt/recorded on the user end. Socks with pressure sensors can be used for gait, or for podiatrist assistance.

Other senses that can be measured include kinesthetics (relative position of body parts—e.g., a subject is asked to touch his or her nose with a finger with the eyes closed); or balance, magnetic/electrical fields, and pain.

The invention can also be used to measure or monitor standard diagnostics or vitals. That is, the invention can be used to obtain standard diagnostic information and vital signs such as pulse, oximetry, pulse oximetry, $CO_2$ blood levels, cardiac output (arterial pulse), heart rate, glucose monitoring, blood pressure, and weight.

Other tests or diagnostics that can be used with the invention include, for example, swabs or blood pin-pricks. Third party diagnostic devices and tests can also be incorporated through release of standard interfaces or programming information.

I. Moldable, Compressible and Conformable Components

Components may be compressible and conformable. For example, a foam exterior on a section that engages with the entrance of the ear canal may compress as it is being inserted. Or this section may be compressed and formed prior to placing into the ear in a similar fashion as foam ear plugs. The foam or other material may be constructed to slightly expand after insertion or it may generally retain the formed shaped. Components may be manufactured specifically for a subject. For example, pictures or scans (ideally 3D scans using technology such as MRI or light or products from companies such as Lantos Technologies) may be used in order to construct components (SLA, mold, 3D print).

Parts may also be bendable and/or conformable. Ideally, heat is applied to soften materials and allow a user to form a desired shape which is then generally maintained after the material(s) cool. Alternatively, a component may be structured with materials that allow plastic deformation, such as a piece of wire inside of a flexible material such as silicone, that bends under force and holds a general position while still allowing some flexibility. Components may extend and compress (for example the stem extending from an ear bud up and over an ear), for example a rod in a cylinder design, to conform to different users and anatomy. These components may also allow rotation and be formable or bendable.

J. Exemplary Methods of Diagnosis

Methods and types of diagnosis can be based on any combination of diagnostic information. There are numerous health ailments which may be diagnosed using any one of or a combination of the techniques discussed above. Below is a short list of examples.

1. Imaging of the ear drum for ear infections. Such diagnostic tests may also take an infrared temperature reading;
2. Listening to sounds of four quadrants or lung on the back of a subject. Such tests may help to diagnose asthma or a respiratory infection;
3. Imaging of the skin to detect skin cancer, rashes, poison ivy, or other such ailments;
4. Images of the mouth and throat for upper respiratory ailments/infections;
5. Epiglottitis by listening to sounds near trachea; and
6. Diagnosing flu and common cold, using data such as body temperature, images of the throat and listening to lungs.

K. Accessing and Capturing at Different Locations of the Body and Anatomical Interfaces for Diagnostic Devices Anatomical interfaces for diagnostic devices can have any shape or structure. Examples of devices with anatomical interfaces include otoscopes, rhinoscopes, and throat visualizers. While interfaces may be discussed in reference to a specific diagnostic technique and/or device, such as an otoscope for imaging the ear, similar anatomic interfaces and/or devices may be used to collect any type of diagnostic information. An example is an anatomical interface for the ear similar used to collect temperature information rather than imaging information. Anatomical interfaces may include elements to collect more than one type of diagnostic information. Non-limiting examples of such devices will now be discussed in further detail.

1. Ear

An otoscope may have features such as a flexible extension for easier insertion into the ear and for alignment to the ear drum and to conform to the ear canal. This extension may have a feature to prevent over-insertion or to limit the amount of force that is encountered. For example, the extension may be spring loaded and able to fully or partially retract depending on the forces encountered. This retraction, or force limiting mechanism, may be incorporated into a more rigid extension as well.

There may be a soft outer material on the extension for comfort during insertion and while imaging. These may also be more rigid internal material to maintain a desired shape. The extension may have a stop that interfaces with the subject to prevent over insertion into the ear canal. In one embodiment, the stop presses into outer ear and does not compress tissue into ear canal. There may also be hole to allow air to escape during insertion and imaging, or to prevent echoing or other bothersome noises.

The stop can be incorporated into a disposable sleeve, or it can have a shape similar to an earphone bud, or a cup around the ear. The diameter of the extension can also increase, thereby functioning as a stop in the ear canal. There may also be adjustable stops or different-sized sleeves to fit different ages.

Ear buds that snugly fit in the ear such as the Doc's Ear Plug, may have an extension into the ear canal. Over ear devices similar to ear phones can also serve as a stop or to provide alignment and/or to hold an imaging device in place.

A small bud or a bud with an over ear holder can have one or more small flexible wires connecting the bud to another device, or the bud may be self-contained and having RF, wifi, or other wireless communication link with a diagnostic computer and/or processor. Such devices allow significant motion and hands-free capturing of data, and such embodiments help with freeing up a user to manipulate the ear. There may also be an LED at the tip or channeled from the outer ear into the tip.

Other types of known diagnostic elements or components may be incorporated into an ear device instead of, or in addition to, lighting and imaging elements. For example, a device may contain an element(s) for capturing a subject's temperature, such as an infrared or resister sensor. A pressurizing component may be connected to or embedded within an ear device in order to apply pressure to the ear drum to see how well it moves. Speakers may be used to transmit sound in order to evaluate how well someone hears. Alternatively, sound may be used to comfort the subject while diagnostic information is collected. These diagnostic and other elements and components may be located in, on or near the device or attachments or in existing devices such as smart phones. Information may be channeled to sensors using a variety of means such as fiber optics or sound tubes.

Screw type or other adjustments can be used to change the length of insertion, and a balloon or other dilation method can be used to stop and hold the device in place.

Such devices fit into the ear and align the capturing and/or accessing elements. Ideally, the device will be able to image the ear drum with minimal or no manipulation of the ear. The capturing/accessing elements may be offset from the central axis of the ear canal and/or angled relative to the axis.

The extension into the inner ear may be formed of a polymer or other material. A lens can be in a central position, or it can be offset, and optionally offset posteriorly. This extension may dilate the canal if desired.

There may also be different attachments for the left and right ears, and such attachments may connect to a capturing device and channel images from the tip. A tip which rotates to fit into and align elements with left and right ear canal and ear drum is also possible and within the scope of the present invention.

Dilation of the ear canal is also possible by means of a balloon or other inflation device. This dilation may push imaging, light, or other channels outward for a larger viewing field and/or additional viewing angles.

Multiple attachments to fit different ear sizes or subject ages are possible and encompassed by the present invention. Such pieces may be very inexpensive and therefore disposable. There may also be moldable attachments for subject-specific fittings.

There may also be an extendable piece or longer extension fittings to see deeper in the ear canal for better clarity and/or to get past ear hairs. A head band, hat or similar retaining device can be used to help secure and hold the ear imaging device in place.

2. Nose

Many of the above features will also be useful in other anatomical interface embodiments.

For example, a rhinoscope may consist of a nose plug with various insert lengths and shapes, and a soft tip. There may be a soft outer material surrounding a more rigid inner material that maintains its shape. There may also be dual tips for both nostrils, which can be useful for imaging nasal cavities.

3. Oral Cavity and Throat

The invention also provides for an attachment to look into the throat. The attachment may consist of a narrower fiberscope when viewed from the side that more naturally conforms with the shape of the oral cavity, optionally with a mouth piece to depress the tongue and to open the oral cavity for better imaging. The mouth piece may be similar in shape to a pacifier. The attachment may also have a slight downward curve to depress the tongue and to provide a downward angle further back in the oral cavity to image the throat. Similar to a pacifier, the outer material of this oral device would preferably be soft and/or semi-compressible. The oral device may have any shape, and in one embodiment is oval in shape, as pacifiers generally are, to more naturally conform with the oral cavity. This oral device may be generally flexible in nature and bend with motions in an oral cavity should a subject, such as a child, resist to the device being used.

Devices and attachments may be structured with various diagnostic and/or processing elements. A device may be a standalone device for imaging the oral cavity or attachments supplied for existing instruments or devices or for devices contemplated in this disclosure. In addition, components are described which do not necessarily contain diagnostic or processing elements and can serve as sleeves or attachments for other devices or attachments, for example in order to provide a soft surface, position a device or anatomy or provide a taste or cooling effect to the oral cavity.

Oral devices with a softer outside material are preferred (for example urethane or silicone). These devices or attachments may also be compressible for even more comfort and contouring within the oral cavity, as well as safety, especially with rapid motion by a subject.

Devices are intimidating for children. Devices which are more familiar in feel and look would be more likely to be accepted. These may be sleeves to go around existing devices such as cylindrical endoscopes. One example of a preferred shape is a pacifier. For example, this can be a device that is wider than tall or a shape closer to a round ball that is soft and flexible. Ideally these devices would reach further back into the oral cavity than a typical pacifier and/or be shaped to better depress the tongue or otherwise expose more of the oral cavity and back of the throat.

One or more diagnostic element is typically contained in the oral interface, for example a light source and an image sensor. Multiple light sources, image sensors and/or other diagnostic elements may be contained and/or positioned by the oral interface and be located at various positions and angles. One preferred position for a light source and image sensor is displaced above and away from the tongue, and preferably pointing down and back into the throat. In this case, it is preferred that an anatomical interface for the oral cavity have some height, with the elements positioned near the top or superior part of the interface. The device could extend past this point, for example to depress the tongue beyond the position of the elements. In this case, it is preferred that the height is reduced in this section.

Additions to devices to make them more appealing and tolerable. Examples would be a flavored coating or a coating, fluid filled chamber or other material that may be chilled. The device or attachment may be structured to be able to be dipped into a flavored or chilled liquid. A sleeve that is flavored and/or chilled may be added to the device or attachment prior to use. Preferably the sleeve does not cover the imaging and light emitting elements.

4. Skin

The invention also provides for a dermatoscope, which can maintain a specific distance from the object to be imaged to enable measurements over time. A dermatoscope may incorporate an object of known size for reference in images obtained. For example, a feature located in or connected to an attachment for imaging the skin.

Devices or attachments can allow the camera to be at a set distance, or within a distance range, from the skin for a known or approximate magnification and size of the image. Attachments may be constructed with various configurations and combinations of access and/or capture elements. For example, attachments can contain a through hole to image through, one or more lenses to channel the light and image to a sensor in a device or a video chip to capture light. The attachments can have light sources or access elements that transfer light from the main device and can be open to outside light or partially or fully sealed off from the environment so that the light supplied for imaging is more consistent. Multiple lens systems and/or video chips can be used. For example, two different lens systems can be used which channel light to the same video chip, preferably to two different areas of the video chip, or to two different video chips. These lens systems can produce images with different magnifications, for example one image that is magnified and another image that is closer to actual size. One or more filters can be supplied which can be connected near or over the light outputs to allow different wavelengths of light to be emitted towards the skin. Filters can also be built into the attachment or the device. Different types of light sources can also be contained in the device or attachment to emit different wavelengths of light. Light sources can be selectively turned on or off, by the user, the provider or by software, to emit a chosen wavelength or range of wavelengths. Similar features can be incorporated into other types of devices or attachments for imaging other locations of the body. FIGS. 80A-80D show examples of configurations of anatomical interfaces and attachments to create devices for imaging the surface of the skin (dermatoscopes). The examples of configurations of anatomical interfaces and attachments may include spacers, shields, or stabilizers.

The invention also provides for a small probe inserted through the topmost layer(s) of the skin.

5. Other Locations of the Body and Corresponding Configurations

Devices and attachments with anatomical interfaces can be created for other areas of the body and various types of diagnostic information can be collected. For example, a device to collect sounds of the chest cavity, a device to capture images of the skin, devices to image the eye or position a device near the eye for a user to see screen, a device to image the nose or nasal cavity, more than one camera with the option to create a 3 dimensional image, infrared detectors for body temperature, light sources with various wavelengths and capturing chips designed to capture various wavelengths. The various features and anatomical interfaces may be used in a variety of structures, such as attachments for existing devices, attachments supplied as part of a kit that also contains a main device or in standalone devices.

The invention also provides for a probe which may be inserted into a body cavity (e.g., oral, stomach, intestines, etc.). Examination of the oral cavity may help with GERD diagnosis. The obtained data can be used to correlate sounds with specific ailments or to narrow down possibilities or identify potential issues.

The invention also provides for a device for measuring temperature, which may consist of an IR (infrared) detector built into an ear bud or similar device. The ear device may be held in place with a hat or head band. Alternatively, the temperature detector can be built into a head band or hat device with skin contact probes, and be optionally positioned on a subject's forehead area.

The invention also provides for a device for measuring oxygen saturation, for example, in the form of a finger or toe attachment.

The invention also provides for a device for measuring blood pressure, for example, for placement on a subject's wrist or arm.

The invention also provides for a device in the form of an eye piece (e.g. a cup-type shape) to provide safe imaging of eye and surrounding tissue.

Particular embodiments of capturing devices have a thin sleeve and/or covering that is disposable and which maintains a barrier as well as providing padding for comfort during a medical examination. There may also be stops to prevent over insertion (e.g., for an otoscope). Adhesive patches for skin mounted or contact devices can be used. The capturing device may also have a moldable interface.

The capturing device may also be integrated with a device to view, hear or otherwise observe or sense the diagnostic information. This may be a diagnostic processing unit as discussed later, or a simpler type interface such as an optical viewport to see the images through the diagnostic device. This device may or may not include components allowing storage or transfer of the diagnostic information. Such components may include software, mechanical elements, and/or other human interface to manipulate output.

L. Diagnostic Processing and Link to Diagnostic Device

The diagnostic processing components (sometimes referred to as diagnostic processors, or processors or processing components) allow for receiving, transmitting, outputting and/or recording diagnostic information and/or uploading the information to the internet. The information may be stored at a remote location if the information is being uploaded.

1. Diagnostic Processing Components

The diagnostic processing components may communicate with the diagnostic accessing and capturing components through a wired or wireless connection. Examples of wireless communication include RF (e.g. BLUETOOTH), wifi and/or wireless phone technology. An example of such a configuration includes a small wireless transmitter which attaches to and is wired to an image capturing device and transmits (preferably wirelessly) the data to a smart phone, tablet or other computer. This computer may then display the images, record the information and/or upload the information to the internet.

All processing components may be integrated into a single device, for example, a tablet, smart phone or other computer. An image accessing device with an anatomical interface is then positioned in front of the computer camera.

The computer is then able to capture, record, display and/or upload the information. This computer may also serve as the communication device.

2. Communications Link to Diagnostic Device

The accessing and/or capturing components may also be mechanically attached to the processing components. An example of this is a cradle with handle and a device with an anatomical interface housing a lens, video chip and RF transmitter, as well as other electronics. The cradle holds a tablet, smart phone or other computing device. The images are then sent (preferably wirelessly) from the device to the computing device in the cradle for displaying, recording and/or uploading. In another embodiment, a folder, portfolio, or carry case may hold a computer tablet on one side for communication and a smart phone or tablet on the other side to receive, record, display and/or upload the diagnostic information.

Part or all of the diagnostic processor may be the same as the communication device (e.g. laptop, tablet, smart phone) or other existing computer device (e.g. desktop, second communication device).

The diagnostic processor engages in wired or wireless communication to a diagnostic capturing device. The diagnostic processor may also serve as the diagnostic capturing device, for example, having an anatomical interface which attaches in front of a smartphone camera.

The diagnostic processing components may be built into the diagnostic capturing device. For example, a wireless transmitter may be attached and wired to a capturing device. The diagnostic information is uploaded directly to the internet and then may be downloaded to a communication device.

Alternatively, the diagnostic processing components may be located in another device, such as a base station. The base station can be located anywhere in the home or other facility, and is typically plugged in a power outlet and connected to the internet or a wireless service. This station communicates with and receives the information from the diagnostic capturing device. Information may then be transferred to a communication device and/or directly uploaded to the internet. If directly uploaded to the internet, the information may then be downloaded for display or other output in the communication device.

The diagnostic processing unit can also be a local "box" that communicates/connects to the diagnostic capturing device. The diagnostic capturing device may transmit the information wirelessly (e.g. RF) to the local box or be connected with a wire.

The local box may optionally be configured to display diagnostic information. This box may attach directly to the diagnostic capturing device, be hand held and allow moving and placing the diagnostic capturing device as desired.

Other forms include a watch or a flexible display that may be unfolded if applicable and placed in a convenient location. The local box or similar device is usually situated to be mechanically and/or electronically attached or linked to a communication device as previously discussed.

The device can also serve as a communication device, particularly if it has a display screen.

The local box may transmit information to a smart phone, tablet or other computer for outputting, recording and/or uploading the information.

Multiple devices and communication methods may be combined. For example, the diagnostic capturing device may have diagnostic processing components built in to record the information and/or display the information and also transfer the information to a local computer or communication device as well as directly transmit the information via the internet or wireless phone technology.

The local box or electronics may allow attachment to a multitude of diagnostic devices and be able to transmit the data to the internet, the communication device or other device as previously described.

The diagnostic processing components may also have a mechanical link for information transfer. The diagnostic accessing device may have a hollow tube for transmission of sound or fiber optics for transmission of images to a diagnostic processing device. The diagnostic processing device may have the hardware required to capture and process the information. Examples of hardware include a camera and/or microphone, and may include a cradle or other attachment to help align parts for adequate capturing of the diagnostic information.

The diagnostic processing component(s) may be able to communicate/connect to third party diagnostic devices as well. For example, a local box as previously described may communicate with heart rate monitors, pulse oximeter, scales, blood glucose monitors, etc.

Other features of a diagnostic processor and/or capturing device may include a conventional camera, a microphone, and/or a recorder. These elements may include a mechanical and/or electronic link between the anatomical interface and the camera or microphone to provide for transfer of the diagnostic information.

IX. Examples of Diagnostic Devices and Additional Features

Different devices which are created by combinations of disclosed features and components discussed in above sections can allow for accessing and capturing of data, an anatomical interface, and diagnostic processing.

A diagnostic device may have channels for secondary uses. For example, an otoscope for visualizing the ear drum may have a channel to allow air to be inserted into and pressurize the ear canal to visualize motion of the ear drum. Alternatively, additional diagnostic techniques which are not discussed herein may be incorporated into any diagnostic device.

A diagnostic device may have multiple diagnostic capturing elements. The diagnostic device may be held in place on the subject's body using any generally available or suitable means. For example, an otoscope may have an image capturing device and a temperature probe (such as an infrared thermometer). This ear device may be held in place with a head band, hat or similar retaining device. The temperature reading apparatus may also be positioned in the hat or head band rather than in the ear piece, and have skin contact probes which are ideally positioned near or on the forehead. Temperature readings may be recorded both within the ear and on the forehead to increase the likelihood of recording an accurate temperature.

Kits containing more than one type of diagnostic device and/or anatomical interface are provided by and encompassed by the present invention.

Diagnostic devices may have features to make them more comfortable and/or acceptable to the subject. Such features may include, but are not limited to a speaker in an ear piece (e.g. otoscope) playing soothing sounds or music that the subject finds enjoyable or vibration in a skin interface device (e.g. dermatoscope). An oral device or device to look into the throat (e.g. laryngoscope) may include a video screen situated in front of the subject to play videos for the subject and/or include a pleasant tasting mouth insert or the ability to apply a pleasant taste to the oral device or laryngoscope.

As illustrated and described herein, many devices are formed to be familiar to the user and therefore make them more comfortable and pleasant to use. For example, an ear imaging device with an earbud or over ear engagement member are similar in feel and use to headphones. The user may feel comfortable using such device and requires little or no instructions on using it. Similarly, an oral device for capturing diagnostic information, such as images, may be shaped in an oval form. This oval shape will more naturally conform to the mouth. The oval shape may resemble a pacifier or have another known shape. Users may feel more comfortable and safe using a device on themselves or their child since the device resembles a product they have used before. Further, devices are preferably constructed to resemble consumer products rather than medical devices to provide a more pleasant experience and also decrease the time and effort to learn how to use the device.

Other types of known diagnostic tools can be incorporated into a device or attachment. For example, an elastic hollow ball can be connected with a tube to a device or attachment to allow pneumatic otoscopy. The ball is squeezed to pressurize the ear canal or blow air at the ear drum in order to watch for movement. Ideally the air outlet is near the tip of a diagnostic extension or in an ear bud or in a section that engages with the entry of an ear canal or is otherwise located near or in the ear canal. The elastic ball or bulb can also be connected directly to a device or attachment so that an external tube is not required or just to secure and hold the bulb in place. It is preferred that the bulb is relatively small in this example. Another configuration of a pressurizing system is a main device with a small hollow chamber that has an external elastic cap or button which can be pressed to blow air towards the ear drum pressurize the ear canal.

X. Remote Control and/or Manipulation of Diagnostic Device and/or Diagnostic Information The invention can provide live feeds with the ability to request a snapshot or segment in higher resolution. The invention also permits low resolution viewing of large files such as MRIs, and the ability to request high quality images of select images or parts of images.

In certain embodiments, the invention can pull information from electronic health records and/or a central location of stored information. Such data files can be reviewed in low resolution and then selected files or portions of files can be retrieved for high resolution download.

The invention also provides the ability to modify device settings, such as filtering of sounds, zooming cameras, selecting which angle view is best, changing filters of images, increasing/decreasing electrical power, changing light source, selecting a camera, or modification of any other option previously discussed. There is also the ability of remote monitoring and/or control of a user device.

There may also be controlled articulation of a device, to change an angle or other shape to help navigate or align an instrument, or to change a tip angle or angle of elements such as a mirror or video chip.

XI. Accounts, Logistics and Infrastructure

A. Examples of User and Provider Account(s)

Several kinds of user accounts and provider accounts are possible in accordance with the principles of the present invention. There may be an anonymous account, in which billing and personal information is processed by a company or service, or a third-party service or telehealth service, or by the company described within), but the provider does not know the subject's identity and health records are not updated. This option allows advice only, and no prescriptions.

There may also be a basic account with consumer identification. Basic health information/background is collected during call, similar to a visit to a pharmacy clinic.

There may also be a basic account with past medical history completed for use with this system. Certain information, for example, a simple health questionnaire, remains separate from other subject records.

There may also be an account which provides for integration with the subject's existing Electronic Health Records (EHRs). Such accounts may pull out a subset of basic health information only for purposes of use in conjunction with the current sick call to keep the majority of the information private. The subject or caregiver decides what kind of information or which categories of health information is shared. This sharing could be done for each sick call.

Shared information may optionally be linked to a third party EHR. An EHR can be managed within this system. Health information can also be sent as required to update the subject's record(s) and pulled from other records as necessary.

Accounts can be created by the user, the user's health insurance, employer, family member, or another interested party.

An account can be created with health insurance information, or the account can be completely private and provide for separate billing via a self-pay model.

Subject accounts will be determined in accordance with particular implementations of the invention. Such accounts are envisioned to be fully HIPPA compliant, and the consumer controls and chooses what information is shared and with whom. Permission from the subject may be transmitted with any medical data and/or via a separate/independent transmission method or file.

Provider account(s) may include call records maintained (e.g. user satisfaction), and provider credentials.

Completion of Communication

Both parties may first need to agree that an acceptable resolution has been reached prior to completing the call as well as agree to which information may be stored prior to the uploading and sharing of information to an EHR or updating of any other record.

Billing and Insurance

The invention is amenable to different kinds of billing and insurance modes. For example, there may be a self-pay mode, or the user or provider can bill an insurance company and generate the relevant forms.

Communication Security and Methods of Transferring Information

The invention can use existing technology/company/software such as Vidyo, or such technology can be created from the ground up in-house.

B. Recording of Information

The invention can provide for multiple record storage options. For example, the invention can record entire communications and all imaging/collection of diagnostic information, or the invention can record only short segments or snapshots of diagnostic information selected by the provider and the final diagnosis and/or advice given. Alternatively, the invention can store only a form containing health history and a written diagnosis by the provider, with or without images. Prior to providing or receiving any service, the subject/consumer and health care provider can agree on completed review and storage of information.

C. Database Management

Database management for a particular implementation of the invention will generally be conducted in accordance with industry practices and regulations.

D. Interfacing with 3rd Party Software and Hardware Including Electronic Medical Records (EMRs) and Diagnostic Devices The invention can also interface with third party software and hardware providers, including those providing or storing Electronic Medical Records (EMRs) and diagnostic devices.

XII. Telehealth Systems and Features

Telehealth systems in accordance with the present invention permit the linking of two or more parties at remote locations to aid with or monitor medical conditions. The connections may be in the form of a voice call, video call and/or text communication or any of these with the addition of sharing information such as photos, files and/or diagnostic information, collected previously and/or collected during communication.

Communication methods may include cellular/mobile telephone, through the internet, via satellite, landline or any other technology enabling communication protocol.

Telehealth systems utilize diagnostic or health information collected with a variety of methods or available from previous health consultations. A third party device or a diagnostic device described herein, or other information such as x-rays, MRIs, blood tests or information contained in an electronic health record can be utilized.

Telehealth system in accordance with the invention may involve an official diagnosis, e-prescriptions, billing (individual and/or insurance), creation of insurance forms and/or updating EHRs.

Such systems also use software and/or user interfaces to facilitate capture, output (e.g. display or sound), transfer and/or recording of information.

Infrastructure, including servers and databases, can be purchased commercially or custom-designed, depending on the implementation of the invention.

Health care providers such as physicians or other professionals may be ranked by education, experience, user satisfaction or other means by which a user may wish to select a provider. Users or insurance companies may pay different amounts depending on the rank of the provider, or based upon prior negotiation.

Certain embodiments of the invention may be desirable for use in a gaming, social, or educational setting. For example, the invention can provide a 3D tour through the body and participants would guess medical solutions or diagnoses based on real data or examples for each location/area of the body. Users may get points and compete against others.

There may also be crowd-sourcing to other users for opinions without provider input. Users may compete against each other and be ranked for knowledge which may help in the probability of obtaining correct advice from the crowd.

The invention can also use real data for educational purposes with an interactive interface, e.g., a 3D tour through the body. The invention can also include demonstrations and illustrations of how a health ailment may have been caused and how to prevent or treat that condition.

Certain embodiments of the invention can be used for auto detection of ailments, for example, ear infections and progression of moles, and the invention can give the probability that the subject has the illness with or without an additional provider consultation. Software and analysis can be done on the user device and/or as a "cloud" service.

There may also be crowd sourcing for two or more opinions from providers. Such embodiments may be particularly applicable to lower income countries or those having lower provider cost (such as India) and for easily-diagnosed ailments requiring only an image or similarly simple sharing of diagnostic information. This would give a potential for extremely short provider review times, potentially in just 10 seconds.

The invention can also be used to solicit bids from providers for consultations, surgery or other care. A user may also offer a set amount for diagnosis and treatment, and providers may choose to accept the user's offer or not.

The invention can also be integrated with outside diagnostics facilities, for example, for lab tests or culture testing; to enable users to send samples such as blood, mucous, and skin shavings for analysis; and to schedule appointments for blood draws/testing or imaging tests such as x-ray or MRI.

Contacts between subjects/caregivers and medical care providers can be in any form, such as the following:

1. Direct peer to peer or through central server/gate or simultaneously peer to peer and to central location;
2. Caregiver and subject;
3. Subject and provider (or nurse/call center for routing if necessary);
4. Subject, caregiver to provider(s);
5. Caregiver to provider and separately to subject;
6. Subject separately to caregiver and provider; and
7. Any of the above with a facilitator such as a nurse or other trained individual at a call center.

A non-limiting list of examples of sick calls or requests for medical services can include requests for second opinions; treatment of acute ailments; treatment of chronic ailments; requests for follow-up appointments; scheduling physical therapy; monitoring, which can be initiated by caregiver and not require an active answer by the subject; fitness or wellness visits; and emergency and other urgent medical calls.

The invention can be provided to consumers in numerous ways, such as by health insurance companies, employers, through partnerships with health IT companies, or directly to consumers.

Different kinds of systems are possible within the scope of the present invention. For example, there may be a basic system, which provides telemedicine with at least voice capability and optionally video capability to enable remote diagnosis and prescriptions as necessary. There may also be diagnostic device services, in which the invention provides the ability to capture and send medical data and information from a subject to a health care provider. The systems may also have the ability to transfer a live feed of diagnostic information from the subject to the provider, or the ability for the provider to select snapshots or short segment video to download in high resolution from the diagnostic device.

There may also be a hardware or software interface to allow connection of any diagnostic device, e.g. for example, from a third party. These connections can be live feeds or collected over time such as blood glucose or heart rate and input by user, for example, by typing blood pressure readings into a diagnostic device. For live feeds, in one embodiment, the invention allows for recordal of information and data, and for remote transfer of high quality images.

XIII. Systems with Therapeutic Elements

The invention may also be in communications with medical devices which provide remote therapeutic elements or services to a subject. Examples of such devices are massage devices or muscle or nerve stimulation devices. The medical provider can send remote instructions to these devices so that the subject can obtain therapeutic treatment.

As described herein, various embodiments of the disclosed systems and methods significantly improve efficiency for subjects, clinicians, health system managers, and third party payers. The stored subject information allows reviewing clinicians to see the subject examination and glean valuable information that a previous clinician might have missed during a routine examination. Moreover, multiple clinicians and/or specialists can access the subject information simultaneously and/or sequentially, allowing additional reviews to review the data and reduce the chance of something being missed or overlooked.

The system can include features that allow consultants to review the comments and recommendations of other clinicians. In doing so, consultants may be exposed to the thoughts of other clinicians, which in turn can broaden or focus the clinical impressions more accurately, and again reduce the chances of error or misdiagnosis. Such review will normally be done within the data sharing permissions set by the subject, as well as within the scope of medical record sharing laws and regulations.

Various features of the disclosed system may encourage subject participation and involvement. The subject has opportunity to see his or her case, actively monitor the progression and assessment of the information by medical professionals, and review the various comments and recommendations and actively participate in his/her case. This may result in a more informed and involved subject, and can significantly increase subject satisfaction with the medical care and response.

In various embodiments, the user's initial subject information and treatment request creates a query that becomes available to the medical professionals (e.g., consulting clinicians) via a secure web portal or other format. The system provides the medical professional with the relevant subject data to be used in providing recommendations regarding the subject condition, assessment and/or treatment. The medical professional can review the query on-line at any time after it has been posted and can record his/her observations and recommendations into the query file as necessary and/or desired. Depending upon the subject condition and/or complexity, an initial assessment can be rapidly completed, for example, in 15 minutes or less, by properly trained personnel such as nurses, initial assessment technicians, or first responders. Such initial assessment may take significantly less time than needed for a clinician to evaluate the subject in person. For subjects requiring further in-depth assessment and/or analysis, their queries may be forwarded to a relevant specialist, while less complex queries can be addressed and responded to by a wide variety of less-expensive clinical specialists. This can significantly reduce the costs incurred to evaluate the subject, which may result in significantly lower costs for the subject and/or payor. In addition, the subject does not need to directly meet with clinicians individually, which may significantly increase the convenience and accessibility of healthcare.

Various features of the disclosed systems and methods may further facilitate the collection and recordation of subject demographics, medical histories, complaints, illness histories, height, weight, identification (e.g., fingerprints, facial photographs, DNA or blood type information), subject statements, video exam sequences, and physical characteristics such as physical inspection results, thermal imaging, palpation, strength, sensation and reflexes. In addition, various information relevant to the complaint can include links to electronic medical records, links to imaging databases, various clinical comments, and billing information. Subjects can give permission for the attending clinician to access their stored health records. The clinician can provide the most rapid physical examination if a subject's records are all available electronically. Nevertheless, the invention can also be highly effective to start developing a subject's electronic health record.

Use of the various systems and methods disclosed herein may be of interest to health systems administrators as it may facilitate a hospital or clinician group's expansion of their service area, attract subjects to their treatment facilities, promote utilization of participating providers, create multiple revenue streams, and may be a powerful marketing tool. In various embodiments, the systems add efficiency and increase clinical productivity.

In various embodiments, researchers may utilize various database information which may include data mining features, standardization of examination methods, and an objective documentation format. Similarly, health care professionals and/or educators may utilize various features that provide a rich educational format that can be accessed by students seeking to gain knowledge regarding the evaluation and management of health issues. The subject information files may be archived and used to provide exposure to a wide variety of cases and demonstrate various pathologies to students who might otherwise go years before seeing an example of certain variant conditions. In various embodiments, a multidisciplinary consultation feature can be provided that allows exposure of subject information to a variety of medical perspectives. Such data sharing will normally be used in accordance with local privacy laws.

Various features of disclosed embodiments offer significant direct cost savings, which may be realized when an emergency room or full office visit consultation is avoided because the information is available via the system. The system saves time because the subject does not have to wait to attend a variety of appointments and each clinician (if multiple medical professionals are required or desired) can view the subject information remotely on his or her own time. In addition, multiple consultations and opinions can be collected via the system simultaneously.

Advantageously, the system can increase quality by making multiple opinions available to the subject, which can increase subject responsibility and autonomy and facilitate greater levels of involvement in subjects' own health care. In various embodiments, subjects may be given the option of selecting a desired clinician or clinical specialty that they would like to consult on their subject information. The subject can directly review the various opinions and recommendations collected in the system and make their own choices about how they would like to proceed. Subjects can increase their understanding and knowledge of their condition by allowing them (or anyone else they so choose) to view their personal examination compilation in detail. In addition, the system allows third party payers to have a more complete and accurate assessment of the claimant's examination compilation.

V. Discussion of Figures

The present invention will now be described with reference to the Figures, wherein like reference numerals refer to like elements.

FIGS. 1 and 2 illustrate exemplary embodiments of a telehealth system in use in accordance with an aspect of the present invention. FIG. 1 illustrates a caregiver and a health care provider engaged in a video call, thereby interacting in two-way video and voice communications. A diagnostic device in accordance with the present invention has been inserted in to the subject's ear, and the diagnostic device acquires medical status data, including diagnostic images, and provides this information to the provider. During the video call, the provider can request that the caregiver or subject provide additional medical information or adjust the settings or placement of the diagnostic device. Although the figure shows the caregiver using a laptop computer and the provider using a desktop computer, the caregiver and provider can use other kinds of computer systems, such as the illustrated smartphone or tablet computer. In certain embodiments of the invention, caregivers and/or providers will install an application or an app on their devices to communicate. In view of current U.S. federal privacy laws, it is expected that all communications between a provider and subject/caregiver will be done over a secure electronic connection.

FIG. 2 illustrates an exemplary embodiment of the invention which provides for a plurality of data feed options to the provider from the diagnostic device. In the illustrated embodiment, the provider can choose to receive one or more high-resolution images via download, or the provider can receive a low-resolution live feed. The provider has the ability to manipulate the diagnostic information and/or the device by a remote control feature. In this specific Figure, the diagnostic data can be fed live to the provider at low resolution for seamless transfer and communication. The provider may select segments or snapshots of the diagnostic feed which will be downloaded to him or her at a higher resolution. The full stream of higher resolution data can be stored on the user's device and/or at a central location, and accessed by the provider for high resolution snapshots/segments or for later review. The provider may use the remote control feature for other actions, such as but not limited to focusing the image, controlling tip deflection or the direction of an imaging device, and filtering sounds.

Figure 3:
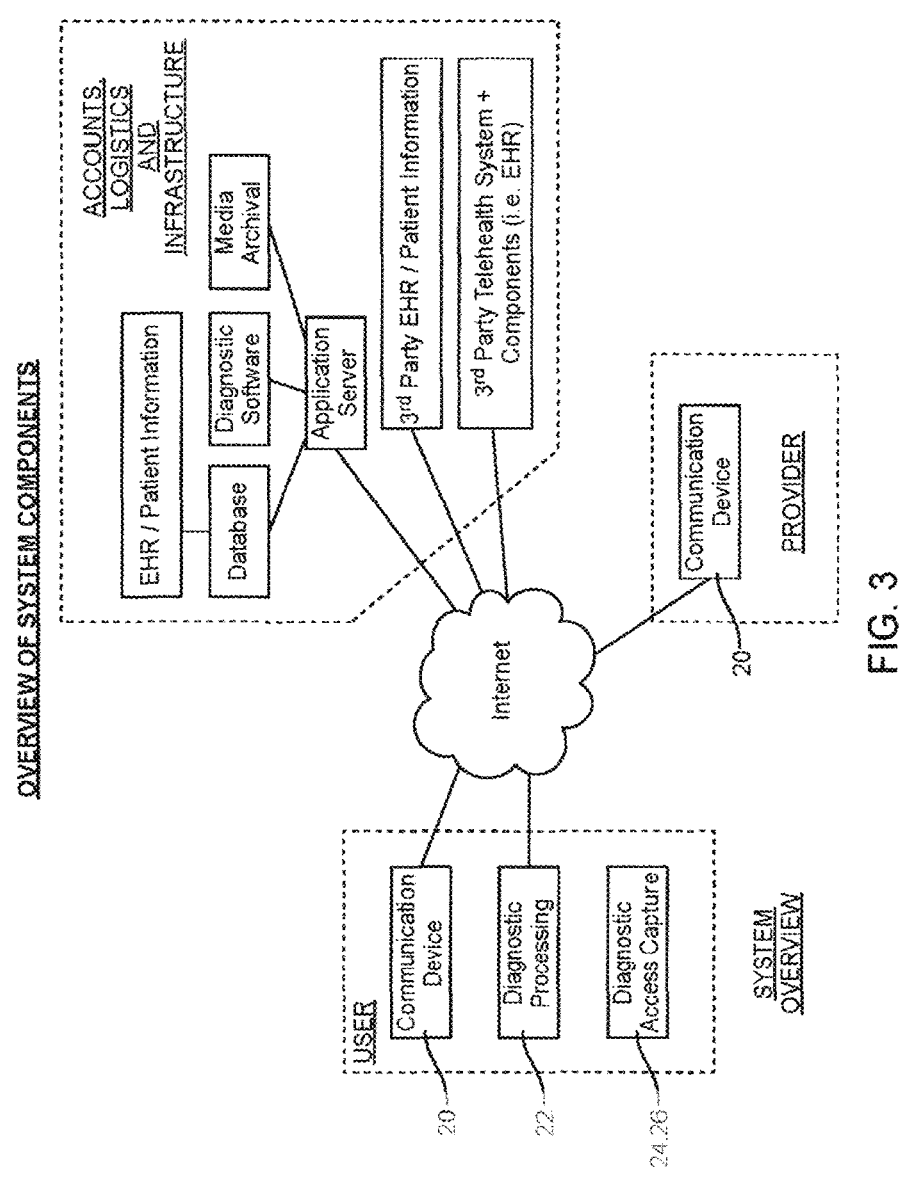
FIG. 3 illustrates linked components of an exemplary embodiment of a telehealth system.

FIG. 3 illustrates linked components of an exemplary embodiment of a telehealth system according to the present invention. The system is comprised of three components: (a) a user subsystem configured for receiving a subject's current medical data; (b) a provider subsystem configured for communicating with a health care provider; and (c) an infrastructure subsystem configured to process and store medical data and diagnostic information received from the user subsystem and the provider subsystem.

In the illustrated embodiment, the user subsystem comprises a communication device; a diagnostic processing device; and a diagnostic capture device. The provider subsystem comprises a communication device. The infrastructure subsystem comprises: (a) an application server comprising computer instruction code configured for communication with (i) a database configured to store a subject's personal information and electronic health record as well as information on providers; (ii) diagnostic computer instruction code configured to receive current subject medical information and to provide diagnostic information concerning the subject's medical condition; and (iii) a database configured to store archived diagnostic information; (b) a server comprising computer instruction code configured to communicate with one or more third-party subject personal information or electronic health record databases; and (c) a server comprising computer instruction code configured to communicate with a third party telehealth system.

Figure 4:
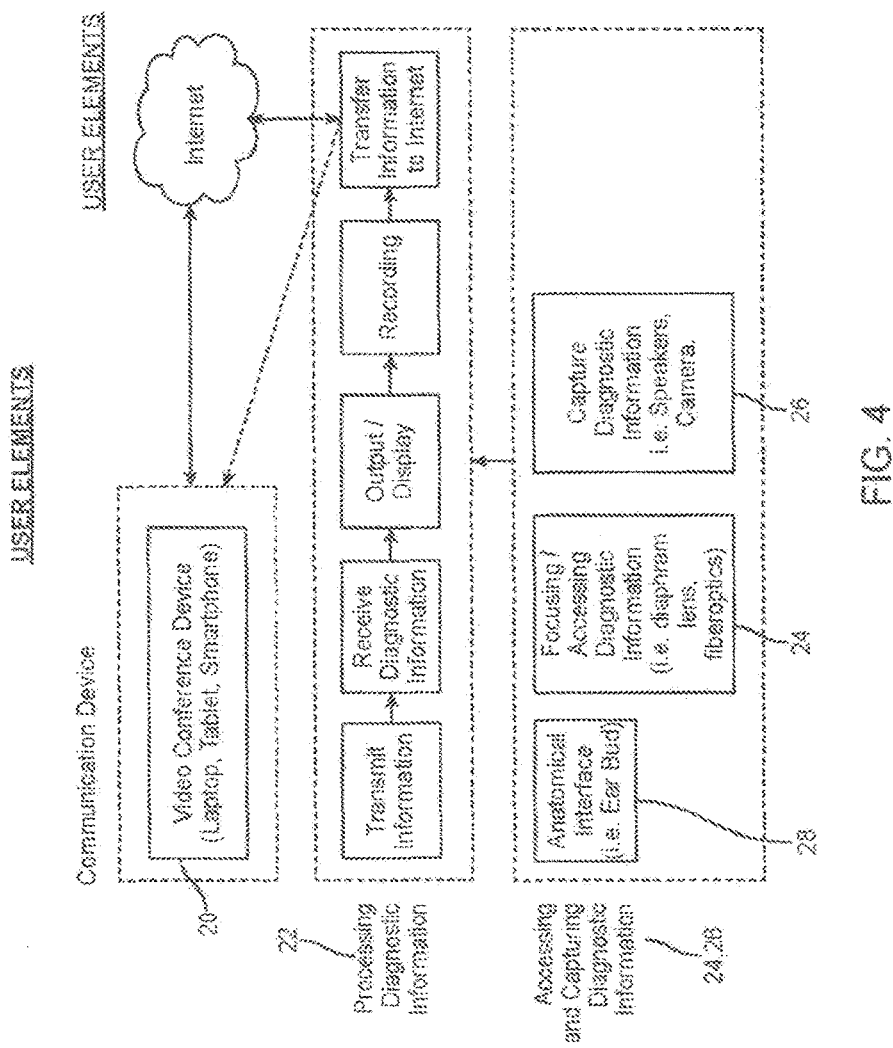
FIG. 4 illustrates three components of a telehealth system in accordance with an exemplary embodiment of the invention.

FIG. 4 illustrates three components of a user subsystem of a telehealth system in accordance with an exemplary embodiment of the invention. The user subsystem comprises a communication device, which can be capable of participating in a video conference. For example, the communication device can be a laptop, tablet, or smartphone equipped with a video camera.

The user subsystem also comprises a module which processed diagnostic information. This system transmits information, receives diagnostic information, outputs or displays information, records any diagnostic data, and transfers this information to the Internet, for example, to a storage unit which may be cloud-based or stored or warehoused on a proprietary site and/or to the communication device.

The user subsystem also comprises a module which accesses and captures diagnostic information. This module can comprise an anatomical interface, such as an earbud, and can focus and access diagnostic information via a diaphragm, lens, fiberoptics, or other element. This module can also capture diagnostic information via speakers or a camera.

Figures 5, 6, 7:
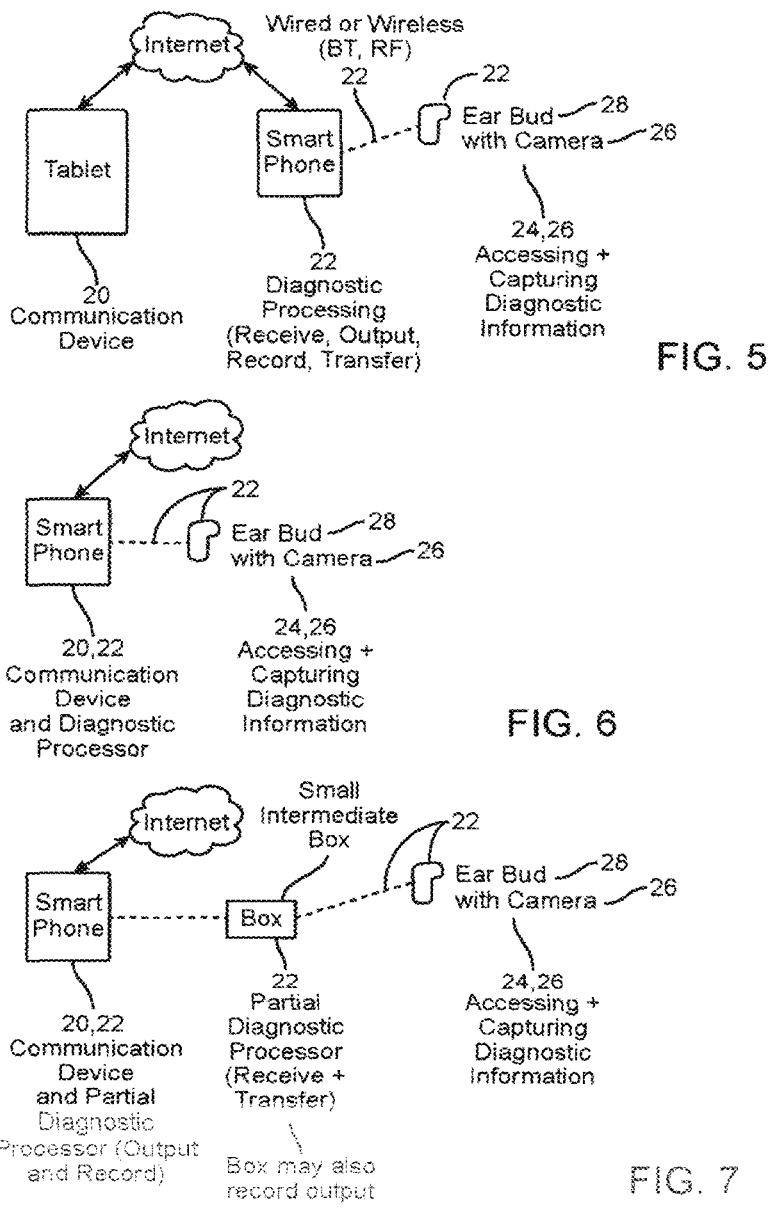
FIGS. 5-7 illustrate exemplary embodiments of user devices which are structurally configured for insertion into the human ear and which communicate a subject's current medical status in accordance with the present invention.

FIGS. 5-7 illustrate exemplary embodiments of user devices structurally configured for insertion into the human ear which communicate a subject's current medical status in accordance with the present invention. The user devices can include various kinds of communications devices, which may not have any diagnostic capabilities (as shown in FIG. 5), or which can have a diagnostic processor (as shown in FIG. 6), or which can have a partial diagnostic processor (as shown in FIG. 7). In these Figures, an ear bud having a camera is used to access and capture diagnostic information, and the ear bud communicates directly with a smartphone (FIGS. 5 and 6), or indirectly through a small intermediate box which has a partial diagnostic processor for receipt and transfer of information (FIG. 7). The earbud transmits photos of the inside of the ear canal wirelessly via BlueTooth (BT) or radio frequency (RF), although in certain embodiments this information can be transmitted via a wire connected to the jack or port of the tablet, smartphone, or other device.

FIGS. 8 and 9 show a cross-section of the ear region of a subject's head for purposes of reference.

FIGS. 10-20 illustrate exemplary embodiments of an ear imaging device comprising an anatomical interface to facilitate positioning and image quality and may also serve as safety mechanisms that prevent over insertion. As discussed earlier, diagnostic devices may contain any combination of elements described. For example, in FIGS. 10-20, outer ear elements may contain LEDs in the outer ear elements which emit light which is transmitted by standard components such as fibers, channels or light pipes.

Figures 10, 11, 12, 13:
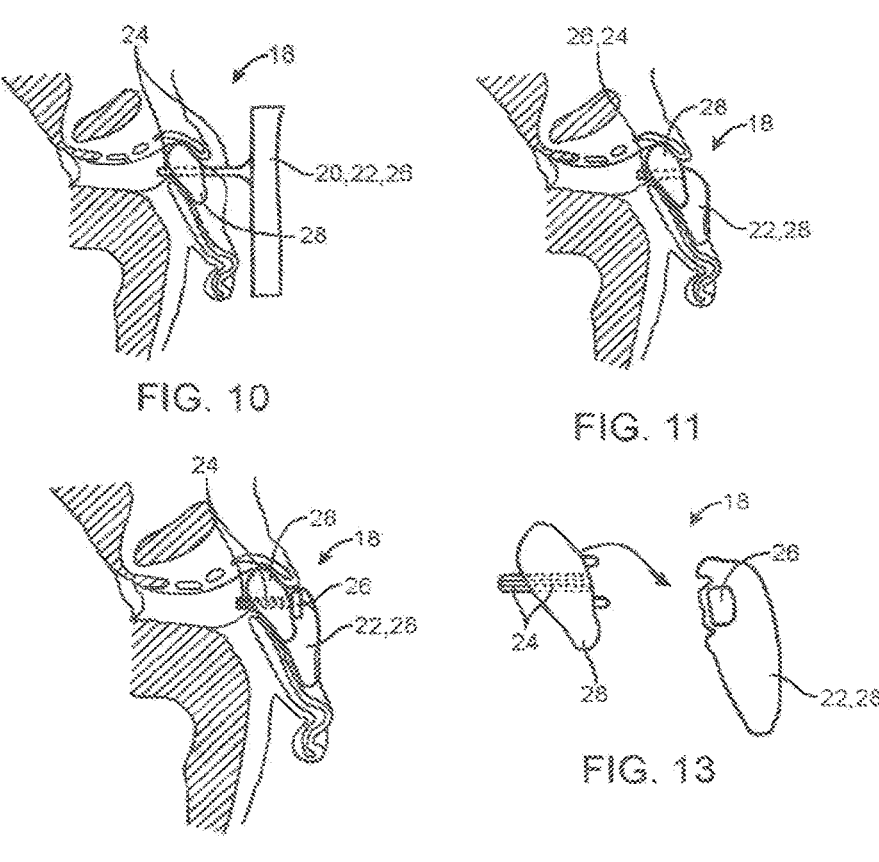
FIGS. 10-20 illustrate exemplary embodiments of an ear imaging device comprising an anatomical interface to facilitate positioning and image quality and may also serve as safety mechanisms that prevent over-insertion.

FIG. 10 shows an ear bud which is used to position and align, in the posterior of the ear canal, an imaging apparatus with the ear drum to optimize the quality of the resultant images. The ear bud and imaging apparatus are attached to a port on the smartphone which aligns with the camera for image capturing.

FIG. 11 illustrates an ear bud attached to an outer ear element. The ear bud contains the imaging apparatus with a video chip at its tip. The outer ear element contains the necessary electronics and transfers the image, via radio frequency, BLUETOOTH, wire, or other protocol, to another device such as a smartphone for output and display of the medical data to the Internet.

FIG. 12 illustrates an ear bud and outer ear element. In this Figure, the outer ear element contains the video chip as well as any ancillary electronics. The ear bud has fiber optics or a channel to allow transmission of the image to the video chip. The entire embodiment consists of a single hardware element.

FIG. 13 illustrates another combination of an ear bud and a detachable outer ear element. In contrast to FIG. 12 which shows a single hardware element, FIG. 13 illustrates that the components are detachable. This embodiment allows for different sizes of ear buds to be supplied, as well as permitting different buds for left and right ears when necessary.

Figures 14, 15, 16, 17, 18:
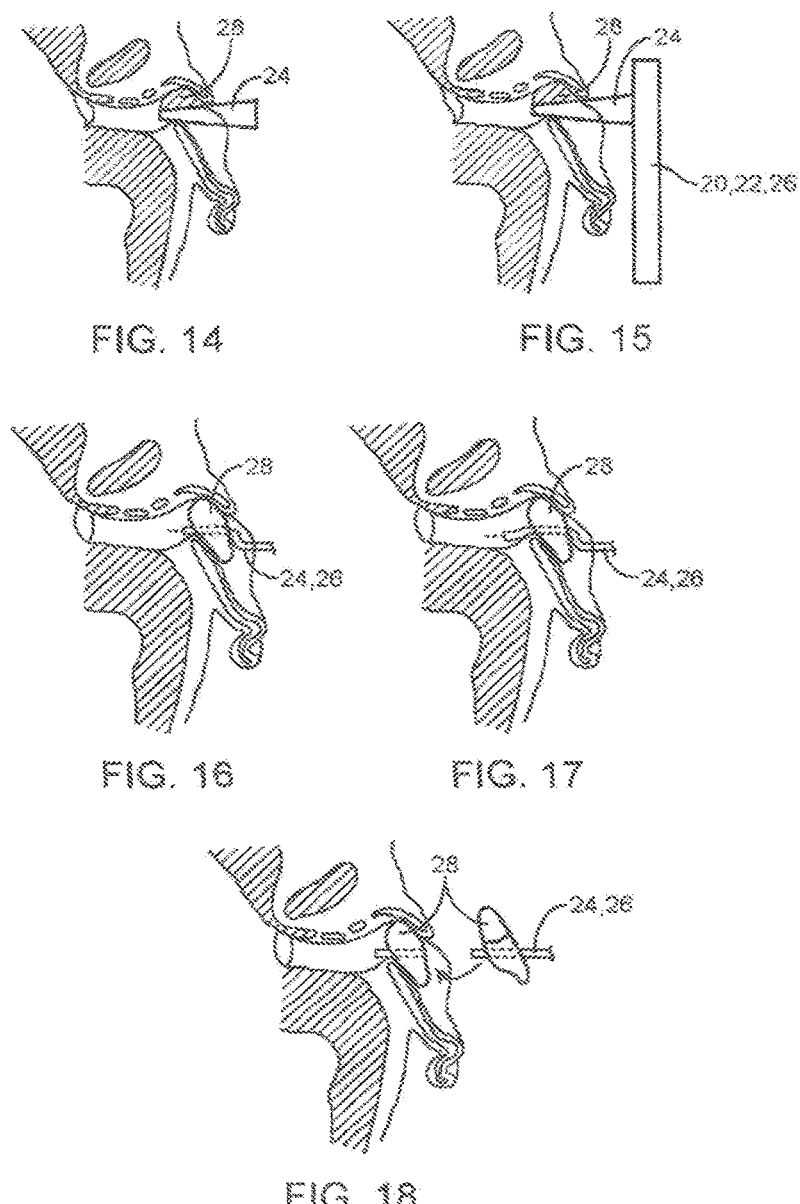

FIG. 14 shows an embodiment of the inventive device in the form of a standard speculum. This embodiment is configured with extra material on the anterior (front) side in order to position the speculum to a more posterior (backward) position for better alignment with the ear drum.

FIG. 15 illustrates an embodiment of the inventive device in the form of a speculum, with an anterior buildup and extension attached to a smartphone for image capture. The speculum element may alternatively be attached to a different diagnostic processing device (such as the outer ear element shown in the earlier Figures) to capture the image.

Figures 19, 20:
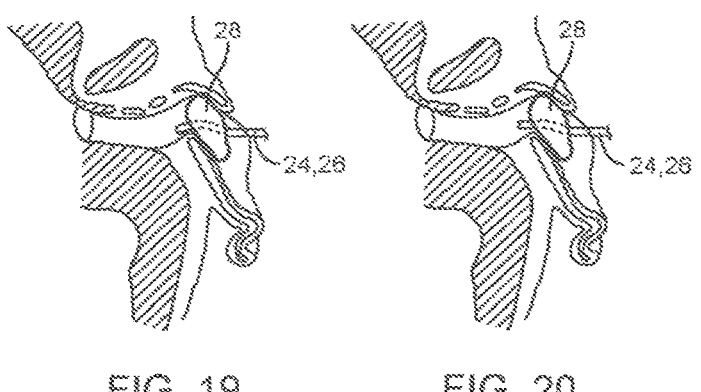

FIGS. 16-18 show alternative examples of earbuds and imaging apparatus. FIG. 18 shows a compressible ear bud with an imaging apparatus for conformity and secure fitting with an individual's ear. FIGS. 19 and 20 show examples of an ear bud and imaging apparatus that repositions itself as the ear is manipulated.

FIG. 21 illustrates features of the outer human ear for purposes of reference.

Figures 22, 23, 24:
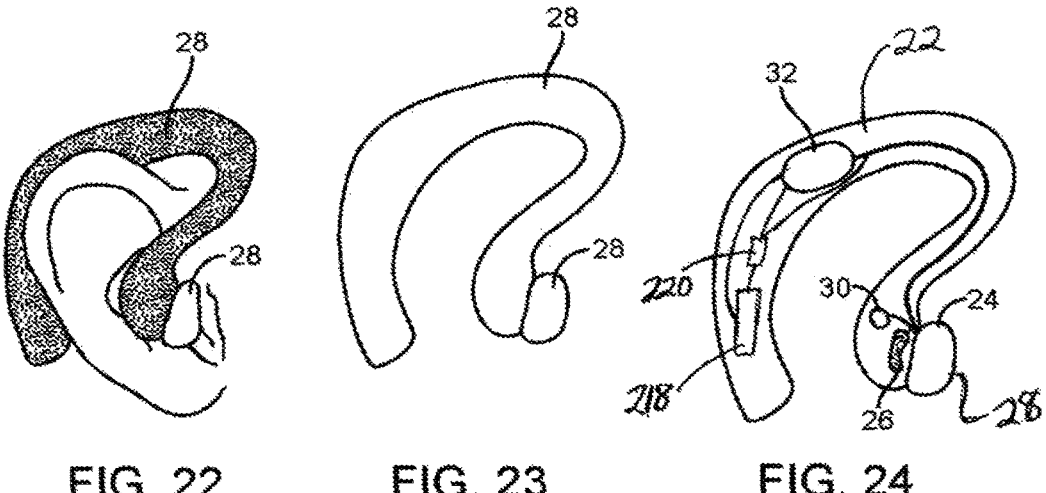
FIGS. 22-24 illustrate exemplary embodiments of an over-ear device for obtaining a subject's current medical status.

FIGS. 22-24 illustrate exemplary embodiments of an over-ear device for obtaining a subject's current medical status. FIG. 22 shows a representative device for imaging the ear. It includes two components: an outer ear element on the helix, and an ear bud inside the ear canal. The main component fits over the ear and the other component fits into the concha of the ear and/or ear canal. FIG. 23 shows the embodiment of FIG. 22 separately from the ear for clarity of view.

FIG. 24 shows an embodiment of an over ear device to which a video chip, a light source, and a speaker have been affixed. FIG. 24 shows several elements which are contained in the main component: a speaker, a light source (i.e. LEDs) and a video chip (i.e. CMOS) for capturing images or video. The speaker can transmit sounds for pleasure or for communication and the device can serve as both a diagnostic and communication device. The second component, or ear bud, transfers information (i.e. light and sound) between the elements in the main device component and the ear canal. These components can be permanently attached or the ear bud can be detachable. Other attachments may fit over the permanently attached ear bud, for example different sleeves to better fit different size ears or a device which fits into the mouth for imaging the oral cavity and throat. Alternatively, the ear bud can be detached and other size ear buds or an oral device attached. The device may be connected with a wire or by wireless means to a computing device. A wireless device typically contains a battery, a wireless chip and additional electronics.

Figure 25:
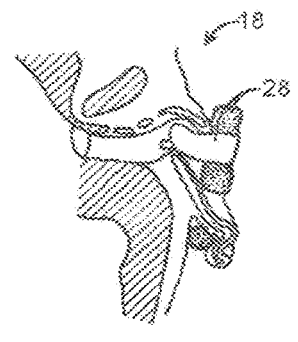
FIGS. 25-26 illustrate exemplary embodiments of an over-ear device having different configurations of the outer ear elements.
Figure 26:
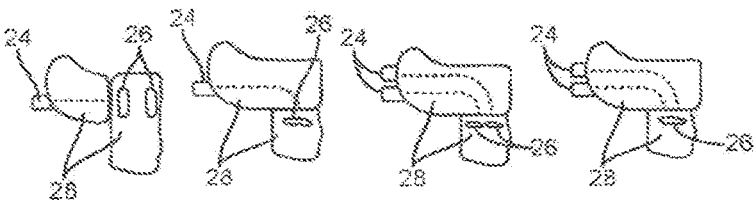

FIGS. 25-26 illustrate exemplary embodiments of an over-ear device and different configurations of the outer ear elements. FIG. 25 shows a bottom view of an over ear device. A video chip is illustrated within the outer ear element (the over ear piece). FIG. 26 shows a plurality of different configurations of outer ear elements, ear buds, and video chips. An outer ear element may be configured with one or more video chips to allow for left and right ear buds to be attached. More than one image may also be captured, for example, at different locations of the ear, or at different angles.

Figures 27, 28:
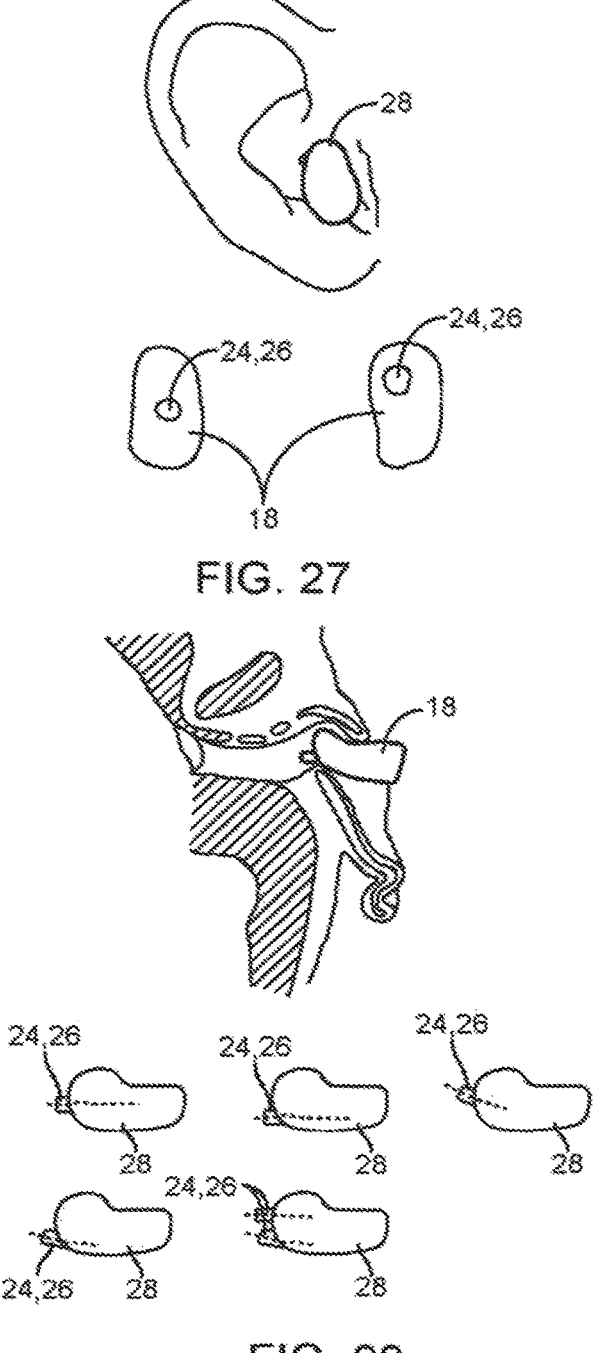
FIGS. 27 and 28 illustrate side and bottom views of an exemplary ear imaging device.

FIGS. 27 and 28 illustrate side and bottom views of an exemplary ear imaging device. FIG. 27 shows a side view of an ear imaging device. The device may be configured for interface with the subject's anatomy so that the images are captured centrally or off-center, as shown in the lower two illustrations. FIG. 26 shows a bottom view of an ear imaging device. The device may be configured and interfaced with the subject's anatomy so that images are captured centrally, off-center, and/or at an angle, as illustrated in the five drawings at the bottom of the Figure.

Figures 29, 30, 31:
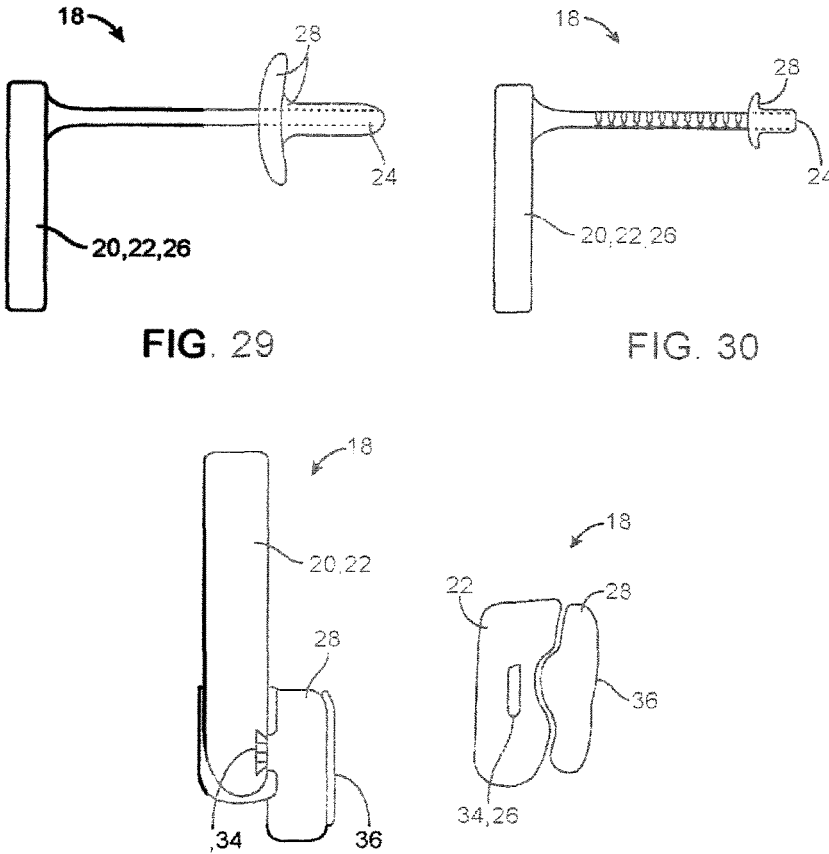
FIGS. 29 and 30 illustrate exemplary embodiments of anatomical interfaces for a medical device for insertion into a subject's mouth or ear.
FIG. 31 illustrates an exemplary embodiment of a medical diagnostic instrument equipped with a microphone.

FIGS. 29 and 30 illustrate exemplary embodiments of anatomical interfaces for a medical device for insertion into a subject's mouth (FIG. 29) or ear (FIG. 30). The anatomical interfaces are attached to a smartphone in the illustrated embodiment. The attachment of the anatomical interface to the device may be rigid (FIG. 29), or flexible as shown in FIG. 30 with a spring/coil combination.

FIG. 31 illustrates an exemplary embodiment of a medical diagnostic instrument equipped with a microphone. In the first image, a diaphragm, anatomical interface, and access-ing device are shown attached to a smartphone with a microphone for capturing sound. In the second image, a diaphragm, anatomical interface, and accessing device are attached to a specialty diagnostic capturing unit with a microphone which transmits sounds via a wired or wireless connection. Such an embodiment can be used to listen to heart or lung sounds, and the device can be used to perform the functions of a standard stethoscope.

Figures 32, 33, 35:
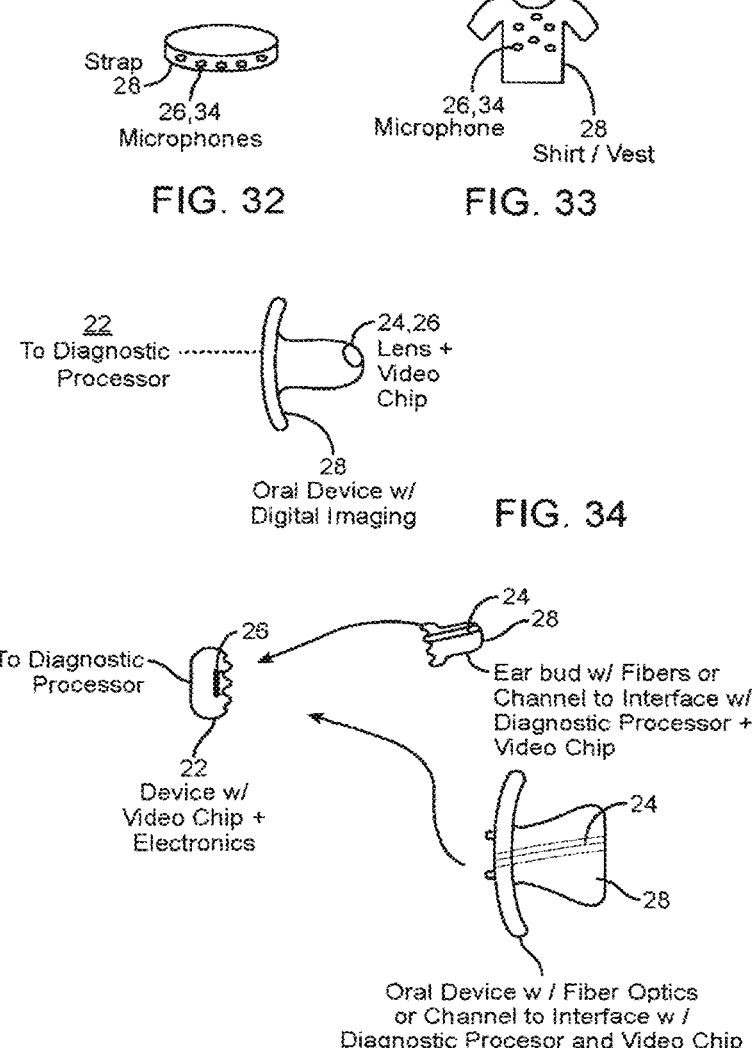

FIGS. 32-35 illustrate exemplary embodiments of medi-cal diagnostic instruments for collection of subject medical information. FIG. 32 shows a strap with microphones. This embodiment can be used, for example, to listen to a subject's chest or lungs when applied to a subject's chest. Similarly, FIG. 33 shows a shirt or vest which contains microphones. When the subject dons such articles as the strap or shirt/vest, the health care provider can listen remotely to sounds from the subject's body and thereby provide a diagnosis of a medical condition.

FIG. 34 illustrates an oral device, in the general form of a pacifier, which contains a lens and video chip for use in examining a subject's mouth or oral cavity. The oral device is equipped with digital imaging elements which commu-nicate with a diagnostic processor to enable remote diagno-ses. Such embodiments are useful to any subject, although they will provide particular application to small children.

FIG. 35 shows an embodiment of a medical device comprising an oral device and an ear bud. The oral device and the ear buds both have fiber optics or channel to interface with a device having a video chip and the associ-ated ancillary electronics, and these elements communicate with a diagnostic processor to provide medical data of at least two separate parts of subject's body.

Figure 36:
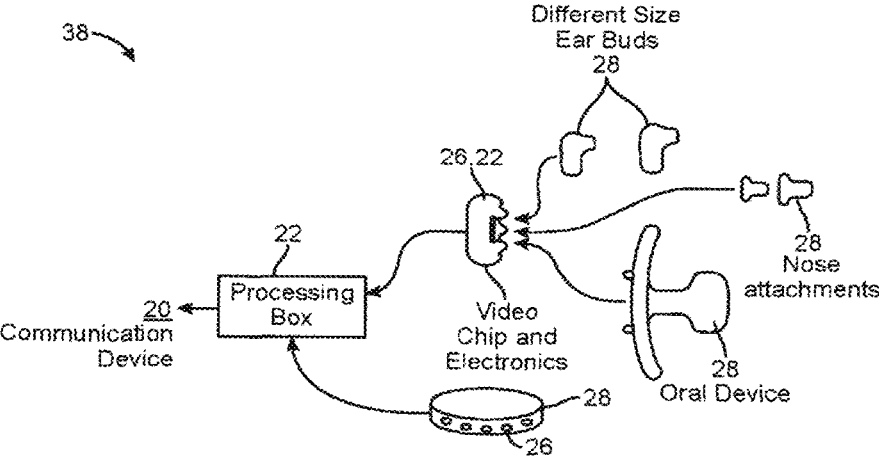
FIGS. 36-37 illustrate exemplary embodiments of kits comprising devices for accessing, capturing, and at least partial processing of medical diagnostic information in accordance with the present invention.
Figure 37:
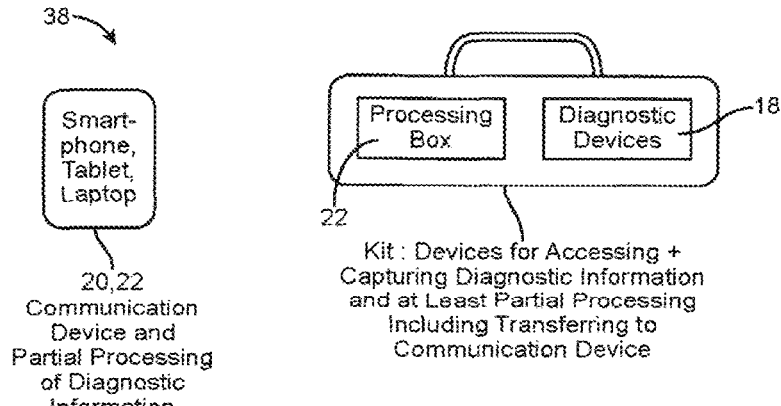

FIGS. 36-37 illustrate exemplary embodiments of kits comprising devices for accessing, capturing, and at least partial processing of medical diagnostic information in accordance with the present invention. FIG. 36 shows a kit comprising a strap equipped with microphones, an oral device, nose attachments, and different sized ear buds. These elements all communicate with a processing box which interfaces with a communication device for transmission of data to the medical provider. Any combination of these elements can be used in accordance with the present inven-tion to transmit subject medical data to a provider. FIG. 37 shows a kit comprising a computing device, such as a smartphone, tablet, or laptop, to provide communication and partial processing of diagnostic information. The kit also comprises devices for accessing and capturing diagnostic information and at least partial processing of the medical data, including transferring the information to a communi-cation device such as the smartphone, tablet, or laptop just described.

User Subsystem—Overview of Exemplary Devices, Sys-tems and Methods

Figures 38A, 38B, 38C, 38D, 38E:
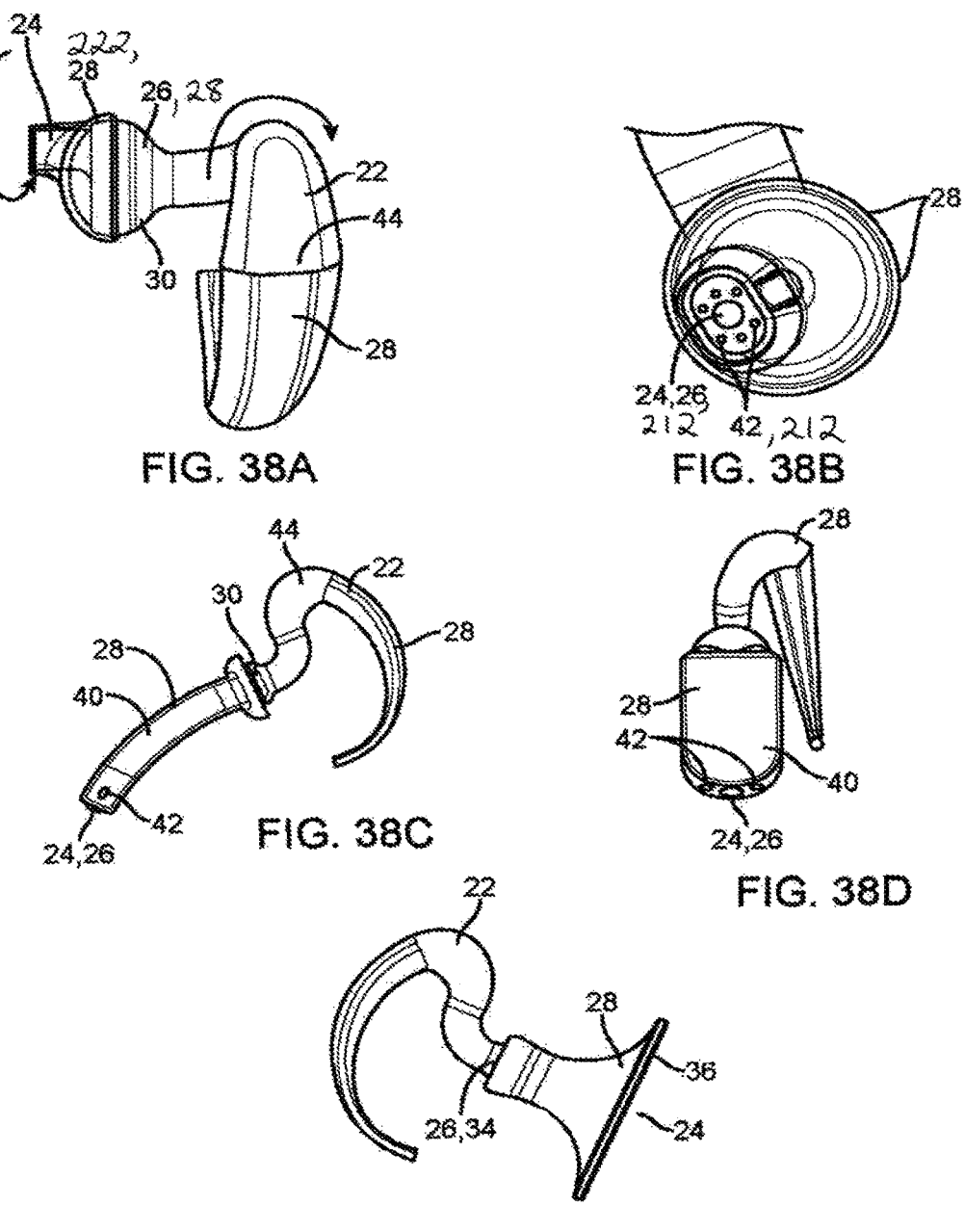
FIGS. 38A-38E illustrate exemplary embodiments of medical diagnostic devices in accordance with the present invention which are structurally configured to be placed on, in, or adjacent to a subject's body for obtaining medical diagnostic information.

Exemplary Kit for Images of the Ear and Throat and Sounds of the Heart and Lungs FIGS. 38A-E show a representative kit which includes devices to allow capturing images of the ear drum, oral cavity and throat as well as capturing sounds in the chest, such as heart and lung sounds. FIG. 38A shows the kit configured for imaging an ear. The device has a component which fits around the ear, an earbud component which fits in the concha of the ear and an extension which enters the ear canal. These components help to support the device as well as align diagnostic elements, in this case light output and input, in the ear canal. These are shown in FIG. 38B. Light sources can be contained in various locations, for example at the tip of the extension, in the ear bud or in the over the ear piece and transferred (i.e. by fiber optics, light pipes, open channels, lenses, mirrors etc.) to the tip of the device. Lenses at the tip of the device may be used to focus light in one or more preferred directions, with a narrow or wide beam. Software analysis or user/provider indication of desired capture area may be used to turn lights on or off in order to illuminate the desired object, such as the ear drum. Similar features and options may be used to capture light and images, with a video chip(s) located at the tip of the device, in the ear bud or in the over ear component.

FIG. 38A shows an attachment sleeve which fits over the extension into the ear canal and a portion of the ear bud component and can be provided in different sizes to fit different size ears to better support and/or align the device and elements. The attachment may also be constructed to fit over the ear bud portion of the device and extend only slightly into the ear canal or not enter the ear canal at all. Many different forms of the device and attachments as well as fastening methods may be used. For example, rather than the extension into the ear canal being part of the main device as is shown, the device may only contain an ear bud, with the attachment containing the extension which fits into the ear canal. Or, the main device main terminate at the lower portion of the stem of the over the ear piece and the attachment would then contain the ear bud and extension into the ear canal.

Additional attachments may be included in a kit to capture images of the oral cavity and/or throat as well as sounds of the chest, such as heart and lung sounds. FIGS. 38A-E show a main device, which serves as the over ear piece when imaging the ear and as a handle when imaging the throat or listening to the chest. FIGS. 38C,D show an attachment for imaging the oral cavity and throat. The device is configured to fit comfortably in the oral cavity, with a preferred shape that is wider than it is tall for at least a part of the length to accommodate the natural shape of the oral cavity and stabilize the device. The attachment can resemble a pacifier and preferably has a soft outside for comfort and safety. FIG. 38E shows an attachment for listening to sounds of the lungs and heart. The attachment creates a device which serves as a stethoscope. The main device may contain elements such as electronics, a wireless chip which may include Wifi or BLUETOOTH or both, one or more microphones, one or more video chips, a battery, LEDs and other elements to help facilitate capturing, storing or transmitting diagnostic data. Some of these elements may alternatively be contained in attachments to the main device. The attachments shown serve as anatomical interfaces which mate with the body and access the images and/or sounds.

FIGS. 38A-38E illustrate exemplary embodiments of medical diagnostic devices in accordance with the present invention which are structurally configured to be placed on, in, or adjacent to a subject's body for obtaining medical diagnostic information. These devices can contain a battery in an inner compartment for powering the device or for transmission of obtained medical data.

FIGS. 38A-38B illustrate exemplary embodiments of medical diagnostic devices having an anatomical interface, and which are structurally configured to be placed into a subject's ear canal. The illustrated devices are rotatable about certain positions to permit optimal fitting into the ear canal.

FIGS. 38C-38D illustrate exemplary embodiments of medical diagnostic devices which are structurally configured to be placed in a subject's oral cavity. The devices have a main body which can be inserted into the subject's oral cavity to permit optimal data collection. These medical diagnostic devices have an anatomical interface component which interfaces with the user's hand.

FIG. 38E illustrates an exemplary embodiment of a medical diagnostic device which has stethoscope capabilities, and which is structurally configured for listening to sounds from a subject's body. The device has an anatomical interface component which can be applied to a subject's chest, back, joint, or other location for listening to sounds.

FIG. 39A is a horizontal, or transverse, section (upper, or superior, half shown) of the ear and ear canal showing the different parts of the ear as well as the curvature of the ear canal. The ear canal first runs posteriorly (to the back) and then anteriorly (to the front), as shown in FIG. 39A. The horizontal (anterior/posterior) dimension of the ear canal is shown to be similar throughout the length, which is approximately 6-7 mm on average in adults.

FIG. 39B is a frontal, or coronal, section (back, or posterior half shown) and shows the superior and then inferior shape of the ear canal (up and then down). The beginning section of the ear canal has a larger dimension in this section. The starting vertical (inferior/superior) dimension is approximately 9 mm on average in the adult and decreases to approximately 6-7 mm for the remaining length of the canal. Note that the sections may not be exact frontal and transverse sections showing the center of the ear canal due to the curvature of the ear canal in both directions.

FIGS. 40-48 show various aspects of conducting examinations of the ear and oral cavity. Although these Figures have already been discussed above, it will nevertheless be useful to provide a brief summary thereof.

FIGS. 40A-40B illustrates the basic anatomy of the oral cavity. FIGS. 41A-41B shows existing devices and interfaces for the ear and oral cavity. There are safety and tolerance concerns shown by the speculum and tongue depressor examples. FIGS. 42A-42B illustrates difficulties associated with use of an otoscope. FIG. 42A shows the different parts that move relative to each other and that should be controlled during an examination of the ear. FIG. 42B shows how it can be advantageous to have a child held and/or constrained during an ear examination with existing devices and techniques. These figures show how it is difficult to use an otoscope. FIGS. 43-45B illustrate ear position and speculum positioning during an examination with an otoscope. FIGS. 44A-B show the speculum position in an ear that is in the normal anatomical position. FIGS. 45A-B show the position of a speculum in an ear that is pulled back and up. FIGS. 46-48 illustrate visualization of the throat using conventional diagnostic instruments and techniques.

Collecting Diagnostic Information In or Near the Ear—Overview of an Exemplary Device and Features FIG. 49 shows a diagnostic device for capturing diagnostic information in the ear. Capturing and processing elements are contained in the main body of the device, as well as accessing elements and inputs and outputs for light. Information is captured and sent wirelessly to a computing device which, in this system, contains processing and communication components.

FIG. 49 shows a device which is supported by the ear with an imaging extension that enters the ear canal. An attachment provides additional alignment and support. It engages with the concha of the ear and part of the length of the ear canal, in this case approximately 5 mm. This attachment positions the extension superiorly in the ear canal entrance so that the tip is positioned near the bend of the ear canal (where it may be positioned more centrally or even inferiorly in the ear canal) in order to provide a view of the ear drum (a preferred position). Since the device is supported by the ear, it moves with the ear and head and there is generally one moving part composed of the device, head and ear. The ear may need to be manipulated to straighten the ear canal in some cases in order to achieve the best image of the ear drum. If this is required, the device can move with the ear and the imaging extension can remain in a position to capture an image of the ear drum. This could be described as two moving parts, those being the head and separately the ear and device. In generally, the support and positioning of the device by the anatomy reduces relative motion between parts and makes it easier to use the device and capture and image of the ear drum. There are less moving parts and/or relative motion than generally occurs with existing devices that are not supported by the anatomy as shown in FIG. 42.

It is preferred that this imaging extension and the attachment which supports it are flexible and can move with the canal, especially if the ear is manipulated to straighten the ear canal. This device can significantly reduce the variables that the user encounters and needs to control in order to image the ear drum. For example, when the user first places the device, one hand can be used to stabilize either the head or ear while the other hand is used to the place the device. In many cases, the device may be able to be placed without requiring stabilization of the head. Once the device is in place, an image or video can be captured.

The device and alignment are generally not affected by head motion and the user can have his or her hands free for other purposes, such as communicating with a provider or operating software on a computing device. If the ear requires manipulation to achieve the best image, only one hand may be required to move the ear or both hands may be used if the user also wishes or needs to stabilize the head. In other cases, the user may wish or need to stabilize a child's head if the child is uncooperative, but not require moving or stabilizing the device or the ear. The device generally controls the orientation and depth of the extension into the ear canal. In this case, there are two moving parts at most and two hands to control them. In many cases, there is only one moving part to control and in many cases the user's hands are completely free.

Safety, Tolerance and Comfort

The soft and flexible features of the attachment also allow for increased comfort and tolerance and reduce safety concerns by limiting insertion of the extension into the ear canal as well as potential for the extension to push into the side walls of the ear canal. In addition, the ease of use and features which provide support and alignment reduce the time and manipulation required to capture an image, further increasing subject tolerance.

Figure 50A:
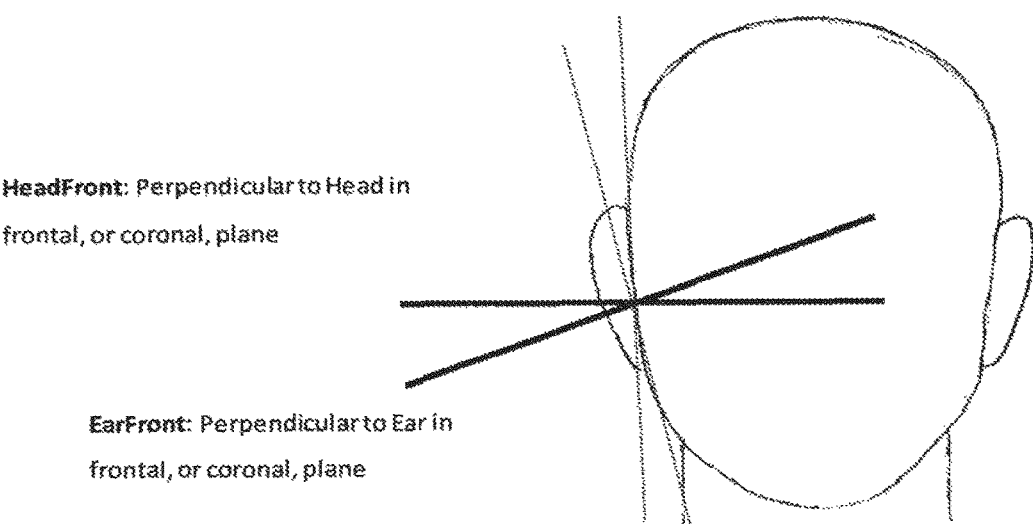
FIGS. 50A-50B and 51A-51B show exemplary reference positions and angles for obtaining diagnostic information in the ear.

Relative Angles of the Head, Ear, Ear Canal and Concha. Up and Down Positions and Angles FIG. 50A shows reference positions and angles in a frontal, or coronal, plane. Lines parallel to the head and ear are shown by the dotted lines. The side of the head is approximately vertical and the axis of the ear is offset at an angle of approximately 15 degrees. The concha may be approximately aligned at the same angle of the ear. Two solid lines going through the center of the entrance to the ear canal represent reference lines for further discussion. Head-Front is a line perpendicular to the head in the frontal plane and EarFront is a line perpendicular to the ear in the frontal plane. Note that ear angles are discussed relative to an ear in a normal anatomical position and remain relative to that position, even when the ear is moved or pulled.

Figure 50B:
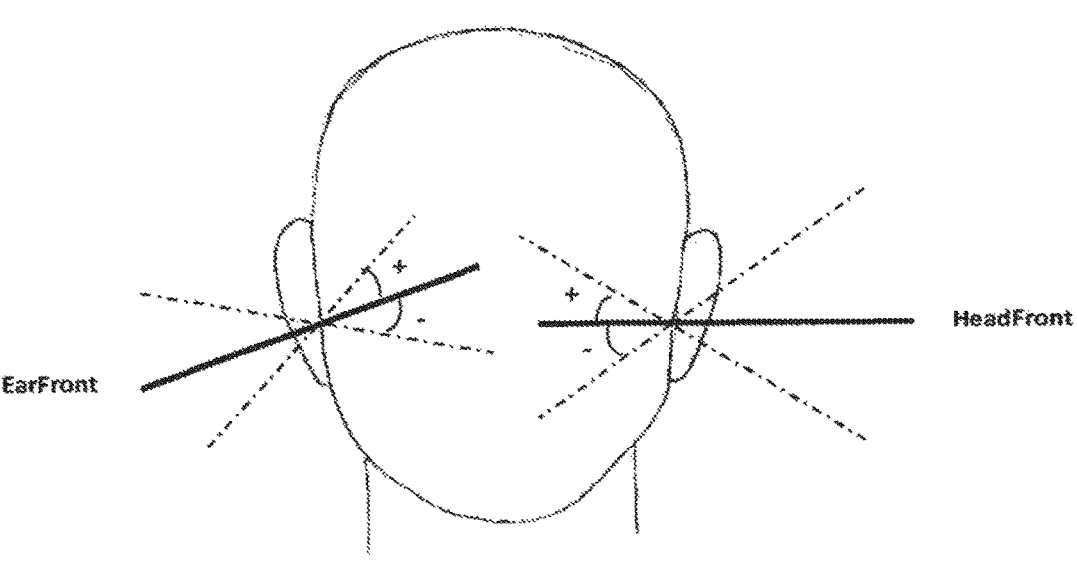

FIG. 50B shows the two reference lines, EarFront and HeadFront, and dotted lines at a positive or negative angle relative to the reference lines. These angles will be used to describe positions of imaging elements and other devices. For example, a device/element with a positive EarFront angle has an axis which is angled upward, or superiorly, relative to the ear reference in a direction into the ear. Likewise, a device/element with a positive HeadFront angle is angled upward relative to the head. If this is a shallow angle, for example 5 degrees, this device/element would have a negative EarFront angle since the ear reference (EarFront) is approximately 15 degrees offset from the head reference (HeadFront).

Forward and Back Position and Angles

Figures 51A, 51B:
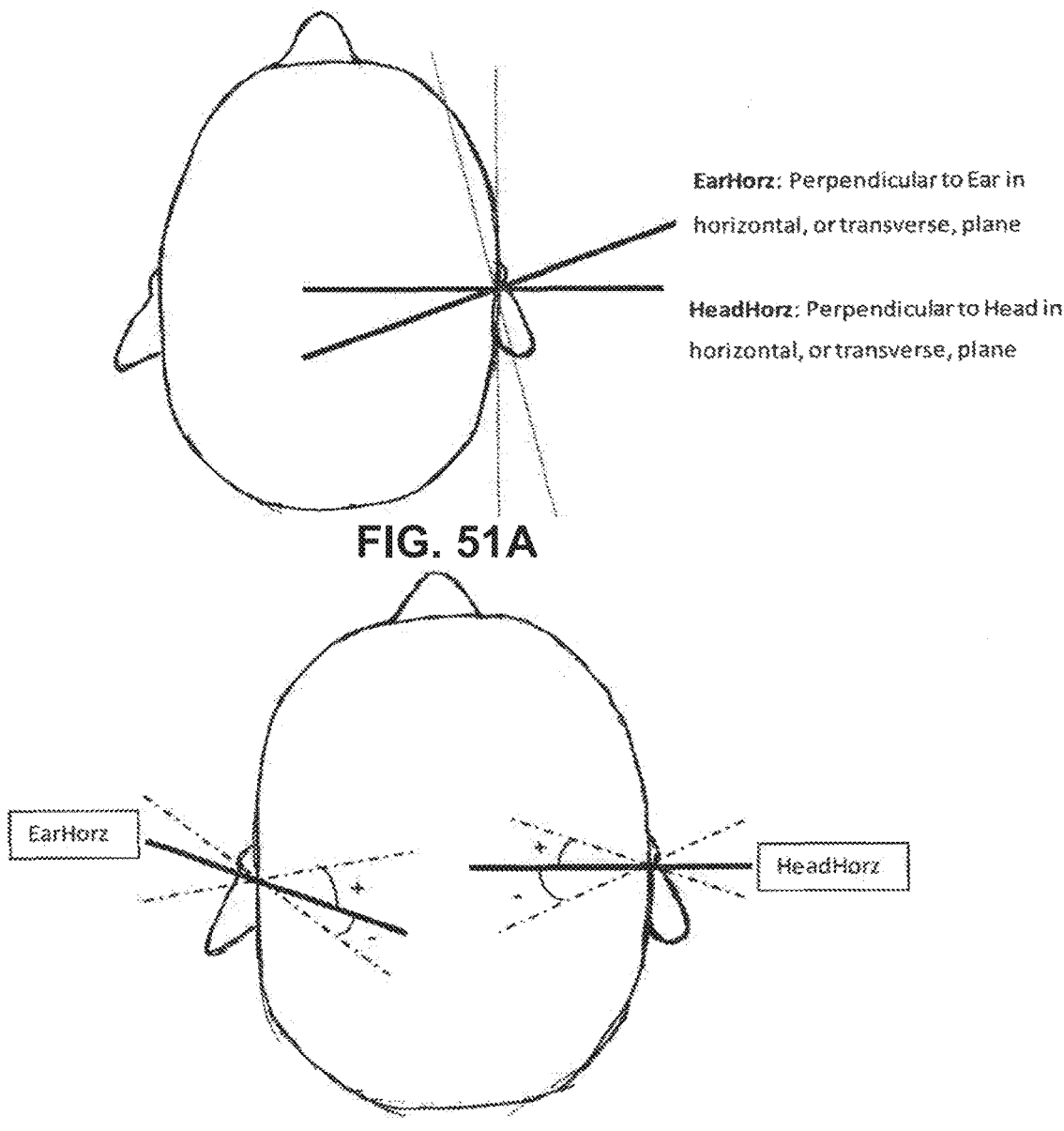

FIG. 51A shows a horizontal, or transverse, view of the head and ear. Fines similar to those shown above in the frontal plane are illustrated. HeadHorz is a reference line perpendicular to the head and EarHorz is a reference line perpendicular to the ear, both going through the center of the ear canal entrance. The ear is angled approximately 25-35 degrees (30 average) from the head in this view.

Reference lines are once again shown in FIG. 51B, along with dotted lines at a positive or negative angle to the reference lines. These angles will be used to describe the orientation of elements/devices. An element with a positive EarHorz angle is positioned so that its axis is directed forward, or towards the nose, relative to the ear reference (EarHorz).

Preferred Positions and Angles of Devices and/or Diagnostic Elements

FIGS. 52A-52B show two horizontal cross sections of the ear canal, positions of imaging devices, angle of imaging elements relative to the device and field of view achieved by imaging elements. FIG. 52A shows examples of two different viewing angles, or field of view, with imaging elements pointing straight out from the tip of the device, i.e. not angled. A smaller field of view, for example 30 degrees (shown by the area with vertical lines), with an imaging instrument in this position (indicated by the solid line entering the ear canal) does not include an image of the ear drum. However, imaging elements providing a larger field of view, for example 90 degrees (shown by the area with horizontal lines), are able to capture the ear drum. FIG. 52B shows an example of an imaging instrument with angled imaging elements (access and/or capture elements). Elements providing a small field of view, approximately 30 degrees in this case, can in this case capture an image of the ear drum. FIGS. 53 and 54A are two cross sections of the ear canal, a horizontal and a frontal section. Included in each cross section are reference lines indicating positions of imaging elements or devices and an arrow indicating the general viewing direction towards the ear canal. A view of the ear drum is obtained by device positioning, field of view of the imaging elements and/or angle of the imaging elements relative to the device. Several positions have been found to be capable of capturing an image of the ear drum without manipulation of the ear or applying pressure to tissue, as is necessary in ear exams using current otoscopes. Ideal imaging positions differ between individuals and some positions are more reliable at capturing an image for any given individual. For adults, the most reliable position using a wide angle scope was found to be as follows: insert the imaging device just below the tragus (through the intratragal notch), entering the ear canal at the lower, or inferior, edge and pointing up with an angle of approximately 45 degrees and pointing back with an angle of approximately 25 degrees. This position is illustrated by the EarHorz line (FIG. 53) and the +EarFront line with a negative offset (FIG. 54A). Alternative positions that are also capable of imaging the ear drum are shown by the other reference lines. For example, if one keeps the imaging instrument perpendicular to the head, the instrument should be positioned at the back (posterior) of the ear canal (HeadHorz with negative offset in FIG. 53) and at the top (superior) of the ear canal (HeadFront with a positive offset in FIG. 54A). There are many configurations that may work, depending on the size, magnification and field of view of the imaging device, as well as how far the imaging device is inserted into the ear canal, but this description and the figures give guidelines on how to successfully align a device and design a device to capture an image of the ear drum. The description and figures describe straight imaging devices. Alternative configurations, such as curved or flexible devices, may be constructed to position the tip of the devices in similar locations. It may also be desired to angle the accessing or capturing element, such as a lens, at the tip of the device so that it is directed straight at the ear drum. For example, if a device is constructed to angle up as it enters the ear canal, the lens at the tip may be angled downward relative to the device to better align with the ear drum. This lens, or addition lenses, then align the incoming light with the video chip. Alternatively, the device may be curved at the tip to achieve a similar result as angled elements. For example, if the device is angled up as it enters the ear canal, the tip may be curved down to better align with the ear drum.

Similar configurations may be used for FEDs, lenses or other light sources that output light. Configurations and principles may also be applied to other diagnostic elements that are intended to align with the ear drum, or alternatively these configurations may be avoided in order to align elements with the ear canal walls and not align with the ear drum.

FIG. 54B shows an ear canal shape that is more representative of an infant's along with representative preferred positions and angles of imaging instruments. The ear canal is generally flatter, and may even be directed downward in young infants. Therefore, an imaging instrument with a horizontal angle can be located more centrally in the ear canal than in an adult (HeadFront), although the posterior (or back) angle or position is still desired to image the ear canal without pulling the ear back. A positive EarFront angle is usually not necessary as it is in an adult. Rather, a negative EarFront angle may be more effective to image the ear drum in an infant Preferred positions of positive and negative EarFront angles are shown with offsets in FIG. 54B.

The lines representing imaging devices, components or elements (see FIGS. 53 and 54) are shown with various depths. Shallower placement may allow better tolerance and deeper placement may allow better imaging of the ear drum. The general principles may be followed for various depths. It is preferred that the tip of imaging devices or components enter at least 2 mm and do not go further than 18 mm into the ear canal, although shallower and deeper depths may be used. The tip should not enter further than 12 mm into an infant's ear canal. The ideal depth is just past any obstructions, such as hair and outer ear wax, and approximately to the bend in the ear canal. This results in a more preferred position of 6 to 14 mm insertion and a most preferred position of 8 to 12 mm into the ear canal for an older child or adult. For a toddler, a preferred depth is 4 to 10 mm and more preferred is 5 to 8 mm. These guidelines can be used to create devices with various positions, angles and depths for viewing an ear drum with the ear in a natural anatomical position. Similar depth guides can be used to create devices to image the ear when the ear is pulled back, or up and back, along with the angles and positions of devices shown and discussed in other sections with the ear pulled back or up and back. Angles and positions in between those shown and discussed for an ear in the normal anatomic position and with the ear manipulated for imaging (i.e. pulled back or up and back) may be used to create a device or components which are capable of capturing images with ear in a variety of positions. In this case, a sufficiently wide viewing angle is preferred, for example, a 30, 45, 60, 90, 120 or greater viewing angle.

Ear Bud Otoscope and Examples of Positions and Angles of Extensions into the Ear Canal FIGS. 55A-56B show the position of an earbud otoscope and examples of positions and angles of extensions into the ear canal and imaging elements. Various configurations for an earbud otoscope could be created. For example, it could be structured as a standalone device with built in wireless and video chip, an attachment to a separate device to help position the extension into the ear canal or part of a larger device. For now, the earbud will be discussed as an anatomical interface which helps support and align the extension and imaging elements. Positions are shown for an ear in the normal anatomical position and when the ear is pulled back and up. An ear bud placed into the concha of the ear in the normal anatomical position, and optionally part way into the entrance of the ear canal, is generally aligned with the angle of the ear. Therefore, an extension (with imaging elements including light sources or output at the tip) at a perpendicular angle to the ear bud, is generally aligned with reference lines EarHorz and EarFront as shown in FIGS. 55A-55B. An extension extending in these directions into the ear canal is in a generally desirable position to image the ear drum, preferably extending 6-14 mm into the ear canal. Depending on depth, anatomy, size of extension and imaging elements and other factors, it may be desirable to offset the extension posteriorly and/or superiorly relative to the center of the ear canal opening and/or angled superiorly and/or posteriorly. Still other desirable positions are an extension beginning inferiorly in the entrance of the ear canal and angled superiorly (a+EarFront angle) or positioned anteriorly in the entrance of the ear canal and angle posteriorly.

FIGS. 56A-56B show example of preferred positions and angles of imaging extensions into the ear canal when the ear is pulled up and back, respectively. When the ear is pulled back (FIG. 56B), the ear bud, concha and ear, may remain at an angle similar to a normal anatomical position. An extension previously described may then be pointing towards the posterior wall of the ear canal as the ear canal shape is changed and straightened out with this maneuver. While this position may still be able to capture an image of the ear drum, it is desirable that the extension change angle relative to the ear bud to better align with the modified shape of the ear canal, to a more anterior angle, as shown by the dotted line in the top right image. This may be achieved by several methods, including a flexible extension that conforms with the ear canal or a hinge or flexible joint in the extension or at the junction with the ear bud that allows rotation. Alternatively, the soft tipped extension may contact the ear canal and cause the ear bud to move in the ear canal, allowing a more anterior angle without changing the angle between the extension and the ear bud.

When the ear is pulled up (usually done with a subject older than infant age), the ear bud, concha and ear, may move to a different angle than they are when the ear is a normal anatomical position (see FIG. 56A). They move into a position so that an extension perpendicular to the ear bud is now at a+EarFront angle and generally well aligned with the modified shape of the canal in this view. In this case, it would generally be desirable that the extension angle relative to the ear bud remain consistent. In some cases, it is desirable that the extension changes angle. For example, it is preferable that the extension is allowed to angle slightly inferior relative to the ear bud when the ear is pulled up, as indicated by the dotted line in FIG. 56A. This may not apply to infants, who generally have a flatter shaped ear canal which sometimes points inferiorly rather than superiorly, so that the ear is not pulled up and sometimes is pulled slightly downward.

Other anatomical interfaces, used in conjunction with an ear bud or instead of an ear bud, to facilitate alignment of diagnostic elements with the ear drum (this includes lighting elements and other types of elements such as temperature probes) will be described later.

Anatomical Interfaces In, On or Near the Visible Portion of the Ear, Head, Neck or Cheek FIGS. 57A-61B show examples of anatomical interfaces which help to support, stabilize, position (including serving as stops to prevent over-insertion) and/or align devices, components or attachments. FIGS. 57A-57L show anatomical interfaces structured in or near the concha. Several configurations are shown, many of which identify sections of devices which fit behind tissue (shown by the dotted lines). Alternatively, similar configurations of any of the structures may also be used which move or push tissue out of the way (as shown in FIG. 57G) or rest against or on top of the tissue as shown in FIG. 57H. In one example, a section that fits in the concha may encourage a superior position of an imaging extension into the ear canal, or an imaging extension may extend at an angle, for example up and back (or superior and posterior), into the canal from the section that fits into the concha or otherwise interfaces with the ear or head. FIG. 57L shows an example of an interface, preferably flexible, that has a larger bottom, or inferior, portion to encourage a superior position of an imaging extension into the canal. Interfaces can be structured to flex and partially enter the canal. These or similar structures may be incorporated into a new device or attachment for imaging the ear, be standalone attachments or be combined with devices or attachments that exist today. For example, adding these support features to a standard speculum (as shown in figures by the cone shaped feature) can help to increase usability of a device using a speculum. Structures may alternatively by attached to the main device rather than an attachment, extension, or speculum. Other types of support and alignment include overhead or behind head straps or supports similar to current earphones.

Figure 57A:
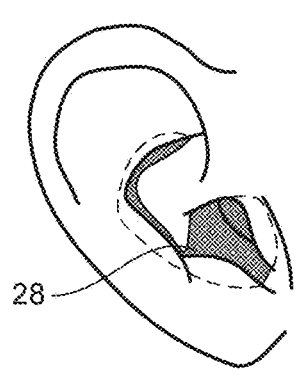
Figure 57B:
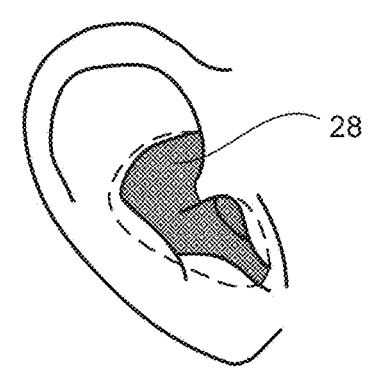
Figure 57C:
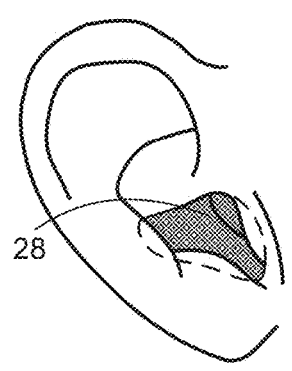
Figure 57D:
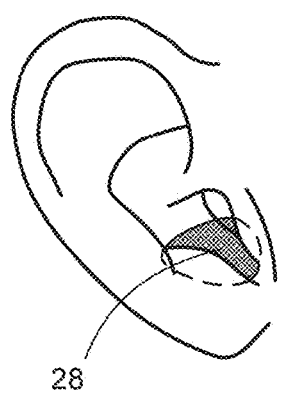
Figure 57E:
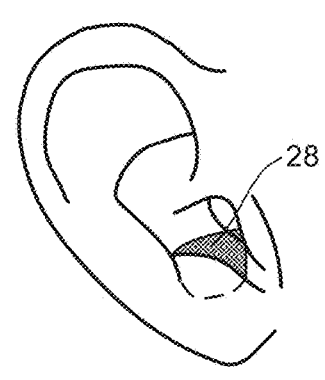
Figure 57F:
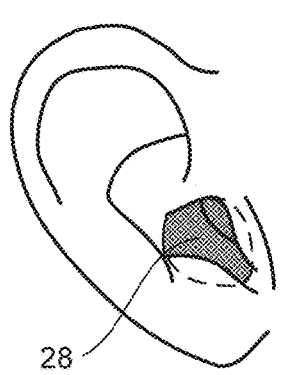
Figure 57G:
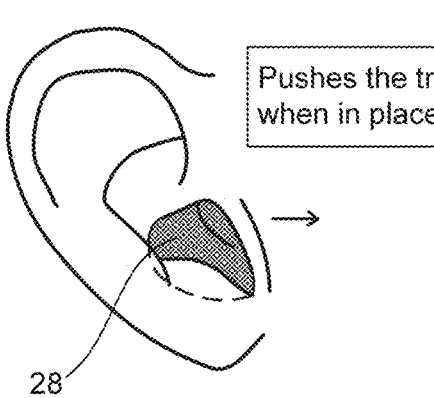
Figure 57H:
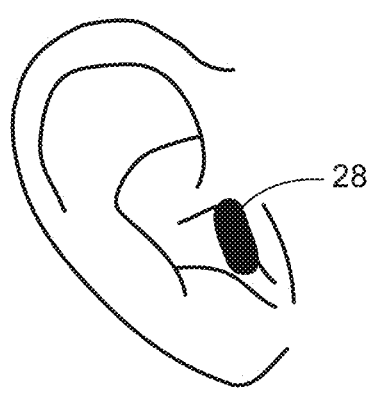
Figure 57I:
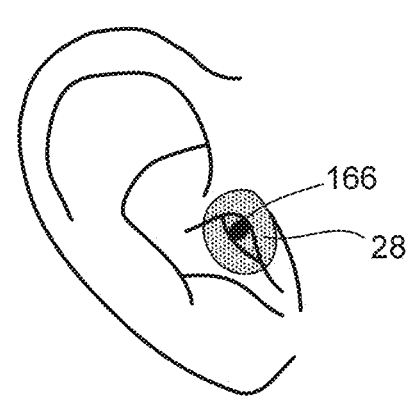
Figure 57J:
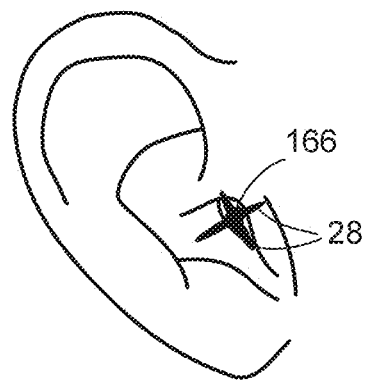
Figure 57K:
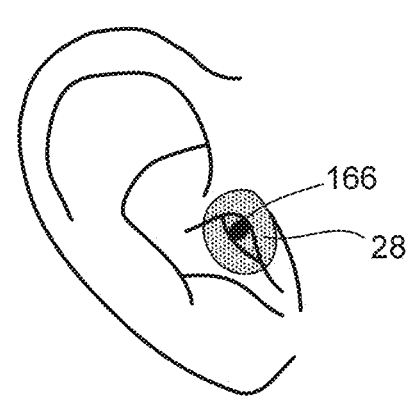
Figure 57L:
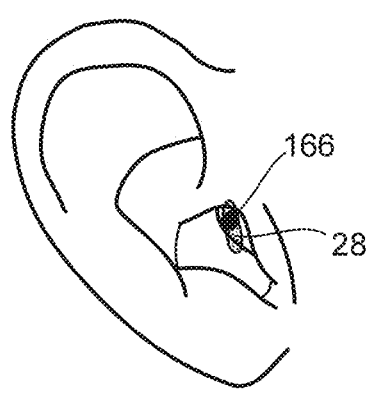

Structures can be incorporated into a device or attachment (or supplied as attachments themselves) which fit into either the right or left ear, for example FIGS. 57A, B, or which can fit into both ears, for example FIGS. 57H, J, K. Structures in FIGS. 57J, K are preferably flexible or elastic and partially or fully conform into the anatomy but do not allow over-insertion of an extension into the ear canal.

These structures may be manufactured in a variety of ways with a variety of materials, but are preferably made of soft materials that can flex such as silicone, urethane or other thermoset or thermoplastic. Structures may be built with multiple durometers of plastics, for example a harder inner durometer which maintains the shape and a softer durometer outer shell to provide comfort and which may also conform to the anatomy.

Figures 60A, 60B, 61A, 61B:
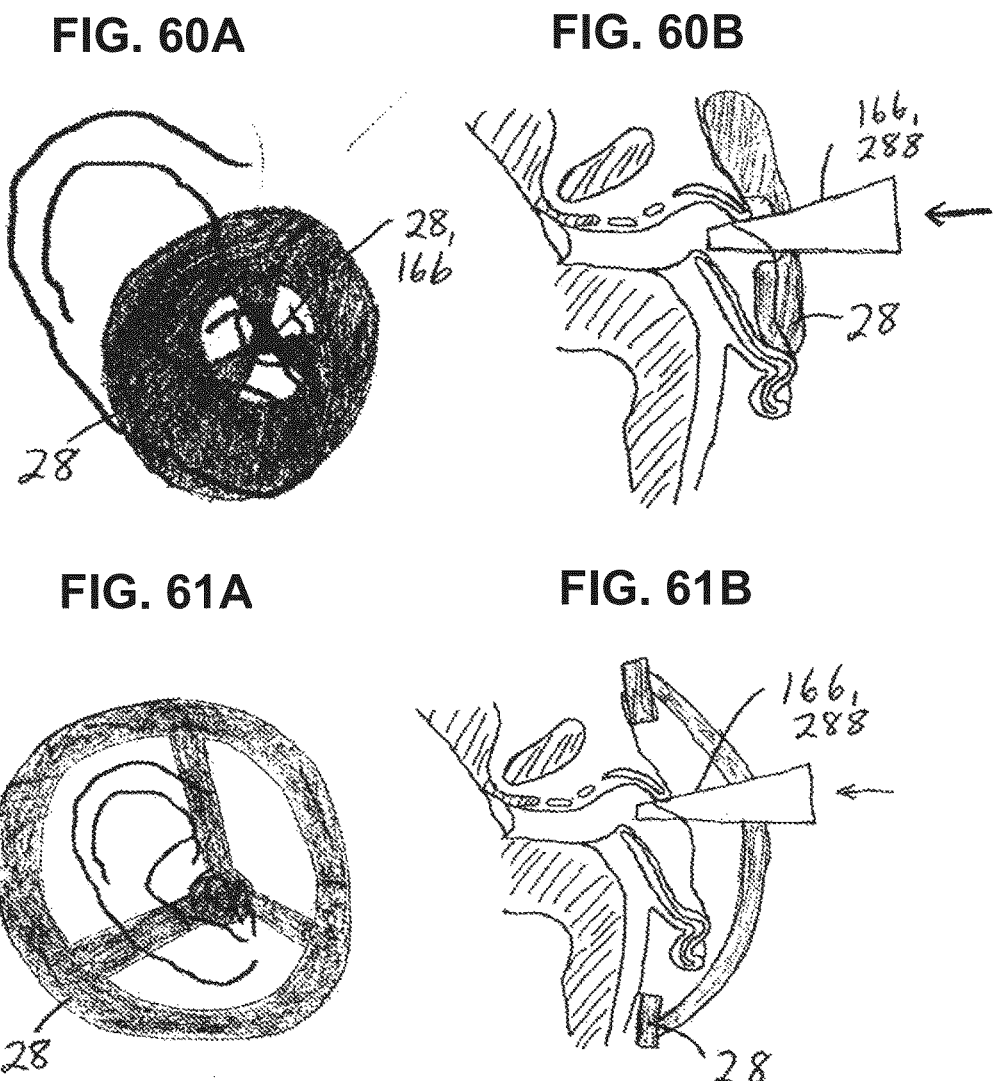

Structures may be joined to components, attachments or devices by compressible means, such as springs, to allow some motion. For example, a support structured for placement against the ear or cheek may touch the ear, cheek or head prior to insertion of a component into the ear canal. This allows the device to be stabilized prior to insertion. Force is then applied to compress the compressible member or members and allow a component to enter the ear canal to image the ear drum. Similarly, the supports themselves could be compressible or deformable, for example made of foam or filled with air. If filled with air, the outer shell is desirably elastic, similar to a balloon. See FIGS. 60A-60B and 61A-61B for examples. FIG. 59 could also be compressible. FIGS. 60A-60B show an on-ear support structure that can be structured to flex or compress. FIGS. 61A-61B show an around ear support structure that can be structured to flex or compress.

Structures may contain diagnostic elements and/or serve as locations for attachments to collect additional diagnostic information. For example, interfaces may contain sensors for temperature, oxygen saturation, blood pressure, and/or heart rate. Such sensors may be optical sensors which may use or monitor light outputs of various wavelengths. Another example is a cheek support that contains microphones. This cheek support may then be used as a stethoscope. Ideally the microphones are covered by a diaphragm to collect the sound or the support allows for a diaphragm attachment or other means for channeling the sound to the microphones. Anatomical Interfaces In or Near the Ear Canal FIGS. 62A-65E show examples of anatomical interfaces which help to support, stabilize, position and/or align devices, components or attachments. These or similar structures may be incorporated into a new device or attachment for imaging the ear, be standalone attachments or be combined with or incorporated into devices or attachments that exist today. For example, adding features that engage with the ear canal to a standard speculum may help to increase alignment of the tip and the usability of a device using a speculum. Speculums could be manufactured with these features or sleeves or similar attachments made to mate with or attach to a speculum. For example, a short sleeve made from urethane or silicone or similar material may be slid over a speculum to a distance away from the tip. This sleeve could have a variety of outer shapes, such as a circle, oval or flower petal. This sleeve can be structured to be close to the diameter of the ear canal (and could even be slightly larger if it is made from a compressible material such as foam) so that it helps to encourage a position or alignment of the tip of the speculum. The sleeve may be configured with a center hole or offset hole to encourage a more central or more offset position of the speculum. Similarly the hole through the sleeve could be at an angle, encouraging the speculum to be angled in the ear canal. Instead of a sleeve, a speculum may be molded with a similar structure.

Figure 62C:
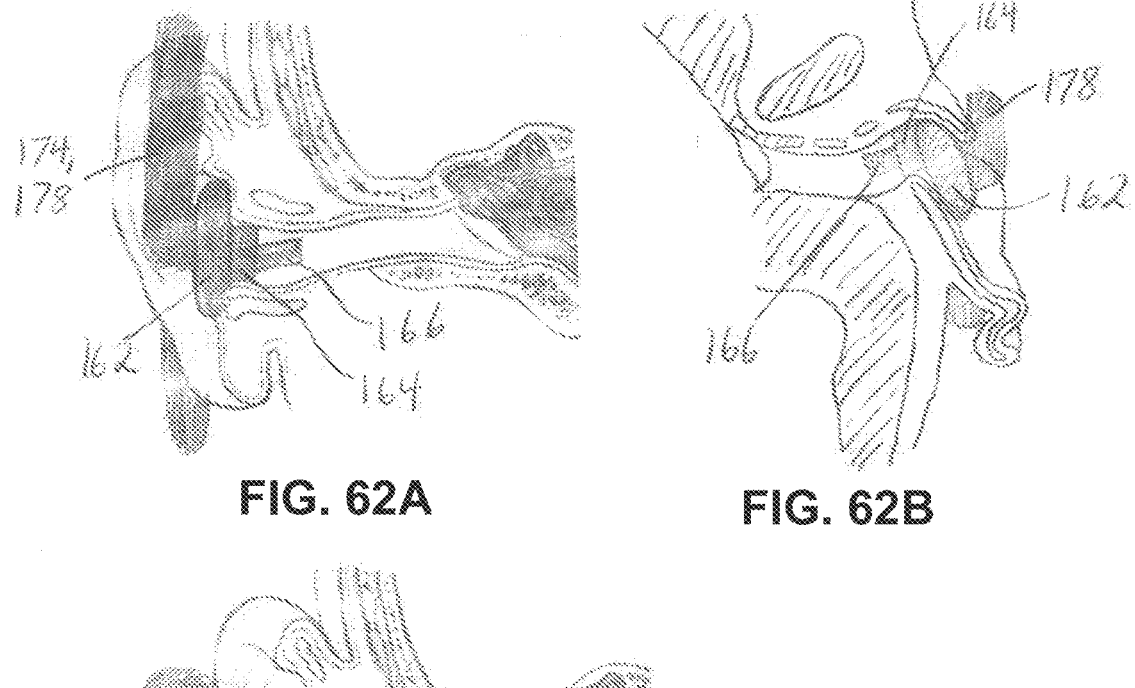
Figures 66A, 66B, 66C:
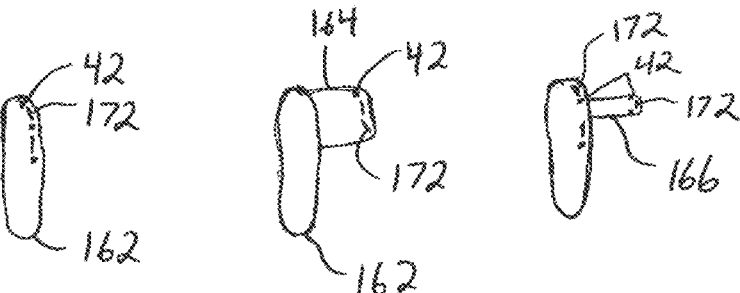
Figure 66D:
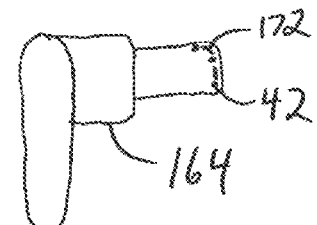

FIGS. 62A-62C shows devices which include support and/or alignment structures within the entry of the ear canal as well as structures which engage with the visible part of the ear. FIGS. 62A and 62B show an anatomical interface in or near the ear canal in one example extension position. FIG. 62C shows an anatomical interface in or near the ear canal in an example extension position different from that shown in FIGS. 62A and 62B. FIGS. 63 A,B show other examples of structures both within the entry section of the ear canal and further in. FIG. 63C shows an example of a structure that has a longer lower (inferior) portion which encourages a superior position of the extension. This structure is preferably flexible. FIG. 63D shows a structure which has a more flexible top (superior) section to encourage a superior position. FIG. 64 shows various structures which may engage with both the outside visible portion of the ear as well as in the entry of the ear canal. These structures can encourage certain positions or angles of sections of devices which extend into the ear canal, in these cases an extension is shown in the upper, superior, region of the ear canal. Structures can be flexible and allow partial entry into the ear canal and help fit different sizes and shapes of ears and ear canals. FIG. 64C shows a structure which is offset inferiorly relative to the extension and ear canal. FIG. 64D shows a structure which has two sections of with different flexibilities. The more rigid section helps encourage a position of the extension, in this case a superior position, and the more flexible section helps conform to different ear sizes and shapes. FIGS. 65A-65E show examples of various shapes and profiles of structures that can be placed near the entrance or in the ear canal.

Hand held devices or devices supported by the head and not the visible portion of the ear may also be constructed with support or alignment features within the ear canal. Devices which are intended to be supported by the hand or facilitate the option to be supported by the hands (see FIG. 62C) may also include one or both features which engage with the ear canal or the outer visible ear. Larger hand held devices may not inherently be supported by components which are structured to engage with the ear canal (although they may be supported by features which engage with the visible ear). Ear canal interfaces may help with the alignment or positioning of these devices as previously discussed (i.e. speculum attachment). However, components or sections of larger devices may be stabilized or positioned by ear canal interfaces. For example, a large device with a flexible extension may have an anatomical interface on the extension which supports and/or positions the flexible extension while the larger device may be moved within a limited range without moving the portion of the extension in the ear canal or the portion just near the tip of the extension. Smaller light weight devices may be supported or stabilized by structures which are designed to interface with the ear canal and provide support, stability or alignment.

These devices show support and alignment in the entry portion of the ear canal which is larger in diameter as well as alignment further in the ear canal. One or both of these locations may be used to support and/or align the device and elements.

Examples of positioning the imaging or diagnostic extension or elements. FIGS. 62A, B show a part of the device engaging with the entry portion of the ear canal and an extension into the ear canal containing image capture and/or access elements. In this example, the extension is angled upward (superiorly) and backward (posteriorly). FIG. 62C shows the extension at a generally horizontal angle but offset upward (superiorly). Elements may be contained directly in the part of the device engaging with the entry portion of the ear canal and similarly be angled or offset without an extension.

Support/Alignment features that engage with the entry of the ear canal may take many shapes but are preferably oval in shape to match the shape of the ear canal entrance.

Features may be short or long and may be conformable similar to some ear plugs. The outside of these features should consist of a soft polymer, such as polyurethane or silicone. Another example is a half oval that is supported against the lower, or inferiorly, wall of the ear canal. Other shapes and materials such as flanges, cones, hair like or flower petal features, and solid, foam or air filled materials may all be used to construct support and alignment features in or near the ear canal. Two thin protrusions may extend up and down from an extension into an ear canal (similar to two thick hairs), and may serve as an oval (if the total length is close to the major diameter of the oval) or circle engagement because side to side motion would be resisted by the hairs which would encourage a center alignment of the extension, unless one hair is shorter than the other, in which case an offset position would be encouraged.

While many positions and angles may be used to image the ear canal, it is preferable that positioning features in the entry of the ear canal position the extension in a superior position and/or a superior angle when the ear is in a normal anatomical position. If positioned at a superior angle, the extension may start inferiorly, or lower, at the entrance of the ear canal and angle superiorly, or upward. It is also preferable that the extension is positioned or angled towards the back, or posteriorly, in the ear canal. These positions and angles give a higher likelihood of imaging the ear drum without moving the ear. If the ear is pulled to straighten the ear canal, a more central positioning of imaging elements is preferred. The imaging access is ideally positioned past the hairs in the ear canal and approximately one third of the way into the ear canal so to reach the bend in the ear canal. It is also preferable that there is some flexibility in the extension and/or position of the device if the ear is pulled back and up to straighten the ear canal. Ideally, the extension will take less of a posterior and superior position and/or angle if the ear is moved.

It is preferable that the extension or imaging and lighting elements are more centrally located further into the ear canal.

Another preferred embodiment includes an extension which is angled superiorly and posteriorly (up and back) with imaging and lighting elements angled relative to the axis of the extension. Ideally the elements are angled inferiorly and anteriorly (down and forward) relative to the extension. If the ear is pulled back, the extension may flex to be more in line with the straightened ear canal. This flex may cause the imaging and lighting elements to move to be more in line with the extension, now that the extension is more in line with the ear drum. In this case the elements move relative to axis of the extension.

Diagnostic Elements

Lighting and Imaging Elements

Figures 67A, 67B:
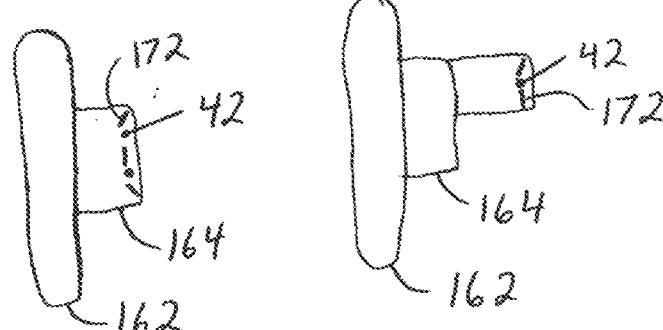

FIGS. 66A-67B show examples of locations of diagnostic elements, in these cases illustrated as light output locations (circular dots) and image/light input locations (lines). FIGS. 66A-66D show top views and FIGS. 67A-67B show front views. (Elements are shown contained 1) in an earbud (FIG. 66A), which is structured to fit in the concha in the outer visible portion of the ear and may also partially enter the ear canal 2) in an extension structured to fit in the entrance of the ear canal (FIG. 66B), 3) in an earbud and in an extension (FIG. 66C) and 4) in an extension that extends from a section intended to engage with the entrance of the canal (66D). Light output elements may take a variety of forms such as LEDs, lenses, open channels or fibers. Likewise, light/image inputs, or accessing elements, may be lenses, open channels, fibers or other structure intended to allow light input. Light output sources (such as LEDs) and light capture elements (such as a CMOS video chip) may be located at or near these locations, in another location in, on or near the device or contained in an existing device such as a smartphone. Various features, such as lenses, channels and fibers, may be used to transmit light between locations. Other diagnostic elements may also be located at these locations, such as temperature or electrical contacts or sensors.

Inflatable or Expandable Elements

FIGS. 68A, B show top views of an exemplary inflatable or expandable device in a deflated state and in an inflated state, respectively. One or more parts of the device may have chambers to allow inflation with air or another fluid. The device may be inflated after being placed in the ear during each use, allowing a tight fit or encouraging structures to conform to anatomy and/or helping to achieve a preferred position for capturing diagnostic information. The device may also be inflated in order to adjust the size and then kept in that state for future uses.

Flexible, Hinged, Rotating, Curved and Angled Components

FIG. 69 shows an example of a device with a rotating part. In this embodiment, an extension into the ear canal is connected by a hinge joint to an ear bud. When the device is placed into an ear in its natural resting position, it may take a configuration similar to the figure on the left. When the ear is pulled back, the tragus or other surrounding tissue pushes on part of the extension causing it to rotate and be directed more anteriorly, a more favorable position for imaging the ear drum when the ear is pulled back. This hinge allows the extension to better align with the ear canal in different positions and in different people with different shaped anatomy. Various types of joints may be incorporated, including ball joints. Flexible material may be used to form a hinge rather than using typical mechanical designs. This may allow motion in any direction and also be deflected by anatomy of different shapes or when the ear is pulled.

FIG. 70A shows a device with sections joined at angles relative to each other. Angling parts relative to each other may be used to better fit the shape of the ear and ear canal anatomy and achieve a preferred position for collection diagnostic information. Parts may also be curved or flexible to achieve this. FIG. 70B shows sections joined by flexible members. The thicker section that fits into the beginning of the ear canal is joined to the ear bud with a narrower flexible joint while the narrower extension is joined to the thicker section with a wider joint.

FIGS. 71A-71B show parts that rotate to enable the device to be used in both ears, as well as to enable the ear bud and extension to conform to the ear anatomy of different people and when the ear is in different positions (i.e. pulled to straighten the ear canal). As depicted in FIGS. 71A-B, hinges allow rotation to fit left and right ears and accommodate different anatomy. FIG. 71A shows an extension that rotates relative to the earbud or other device and FIG. 71B shows a stem that allows the earbud to rotate and also an extension that can rotate relative to the earbud. A variation of joints and flexible parts may be combined. For example, the arrows in FIGS. 38A-38C show an ear device that has a stem to rotate the bud to fit into left and right ears, as well as a bud that rotates so that the extension fits left and right ears.

Figures 72A, 72B, 72C, 72D, 72E:
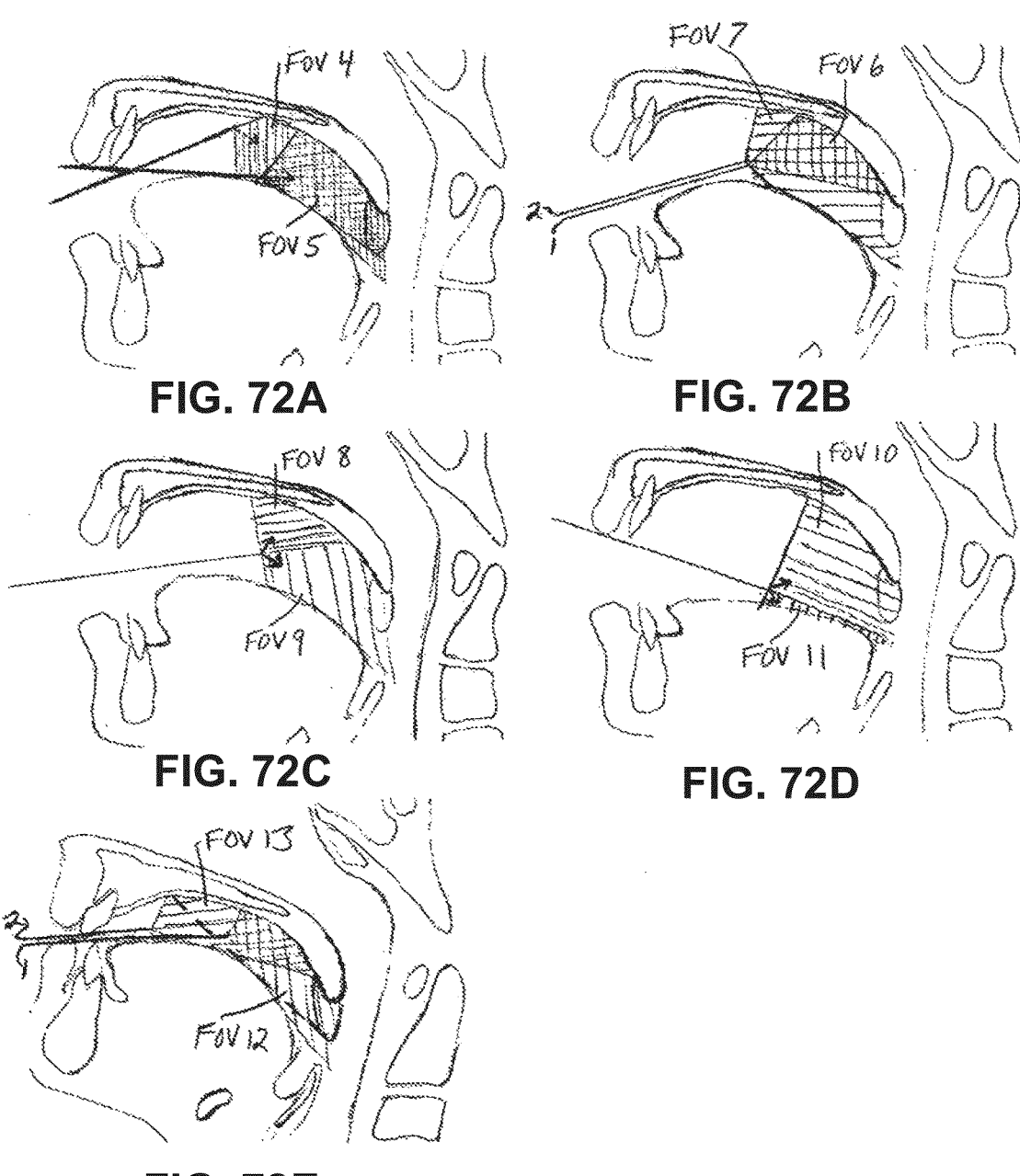

Oral Cavity and Throat: Positions and Angles of Devices and Accessing and Capturing Elements and Fields of View FIGS. 72A-E show various positions of devices and configurations of imaging elements, including angle and field of view, for viewing the oral cavity and throat, some of which are in preferred positions which in these cases allows a full view of the tonsils. In general, it is preferred that a device and/or imaging element is positioned at a distance above the tongue and further into the oral cavity in order to view an image of the throat. If anatomy is sufficiently open (i.e. jaw open, tongue depressed and/or palate raised), a device positioned at the entrance to the mouth may be in a position to view the desired areas of oral cavity and throat. The figures show imaging elements configured at different angles at the tip of devices (FIG. 72A), various field of view angles (FIG. 72B), devices with multiple imaging elements positioned at different locations (FIG. 72C, D) and an example of a threshold (past the dotted line) and window where imaging elements should be located in order to view the full tonsil (FIG. 72E). In general, it is desirable for imaging elements to provide a large field of view to make it easier to see the desired areas and provide larger positioning windows for devices in order to capture images of the desired areas and also for the elements to generally point towards the desired area(s) to obtain the best image.

Positions of Anatomical Structures and Preferred Positions and Angles of Accessing and Capturing Elements FIG. 73 shows example of various preferred positions of devices and/or imaging elements with anatomical structures in different positions. FIG. 73A shows a device positioned to image into the throat when the mouth is closed with minimal or no tongue depression. The device can be configured with a curve or be flexible to allow a curved shape to be obtained when placed into the oral cavity or a combination of the two. FIG. 73B shows six different positions and shapes of devices which are in preferred positions with the mouth partially open and moderate tongue depression. In order to view more of the throat and in this case the bottom of the tonsil, imaging elements should be positioned at the dotted line or further. It is preferred that some of these devices have elements which are angled, for example numbers 1 and 2 should have imaging elements which are angled downward or also may have imaging elements with large fields of view. Other devices are shown which are curved at the tip to better angle towards the throat and tonsil. FIG. 73C shows a situation with the mouth open and more significant tongue depression. This situation allows devices situated closer to the mouth entrance to have a fuller view of the oral cavity and throat. In this situation, devices which are positioned further above the tongue can be positioned closer to the entrance of the mouth. Note that it is often not necessary to have such a large or full view of the throat and/or tonsils, in which case devices or imaging elements can be located closer to the entrance of the mouth and/or closer to the surface of the tongue.

Anatomical Interfaces

Figure 74E:
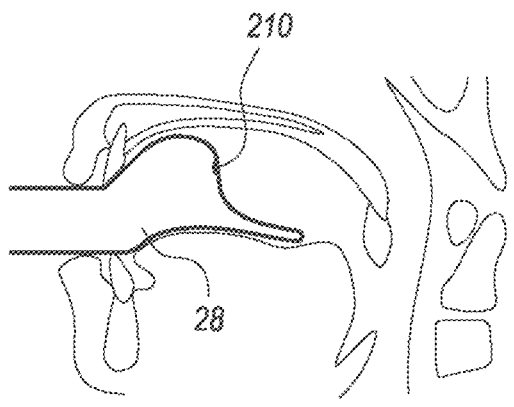
Figure 74F:
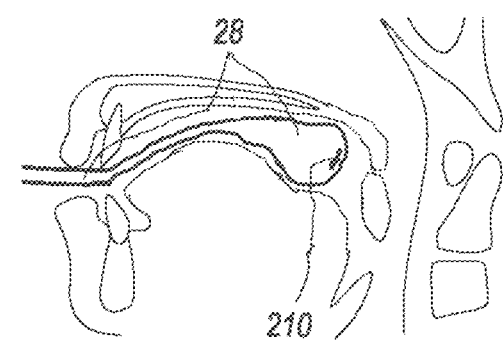
Figure 74G:
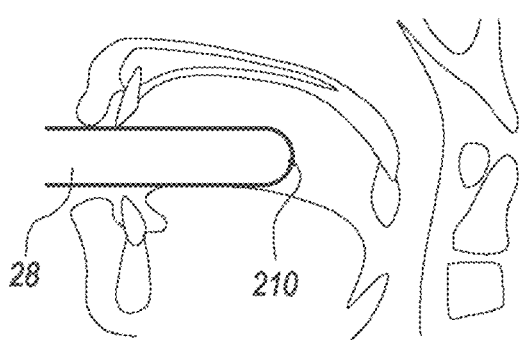
Figure 74H:
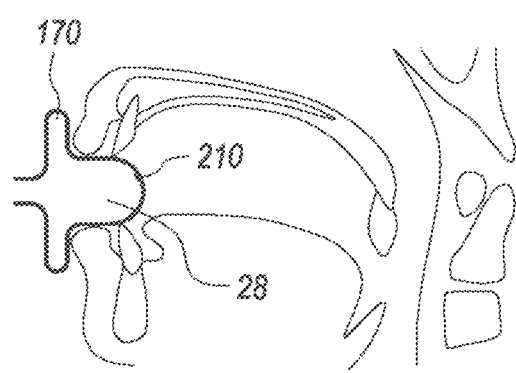
Figure 74I:
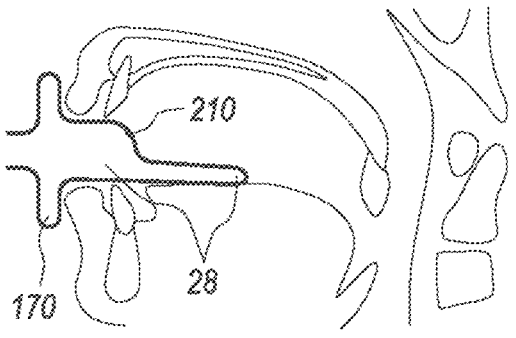
Figure 74J:
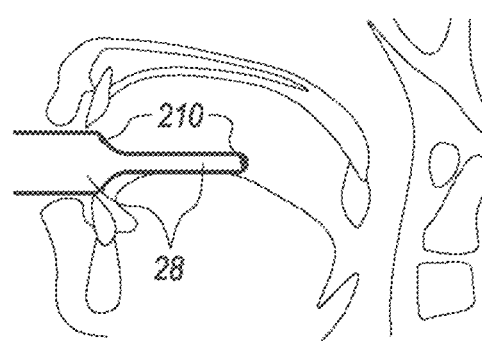
Figures 79A, 79B, 79C, 79D, 79E, 79F, 79G:
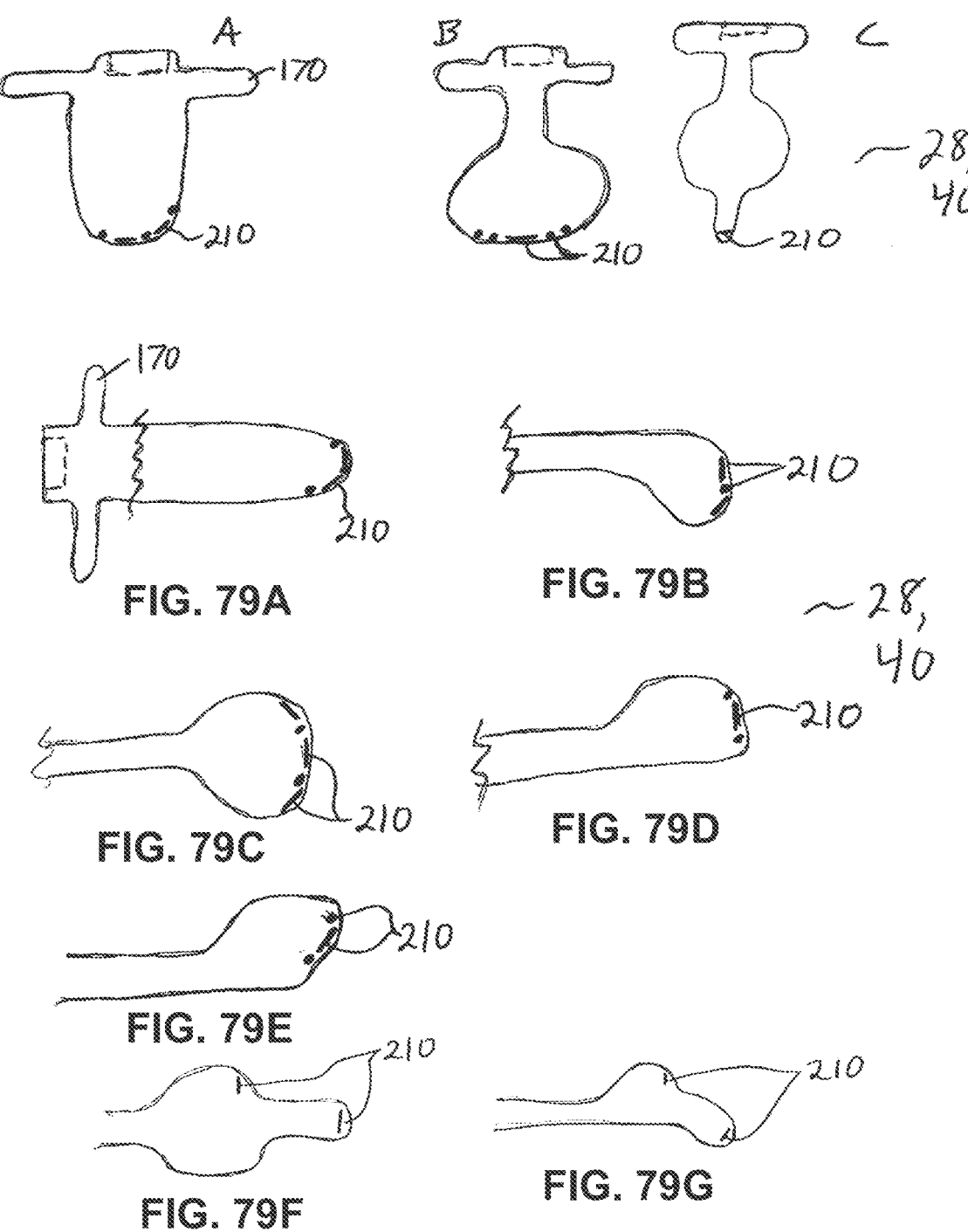

FIGS. 74A-74J show various configurations of devices and anatomical interfaces which help position diagnostic elements in preferred positions. Devices can position diagnostic elements and/or position anatomical structures. As discussed, devices or attachments with anatomical interfaces can help reduce the number of variables a user should control in order to safely image the oral cavity or throat and/or help reduce the relative motion of different moving parts (devices, attachments and/or anatomy) to help the user safely image the oral cavity or throat. As shown and discussed elsewhere, structures can be configured to contain diagnostic elements, as sleeves or attachments to other devices or attachments which contain diagnostic elements, or both contain diagnostic elements and connect to other devices or attachments which contain diagnostic elements. In general, it is preferred that imaging elements are positioned at a distance above the tongue and/or further in the oral cavity. The position of various anatomical structures affect how much of the oral cavity and throat is exposed for viewing. These structures include the tongue, the jaw, and the soft palate and uvula. FIG. 74A shows a device which minimally impacts anatomical structures, conforming to the tongue and oral cavity shape, and positions imaging element(s) offset higher in device, raised above the tongue for a fuller view of the oral cavity and throat past the tip of the device. FIG. 74B shows a device approximately midway into the oral cavity that helps to depress the tongue as well as raise imaging element(s) above the tongue. FIG. 74C shows a device which serves a similar purpose but also has a portion which extends above the tongue which can help achieve a better view of the throat by positioning the imaging element further back without requiring contact or contact with high force to an area of the tongue which is often more sensitive to producing a gag reflex. FIG. 74D shows a device that is structured for a more standard technique of depressing the tongue. FIG. 74E shows a device which depresses the tongue and positions imaging element(s) high in the oral cavity and closer to the entrance of the mouth. FIG. 74F shows a device which can both depress the tongue and elevate the soft palate (and therefore the uvula) which can expose more of the tonsil and the throat. FIGS. 74G-74J show various other configurations, for example a larger diameter, popsicle shaped, interface with diagnostic elements positioned above the midline of the device (FIG. 74G), a device and diagnostic elements positioned near the entrance to the mouth (FIG. 74H), a device with a section that serves as a tongue depressor and a section which is raised above this portion and that contains diagnostic elements, in this case the raised portion is near the entrance to mouth but can be positioned anywhere along the tongue depressor section (FIG. 74I) and a similar device with a tongue depressor section that has diagnostic elements near the tip, in a position to view the throat, as well as a raised section that has diagnostic elements, in this case in a position to view the oral cavity (FIG. 74J).

In general, it is preferred that devices in contact with the tongue have a certain height in order to provide viewing access to a larger area or that devices are raised a certain height above the tongue, or that devices are positioned far enough back, or further into the mouth, to see down past the tongue when it is desired to view the throat or that imaging elements are positioned at a certain height in devices or anatomical interfaces or a combination of one or more of these. For example, interfaces that are greater than 3 mm, or 5 mm, or 10 mm, or 15 mm, or 20 mm or greater in height, diagnostic elements that are positioned higher than 3 mm, or 5 mm, or 10 mm, or 15 mm, or 20 mm or greater in a device or interface. If a device is configured or used in a way to significantly depress the tongue, it may not require this elevated height or require elements to be at a height above the tongue. In this case it may be possible to position elements near the surface of the tongue as well as angle them up, rather than down as may be desirable with a tall device.

If anatomical structures are sufficiently open, for example the jaw open, the tongue depressed and/or the palate raised (which can sometimes be achieved by a subject saying "aahh"), a device with imaging elements may be positioned at or close to the entrance of the mouth. A device can have a mouth piece to engage with the lips and/or teeth to help maintain a mouth opening, position the device or imaging elements or serve as a stop to prevent or reduce the likelihood of the device being inserted too far into the oral cavity. Various profiles of devices may be incorporated, for example round, oval (either positioned horizontal to better match the tongue surface or positioned vertically to help raise elements and/or depress the tongue) or more complex shapes, such as one which is generally flat to match the tongue with a middle "keel" section that helps depress the tongue (FIG. 76). FIGS. 75A-75F show various profiles of devices and examples of positions of diagnostic elements. In some of these examples, diagnostic elements are positioned above the middle of the device in order to have a better view. FIG. 75E shows a larger diameter device with diagnostic elements in the middle while a smaller diameter device has diagnostic elements positioned higher up to get a comparable view (FIG. 75F). FIG. 75D shows an interface that positions diagnostic elements near the sides of the tongue or oral cavity and in this example also shows diagnostic elements that are positioned above midline of the device. It may also be desirable to position elements at or below midline in a similar structure, especially if the device is long enough to reach near or beyond the back molars. Devices may be wide or narrow or a combination, such as a wider portion near the entrance to the mouth and a narrower section further back in the midline or which can be offset to one side of the mouth or the other.

FIGS. 76 and 77 show examples of anatomical interfaces with different configurations and profiles. FIG. 76A is a top view of one device showing a wider portion for the entry of the oral cavity and a narrower section which extends further back. A wider section stays outside the mouth to limit insertion of the device. Imaging elements may be contained at various locations, for example at the tip of the device and/or near the outside of the wider portion prior to the narrower section. FIGS. 76B, C show a front and side view respectively and show a lower "keel" extension which helps depress the tongue near the midline. FIG. 77A, B, C shows a simpler construction with side, front and top views shown. FIG. 77A shows a side view of a relatively thin device that has an oval profile (FIG. 77B, C) to interface with the surface of the tongue. FIG. 77D (top view), E (front view) shows a device which is configured to position diagnostic elements near the sides of the tongue or oral cavity.

FIGS. 78 through 79A-79G show various shapes of anatomical interfaces and some exemplary positions of imaging elements. Structures are intended to fit with the oral anatomy, move anatomical structures, help facilitate tolerance or comfort and/or position imaging or other diagnostic elements. FIG. 78 shows top views and FIGS. 79A-79G show side views. Shapes can be combined in a variety of ways to facilitate accessing/capturing diagnostic information in the oral cavity. While imaging elements have been shown, various other diagnostic elements may also be included or included instead of imaging elements. For example, microphones or pressure or temperature sensors. Devices may also be able to capture fluids to help diagnose conditions. Structures may retract or compress under force, for example a compressible structure or sections joined by springs. This may be especially beneficial if using a device to collect fluids near the throat. For example, a swab may be created with a spring or other compressible member that deflects and/or retracts if the swab encounters force, such as hitting the throat, tongue or palate.

Figure 80A:
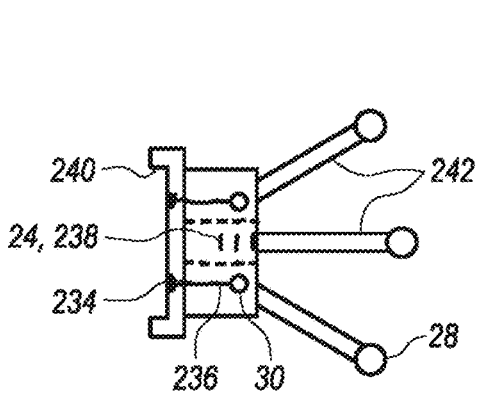
FIG. 80A-80D show a side view and bottom view of an attachment for imaging skin and having legs to provide an offset from the skin surface.
Figure 80B:
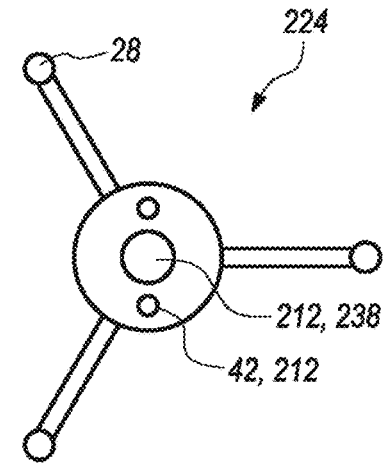

FIGS. 80A, B show a side view and bottom view of an attachment that has legs to provide an offset from the skin surface. Each leg has an anatomical interface at the ends that contact the skin. These legs, the anatomical interface at the end of the leg or other feature of an attachment, can be used as a feature of known size in order to determine the size of an image of the skin or near the skin, such as a mole, a rash or a tick. A feature may also be attached to a leg or other area of an attachment and can extend into the viewing area. It can be configured to rotate or otherwise be moved into or out of the viewing area. While an attachment can be configured with only one or two legs that create a certain offset from the skin, it is preferred that the attachment has at least three legs to provide a more consistent offset distance as well as stability for the attachment or device. The legs may be rigidly attached to the main section or be flexibly or attached, for example with spring and/or hinge connections, to allow the legs to move which may allow them to conform better to the skin surface. The legs may also be rigid or flexible, which can also provide for movement to conform to the skin surface. The anatomical interfaces are shown as round components but can be configured in a variety of ways, for example as suction cups or flat pads. Surfaces may be hard (i.e. wood or hard plastic) or soft (i.e. rubber, silicone or softer polyurethane). Surfaces can be structured to glide over the skin or to provide resistance to movement, for example with textured surfaces or soft surfaces. The attachment has a connection for joining it to a device which contains an image capturing element, for example a CCD or CMOS video chip. One or more lenses channel light from the skin to the device with the image capturing element. Electrical contacts transfer electricity from the main device to light sources in the attachment which emit light through an output, for example an open channel or a lens. Alternatively the attachment may contain batteries.

Figure 80C:
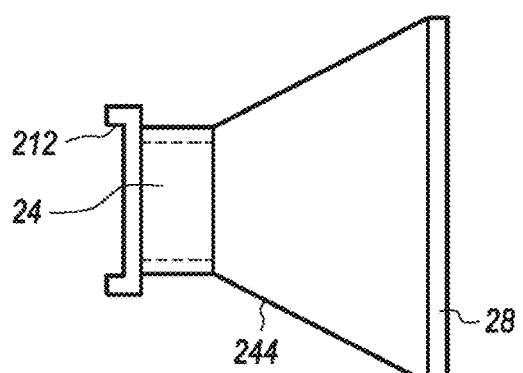
Figure 80D:
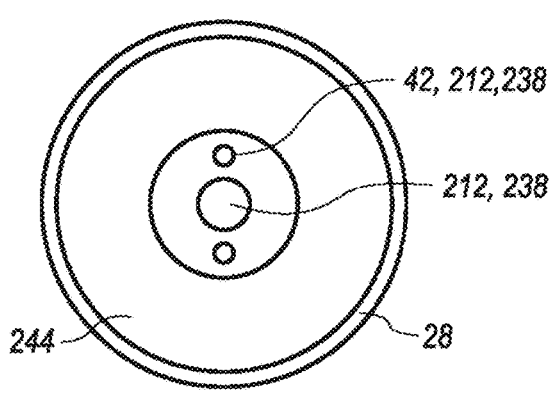

FIGS. 80C, D show a side view and bottom view of attachments with a light shield. This reduces or eliminates light from the environment reaching the skin. An anatomical interface is located at the bottom of this shield. Preferably, the interface is made of a soft material. The attachment in FIG. 80C has a through hole to allow light in and out from a main device that contains a light source and video capture element. The attachment in FIG. 80D has a lens which channels light to a video chip contained in the attachment as well as two other lenses that emit light from light sources contained in the attachment.

Figure 81A:
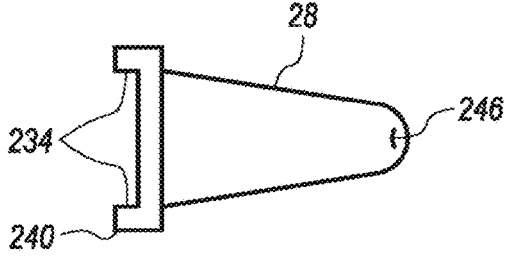
FIGS. 81A-81B show examples of attachments for capturing temperature in the ear.
Figure 81B:
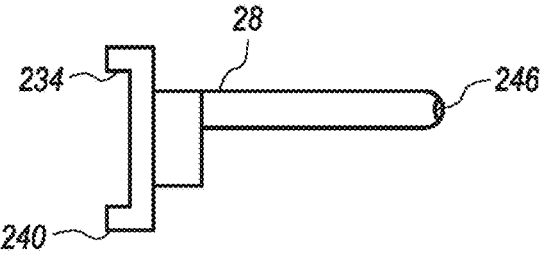

FIGS. 81A-81B show two examples of an attachment for capturing temperature in the ear. FIG. 81A shows a cone shaped device and FIG. 81B shows a device that has a longer and thinner extension that is joined to a section that fits into the entry section of the ear canal and helps position the extension. The capturing element is shown at the tip of both attachments, but can be located elsewhere in the attachment, such as in a larger part of the device that is positioned outside the ear canal or in a device that is connected to the attachment. In the case, access elements would collect and transmit the IR light to the capturing element. Examples of capturing elements include a thermopile or pyroelectric sensor.

Figures 82A, 82B, 82C, 82D, 82E, 83A, 83B, 83C:
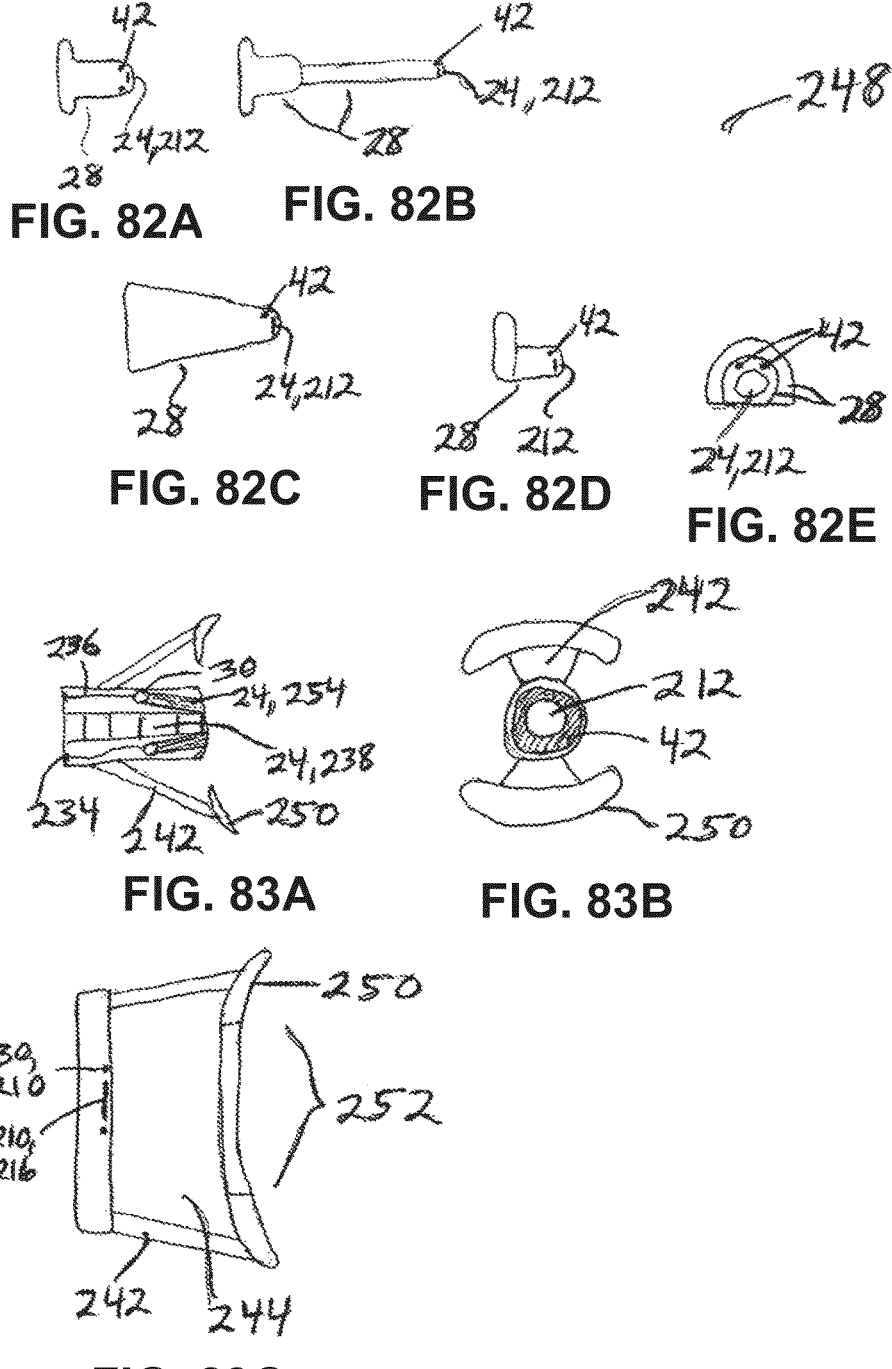

FIGS. 82A-82E show various configurations of anatomical interfaces to image the nose or nasal cavity. FIGS. 82A, 82B, 82C show side views of three structures. FIG. 82A is configured as a nose plug with a larger section that serves as a stop to prevent inserting the piece too far. FIG. 82B is a similar shape but has a thinner extension that reaches further into the nose. FIG. 82C is a cone shape with the largest diameter greater than a nostril opening. FIG. 82D, E shows a side view and front view of another interface. This structure has a stop, or larger section, that is offset and is ideally placed away from the lip (flatter side towards the lip). These may be structured as attachments which contain a connection for joining to a device which contains capturing and/or processing elements or be part of a device. Examples of light output locations are shown as well as light inputs. Light sources and video capture elements can be located near these locations at the tip, elsewhere in an attachment or in a separate device.

FIGS. 83A-83C show two configurations of attachments to image the eye. Both of these incorporate a flexible interface in the form of an eye piece that can contact locations near the eye, for example above and below, or surround the eye. FIGS. 83A and 83B show a side cross section and front views of an attachment which has an access section which is positioned close to the eye which may allow better quality close-ups. The attachment has electrical contacts to deliver electricity to light sources. Light is transmitted through access elements, such as plastic fibers, to the output or light emitting element(s), for example a lens or open ends of fibers. A lens array is shown which channels light from the input towards the capturing element (video chip) contained in separate device which is connected to the attachment. This access element can be structured in a variety of other ways, for example as an open channel or as two different lens systems, one which has greater magnification than the other. Legs connect the eye pieces to the attachment, and as discussed earlier, can be rigid or flexible and can be rigidly or flexibly connected to the attachment.

FIG. 83C shows an attachment which has a circumferential eye piece with a central opening. This attachment is configured with leg supports and a light shield to reduce or eliminate environmental light. This example shows an attachment that contains light sources and a video chip. A device or attachment may also be supplied which helps support or position a screen near the eye. For example, FIG. 83C could be attached to a device with a screen, for example FIG. 90, with the optional built-in or attachable screen, and have a large through hole where the diagnostic elements are shown in order to view the screen on the device. This may be used for various purposes including diagnosing vision.

Diagnostic Kits

Imaging the Ear Canal and Ear Drum with Connections for Optional Attachments

Figures 84A, 84B:
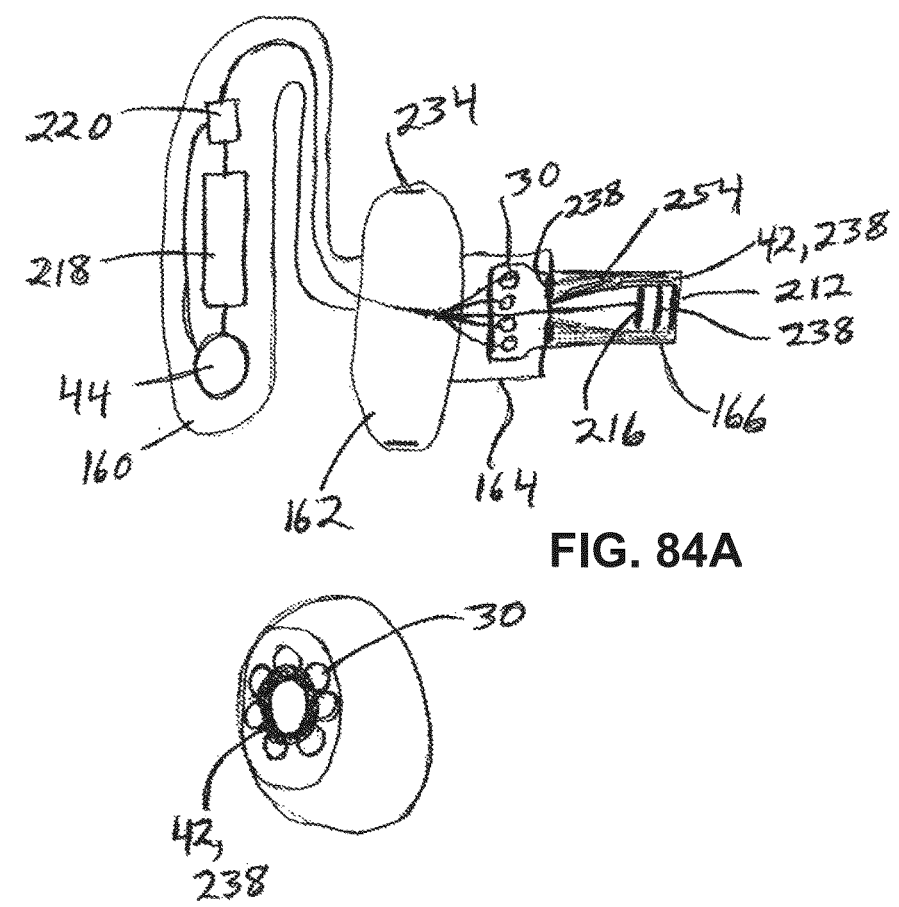

FIGS. 84A and 84B show a diagnostic device for imaging the ear canal and ear drum, and including a main device and various attachments. Most of the diagnostic elements are in the main device. FIG. 84B is a view of the tip of the device with the over ear piece excluded to show the locations of the light source and light emitting elements. Several anatomical interfaces are shown. The over ear piece and ear bud support the device and provide for initial positioning and alignment of the device. An ear canal engagement element protrudes from the ear bud and fits within the ear canal entrance to further position and align the device. An ear canal extension element then extends further into the ear canal.

Power is supplied to LEDs contained in the engagement section by the battery. Light is then carried from the LEDs by optical fibers to the tip of the extension section. A ring shaped lens is at the end of the fibers. The LEDs are contained within a chamber that limits light from escaping and helps channel it into the lenses and fibers. FIG. 84B shows the LEDs configured in a ring in the engagement section and the light exiting out a smaller diameter ring at the light output at the tip of extension section.

Additionally, one or more lenses are contained in the tip of the extension and serve as light input and access elements. These lenses transmit light to the video chip capturing element. The video chip captures images or video and transmits the signal to the electronics. A signal then travels to the wireless communication chip and is transmitted to an external device such as a computer or smart phone.

Electrical contacts in the ear bud allow electricity to be supplied to attachments. These attachments may take many forms, such as a charging device, an attachment to enable connection to a computing device or diagnostic attachments. Examples of diagnostic attachments include attachments for viewing the oral cavity or nasal cavity, a stethoscope for listening to sounds of the heart or lungs, or sleeves or extensions to better fit ear anatomy or more precisely align the device and elements for viewing the ear canal and ear drum. This is especially beneficial to allow fitting users of various ages and different anatomical shapes.

Main Device Containing Diagnostic Elements

FIGS. 85 and 86 show part of a diagnostic device similar to the one in FIG. 85 and various attachments that connect to the device.

FIG. 85A shows a simplified view of part a device similar to the one in FIG. 84. This is a top view of the device positioned to fit in a left ear. The ear bud with electrical contacts, ear canal engagement section and extension with light outputs and light input elements are shown. The ear bud may be part of a larger device that includes an over piece (such as that shown in FIG. 84) or serve as the main body of the device and contain a battery, processing electronics and a wireless chip. The ear bud or over ear piece may contain a variety of additional elements such as a data recorder, small viewing screen, power indicator, recording indicator, alignment indicator driven by software image recognition or activated by a remote person viewing the image such as a provider.

The light outputs may be FEDs positioned at the tip of the extension or be the ends of optical fibers, channels or lenses that light exits through which is channeled from FEDs or other light sources positioned elsewhere in the device. Similarly, the light access element may include a video chip at the tip of the extension, ideally packaged with one or more lenses positioned in front to focus light onto the video chip so that the desired image or video is captured. Or, the light access element may be the ends of optical fibers, channels and/or one or more lenses that light enters and is channeled or transferred to a video chip (capture element) positioned elsewhere in the device. A variety of configurations and positions of lenses, light sources, video chips, optical fibers, light pipes or tubes, mirrors, channels or other known elements may be used to supply light and capture images.

FIG. 85B shows a cross section of a thin walled sleeve which fits onto the device to better fit an individual's ear and ear canal for added comfort, safety and/or better positioning of the device and elements. The sleeve may be made from a polymer, such as silicone or polyurethane, and ideally is soft on the outside. For example, a durometer between 10 A and 90 A is preferred. Small anatomical interface extensions protruding from the sleeve help to position the device and elements as well as provide additional comfort. The shell of the sleeve can be constructed from a harder polymer or rubber and the extensions can be made of a softer polymer or rubber. These extensions may be configured in a variety of shapes and directions. For example, the extensions may be hair-like, cone shaped circumferential flanges, ring shaped ribs extending straight out or at angles, or small cylinders extending out. Larger diameter features can be constructed with softer material alongside smaller features of a slightly harder material, maintaining comfort but not allowing too much movement in any direction. This sleeve is shown with an opening at the end of the device through which light exits and enters. Alternatively, the sleeve may have one or more lenses or a transparent covering at the end through which light exits and enters.

As mentioned earlier, the ear bud in FIG. 85A can be part of a larger device (indicated by the broken line). Instead of an over ear piece, the additional component to the device may extend directly out to the side from the ear bud and contain elements such as a battery, electronics and a wireless chip. This component may take several forms and shapes and may be fully supported by the ear bud or other support component built into the device or may also be fully or partially supported and manipulated by a user. The connection to an additional device component may be flexible rather than rigid and may take the form of wire. This wire may attach to a box or small hand held device which serves as a computing device or houses elements required to transfer data to a computing device or directly to a wireless or wired router. The extension and/or engagement section may also be structured to mechanically decouple (not rigidly connected) from the ear bud and remain connected by means such as a retractable flexible wire. In this case the extension and/or engagement section, housing the light source and light accessing and capturing elements, may be inserted further into or in the end of a different longer attachment, such as an oral device for imaging the oral cavity and throat. Likewise, the ear bud may decouple from the additional device component (such as the over ear piece or side positioned component). In this case the ear bud is secured within the oral device attachment or other diagnostic attachment where it is desired to have the light output, light capture or other functional element at a further distance. The main device component (i.e. over ear piece, side positioned component, or ear bud) may also fit into a cradle on a smartphone or other computing or display device.

FIGS. 86A, B show an oral attachment, similar in shape to a pacifier, which connects to the ear canal section of the device shown in FIG. 85A. Various connection methods can be used, such as a tight fitting sleeve section and/or snap a fitting. The oral device is shown with an open channel running through the interior of the device with an open end input to allow light to pass through. This channel may also incorporate mirrors, lenses and/or fibers to channel the light. This is preferred if the channel takes other shapes, such as a curve, in order to better access desired anatomy. Similarly, the end of the channel may have one or more lenses or a clear covering rather than being open. The inside of this device is constructed of a harder material to maintain a desired shape and the outer material is a soft material for comfort and safety during use. The larger diameter ring serves as a stop to prevent over insertion and to engage with the lips. This similarity to a pacifier is intended to create a familiar device that may require little or no training or instructions.

FIG. 86C shows an alternative oral device attachment. This attachment connects to the ear bud with a tight fitting sleeve, with snaps or other known connection means. Optical fibers and/or individual channels that are open or contain lenses connect elements at the end of the extension in FIG. 85A to elements at the tip of the oral attachment. These connections are represented by single lines in FIG. 86C. One or more lenses are configured at each location for light output and light input. Here and elsewhere in descriptions of devices, lenses refer to any transparent elements, including those which have at least one curved surface to bend light as well as elements that have flat faces on both sides to allow light to pass straight through with less or no change of direction.

FIG. 86D shows a stethoscope attachment which uses one or more capturing elements (such as a dynamic, condenser or piezoelectric microphone) to convert sound into an electric signal, and can be used to listen to sounds inside the body, such as sounds of the heart and lungs. The attachment connects to the device by fitting over the ear bud section of the device in FIG. 85A. A diaphragm access sounds to the body and transmits the information to the microphone(s). In a different configurations, the diaphragm can access sounds and transmit them through various means, for example through a sound tube or through vibrations in a solid material, to one or more capturing microphones in a device. For example, these microphones can be contained in the ear bud section of the device in FIG. 85A.

Diagnostic Elements Contained in the Attachments

FIG. 87 shows an alternative design of a main body and attachments. In this configuration, diagnostic elements such as a video chip and a microphone are contained in the attachments. Accessing and capturing elements in the attachments convert the diagnostic information to electrical signals that are transmitted to the main device through electrical contacts located at the connection between the attachment and the device. FIG. 87A is the main diagnostic device and FIG. 87B is an attachment for imaging the ear canal, FIG. 87C is an attachment to listen to sounds of the body, such as sounds of the lungs and heart (stethoscope), and FIGS. 87D, E show a side and top view of an oral attachment for imaging inside the mouth and throat. Various locations and configurations and angles of video chips and light sources are shown. These locations may instead be configured as inputs and outputs and light sources and video chips contained elsewhere in the attachments.

Capturing Elements Located in Both the Main Body and in the Attachments

FIG. 88A shows a main diagnostic device that contains processing elements (wireless chip, electronics), a battery, electrical contacts, a light source and a video chip capturing element. FIG. 88B is an attachment for imaging the ear. It contains a lens system to channel light from the light input to the video chip in the main device, optical fibers to channel light from the light source in the main device to the light out output, and a light source at the tip. FIG. 88C is an oral attachment for imaging inside the mouth and throat. It contains a lens system that channels light from two different inputs that collect light from different locations back to the video chip in the main device. These inputs may also capture light from similar locations but at different magnifications. The lens system may be comprised of two different channels with lenses, or two subsystems. It is preferred that the light from two different inputs is channeled to two different locations on the video chip, for example the left and right sides. Software can be used to display both of the images or only one of the images. This example shows three light outputs near the end of the oral attachment. FIG. 88D shows a stethoscope attachment. This attachment has two different diaphragms and sound inputs and two microphones to capture sound. In between these two diaphragms is an access element comprised of a lens system to transfer light from the light input back to the video chip in the main device of FIG. 88A.

Main Body Configured to Allow Easier Support by a Users' Hands

Figures 89A, 89B, 89C:
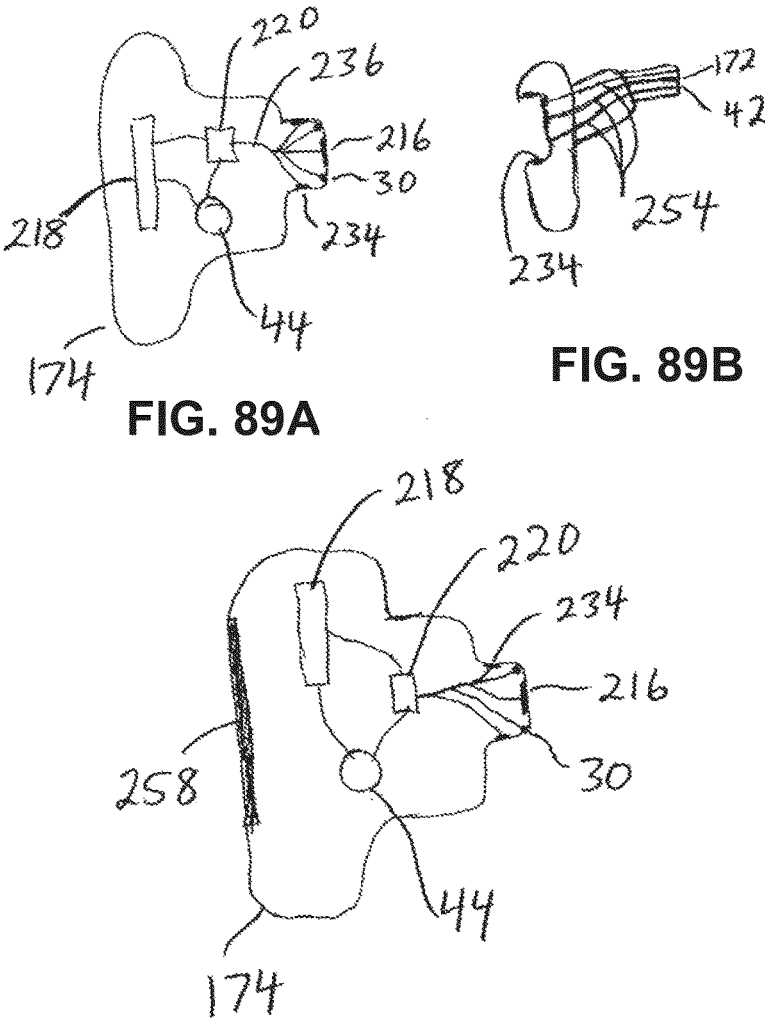

FIG. 89A shows a main device which is configured to allow a user to support and manipulate the device. The depicted configuration shows a main body which is configured to allow easier manipulation by the user's hands if desired. A screen may also be incorporated. It contains diagnostic elements, a video chip and two light sources. A similar device is shown in FIG. 89C with a display screen built in. FIG. 89B shows an attachment for imaging the ear. It contains access elements, optical fibers to channel light from the light input to the video chip in the main device as well as from the light sources in the main device to the light outputs at the tip of the ear attachment. The sections of the ear attachment are shown angled relative to one another. The sections may also be flexible or be joined to each other by flexible means. The optical fibers transmit the light to the desired locations regardless of the position of these sections.

A similar device may be constructed to be lightweight and fully supported by the ear anatomy. For example, a device similar to a Bluetooth headset that hangs down near the cheek or just outside the ear. The device is shown with only an ear attachment but attachments similar to those shown previously and later may also be provided. In addition, FIG. 89C shows a small display built into the device. This display may be small and light enough to still allow hands free use. This screen may be incorporated into higher end devices or may also be inexpensive enough to be incorporated into standard devices. The display may be high enough resolution to allow a diagnosis or be a low resolution display that is intended only to allow the user to see general alignment of the device and confirm that the required information has been captured which may be displayed in higher resolution on a separate display, such as on a tablet, smart phone, or laptop.

Various Configurations of Devices, Attachments and Features

FIGS. 90A-90C show three views of a main diagnostic device with an extension that contains diagnostic elements at the tip, to emit light and a video chip to capture light. A lens or lens system preferably if positioned in front of the video chip to access the light and channel it to the video chip. Light sources can be positioned at the tip or elsewhere in the device and channeled to outputs at the tip. This device has a main body section that can serve as a handle, an ear canal engagement section and an ear bud and stop to prevent over insertion into an ear canal. This device may be used in the configuration shown to image the ear canal or other locations of the body, or used with attachments that provide added comfort, safety or precision. The device is configured to allow imaging either the left or right ear. The ear bud is narrow enough fit into either ear and large enough to prevent over insertion. The imaging extension is positioned towards the top, or superiorly, on the ear canal engagement section. This device is shown with electrical contacts on the neck portion as well as on the back near the optional built in display. A device preferably has one or more locations for connecting attachments. Several connection locations are shown in FIGS. 90A-90C. The device has one or connections multiple locations to connect attachments. Components and sections, including the extension, can be rigid or flexible, or be connected with rigid or flexible joints.

FIGS. 91A through 104 show attachments for a main device, such as the one shown in FIGS. 90A-90C, and examples of configurations of the main device.

FIGS. 91A-91B show a display attachment that can connect to the back of the main device and FIG. 92 shows an over the ear piece attachment which can connect into the top of the main device.

FIG. 93 shows a slim ear bud sleeve that can connect to the main device and allow imaging either the right or left ears. FIG. 93A is a side view, FIG. 93B a front view and FIGS. 93C,D are top views. FIG. 93C shows the connection to the main device and a tapered ear canal engagement section. This taper may allow a tighter fit into the canal and/or help to reduce motion and maintain a position. FIG. 93D shows a slightly different shape of the ear canal engagement section. The ear bud section tapers down to the engagement section which is then a consistent thickness. This may allow easier insertion or more comfort as well as allow the user to move the device and imaging extension more easily in order to capture the desired image. The opening through the ear canal engagement section is shown to be large in this example. This allows the extension to more easily move up and down (if it is flexible). Alternatively, the through hole can be configured smaller and be offset or angled through this section to position the extension to one side or at an angle, for example, angled up or down in the canal.

FIG. 94 shows an ear bud attachment for a main device. This ear bud is structured to fit the left or right ear. This bud may be detached, rotated and reattached to fit the opposite ear or be constructed of flexible material to allow it to be rotated around the attachment section of the main device. The large through hole in the ear canal engagement section allows the attachment to fit a device with an extension positioned to one side, for example positioned upward as shown in FIG. 90A, regardless of which direction the attachment is rotated in to fit the left or right ear. Alternatively, two different attachments configured specifically for the left and right ears can be supplied with smaller through holes in this section which can fit an offset extension or help to position or angle an extension, especially a flexible extension.

Many configurations of light inputs and outputs can be created at the tip of an extension or at another location of a device or attachment. Capturing and light source elements can be located near or at these locations or further away and have light transmitted to and from them to the light input and output locations which can be configured in various ways. FIGS. 95 and 96 show various examples of the tip of an extension and diagnostic elements. One or more lenses for light output may be placed around a central lens for light input (FIG. 95A). These may emit light that is transferred from one or more light sources or be directly in front of the light source. Light sources may be located at these locations without an additional lens. A light output can be configured in a crescent or similar shape to one side of the light input (FIG. 95B). Small or large optical fibers can transmit light from light sources to the tip and emit light circumferentially around a light input (FIGS. 95C, D). These may instead be open channels. Tips of extensions or configurations of other locations with light inputs and outputs do not have to be circular. For example, light may be emitted from one side of an elongated circle shape or from both sides of an oval shape, in both cases to the side of a light input (FIGS. 95E, F).

FIG. 96 shows cross sections of exemplary tip configurations. Tips have light sources, optical fibers, a video chip and a lens system. FIG. 96A shows a slightly bulbous tip, similar in shape to a cotton swab. Light sources may instead be located in front of the video chip and not require optical fibers. Or fibers may thin out (to limit the diameter increase of the tip) and spread out from one or more light sources to surround or partially surround the light input. For example, optical fibers or channels or lenses can form a circumferential light output or two crescent shaped outputs. Light can also be directed towards the axis of the extension by pointing the light in this direction, as shown in FIG. 96A, or lenses can be used to direct light in one or more directions, for example towards the midline of an extension into an ear canal or towards the midline of the ear canal. FIG. 96B show an example of positioning one or more larger light sources behind a video chip and optical fibers which transmit the light to the light outputs at the tip.

FIG. 97 shows an ear bud with a concha piece to provide further support to the device or attachment. In one ear, the concha piece curves up and in the other ear it curves down. This component can have a connection configured similarly to the ear bud in FIG. 94. It can be removed, rotated and reattached to fit an opposite side ear or it can be made of flexible material which allows the component to be rotated around a connection of a device.

A section of an attachment may also rotate. For example, as shown in FIG. 98, a concha piece in a device or attachment may be rotated to fit the left or right ear. Or a larger section of an attachment, a rotating component, configured as a larger ear bud or more similar to a concha retainer, can rotate around another section. FIG. 99 shows a two part attachment that connects to the ear bud section of the main device in FIGS. 90A-90C.

Other examples of rotating components and connections, in these cases one piece attachments, are shown attached to various configurations of connections of a main device. FIG. 100 shows an attachment which connects from the side. FIG. 101 shows cross sections of two variations of rotating attachments which connect from the front and are placed over the extension of the main device. These figures also show two other configurations of ear canal extensions. One extends straight from the center of the ear canal engagement section and the other angles upwards. It is preferred that these extension are flexible.

Figures 102A, 102B, 102C:
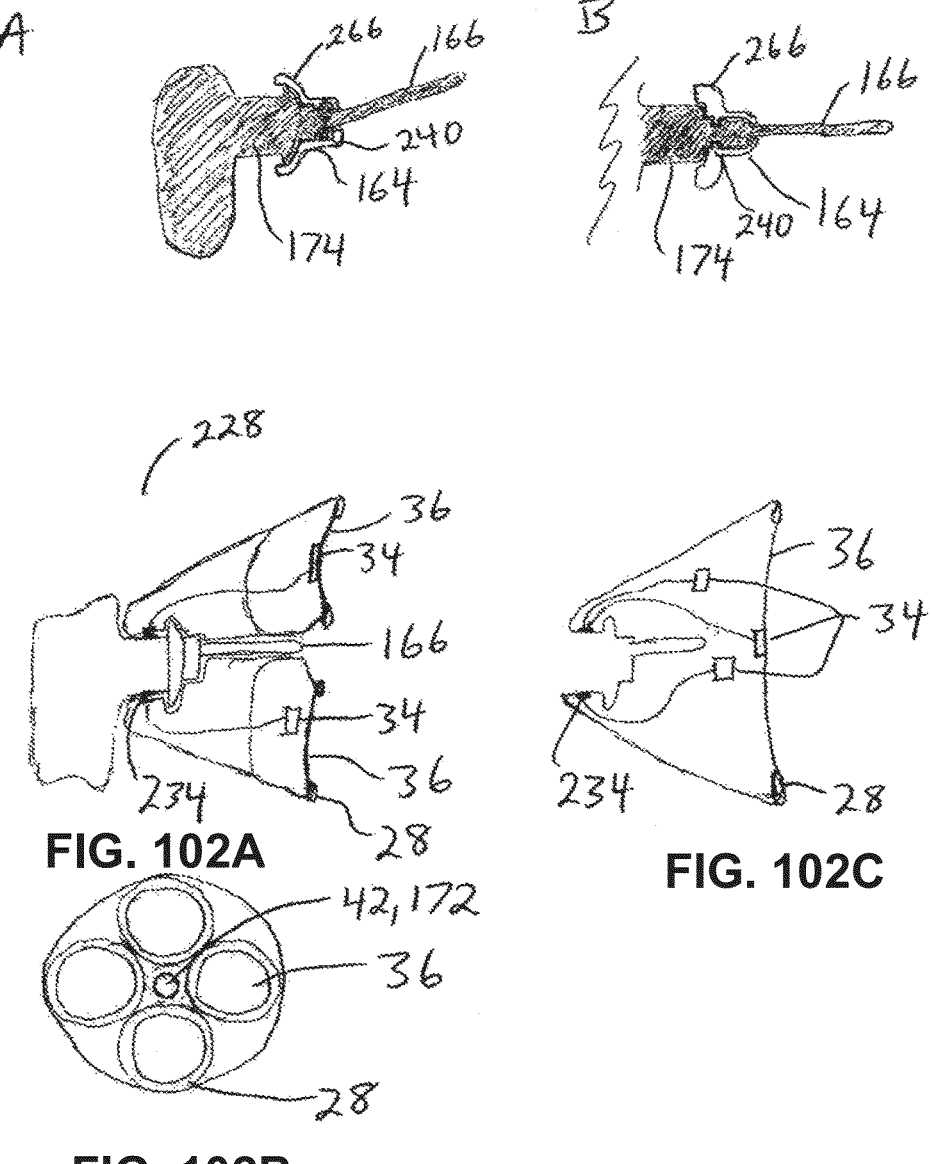
FIGS. 102A-102C illustrate a stethoscope attachment for connection to the main device illustrated in FIGS. 90A-90C.

FIGS. 102A-102C show two different stethoscope attachments that can connect to the main device in FIG. 90A. FIGS. 102A and 102B show an attachment which allows imaging through the center. This example has more than one sound access section, in this case four separate diaphragms, which can be configured to access different types, frequencies or amplitudes of sound. Alternatively, all desired sound may be captured by a microphone and filtered with software as desired. Various types of microphones, discussed earlier, can be used in one or more sound access sections. The diaphragms can be configured to immediately contact the skin directly upon placement (as shown in previous FIGS. 31, 38, 86, 87 and 88), which is preferred in most cases, or be offset from the skin surface (as shown in FIGS. 102A-102C), for example by rubber rings which surround the diaphragms. Applying pressure can change the amount of contact between the diaphragms and the skin. For example, the rings can be flexible and move inward or outward. Different sections can be created with varying areas of skin contact or with varying degrees of flexibility to allow different contact areas to be created with pressure applied. Different types of diaphragms with different thicknesses or flexibility can also be used. FIG. 102C shows an attachment with a single diaphragm or other sound access element which attaches to the main device and does allow imaging through it. However, a camera in a main device or other capture device may be offset up or down relative to the attachment to see past a side of the attachment. Microphones are shown generally placed. They are shown in large sound access areas or placed against the diaphragm. However, various other methods and configurations to access and capture sound that are generally known in the manufacturing of stethoscopes can be used. For example larger sound access areas may funnel down to a small area or a tube where microphones are located.

FIGS. 103A-103D show various views of an oral attachment which attaches over a diagnostic extension of a main device. Alignment of the tip of the diagnostic extension with the diagnostic elements in the oral attachment can be important in order to efficiently transfer light to the outputs and receive light back from the input and the access elements, in this case shown as a lens system. In order to best align the tip with the beginning of the diagnostic elements in the oral device, the oral device has an elastic joint section that can stretch to connect to the main device and force the tip of the diagnostic extension into the end of the receiving channel in the oral device, creating the desired alignment of diagnostic elements in both parts. Various other methods and configurations can be used to align the two ends of the two different parts and ensure that optical or other elements are at the desired positions and separations. At least one of the parts or components can apply force when the parts are connected. Among other things, this can accommodate for variations in manufacturing and lengths of parts. For example, the extension can retract or compress under force when the attachment is connected. Elastic sections in the parts or in the connections can be used to apply force when the parts are connected. Spring pins or other locating features can be used to locate the parts as desired. These may also be used to maintain a desired distance between the ends of the two parts, in this case the end of the diagnostic channel and the end of the receiving channel A close up of the receiving channel in FIG. 103D also shows a seal or gasket. This reduces or prevents light from the light outputs in the diagnostic extension of the main device from reflecting into or otherwise entering the other light channel in the diagnostic extension, in this case the light input. Various configurations of the end of the receiving channel can be used. In this case, it is shown as open where the light input part of the diagnostic extension ends. There is a distance prior to the first lens in the lens system of the attachment. A lens can also be at this location and mate with the end of the diagnostic extension.

FIG. 104 shows an attachment for capturing temperature, in this in the ear, which connects to a main device shown in FIGS. 90A-90C. A sensor, for example an infrared sensor such as a thermopile or pyroelectric sensor, is shown at the tip of the device. This sensor may also be located elsewhere in the attachment or in the main device and temperature related diagnostic data, such as infrared light, accessed and transferred to the sensor.

FIGS. 105 through 109C show various configurations of extendable, rotatable or moveable diagnostic sections or extensions of a device. These may be moved before or after a device is placed. For example, a device may be placed in a generally desired position prior to extending or moving a diagnostic extension. Alternatively, a diagnostic extension or section may be moved prior to placing the device and locked into position, for example with a tightening screw, by twisting a lock handle or positioning rod or by various other known means. Sections or extensions may also be locked or secured into position after placing the device. Friction may also be used to maintain a position while still allowing the user to modify the position by applying force, for example by pushing a positioning rod. Extensions or sections may also retract or move when force is encountered. For example, if an extension is inserted into the wall of an ear canal, the extension may retract if the user attempts to push the device further. This can help with both comfort and safety.

FIG. 105 shows elastic members, such as springs, which keep a diagnostic extension generally retracted. A positioning rod can be pushed to extend the diagnostic extension.

FIG. 106 shows an elastic or compressible attachment, in this case for diagnosing in the ear. The anatomical interface helps position the device and the elastic section compresses when force is applied to the device and the diagnostic extension extends further out through the anatomical interface.

FIG. 107 shows a device which allows both extension and retraction. The extension is normally partially extended. When it is positioned to capture diagnostic information, it can retract if force is encountered. The user may also further extend the extension if desired.

FIG. 108 shows extensions which exit the device at a different angle form the positioning rod. This may be desired for a variety of reasons, for example if anatomical structures are in the way of a straight path. The distal portion of the extension in FIG. 108A can be rigid so that it maintains shape under force. The distal portion of the extension in FIG. 108B should be flexible to allow it bend in the channel. The device in FIG. 108B is shown configured as an ear bud which has a section that interfaces with the entry of the ear canal. It can have elastic structures which maintain a preferred shape when it exits, for example a metal (i.e. steel or nitinol) coil or wire.

Figure 109A:
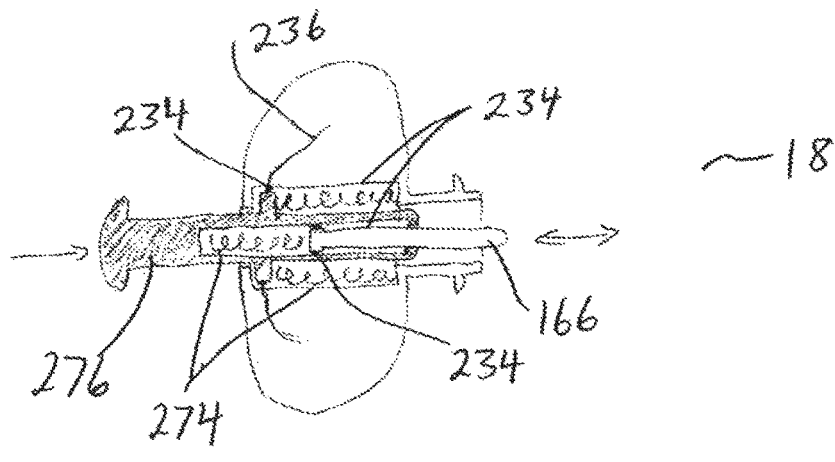
Figure 109B:
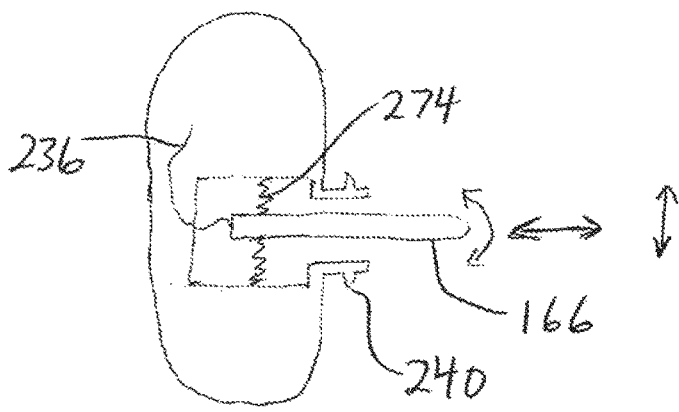
Figure 109C:
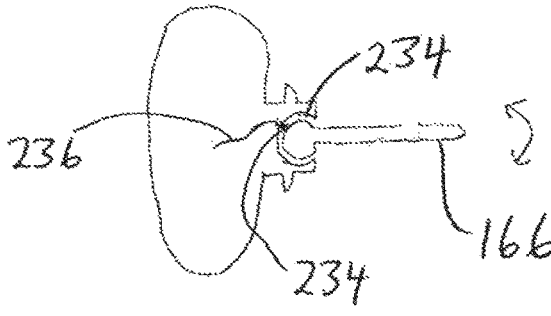

FIGS. 109A-109C show example of other configurations of movable, extendable and rotating diagnostic extensions or sections as well as electrical connections between the parts. The configurations may rotate, float, and simultaneously move in more than one direction. In FIG. 109A, the extension will retract if it encounters force, even while the user is attempting to push the extension in. In this case the positioning rod and the extension can move relative to each other. FIG. 109B shows an extension that moves to conform to anatomy or force encountered without input from the user. This extension can also be connected to a positioning rod that the user can control. FIG. 109C shows an extension which rotates depending on force encountered.

Diagnostic extensions or sections may also be steerable. For example, wires or other connections can connect a positioning rod or structure to a diagnostic extension or part of the extension or section, for example the tip. Connections can also connect a positioning rod or structure to diagnostic elements, i.e. a video chip, in the extension or other section. The user can then move a positioning rod or structure to position the extension, part of the extension or elements contained in the extension, or other diagnostic section. Sections or elements may also be steered with electromechanical means, where a remote person such as a provider can steer the device or elements or a user may use software to steer or the user may move a positioning rod or similar device which then translates that motion to electrical signals which are sent to the sections or elements of the device where microelectromechanical components move the parts.

Figure 110A:
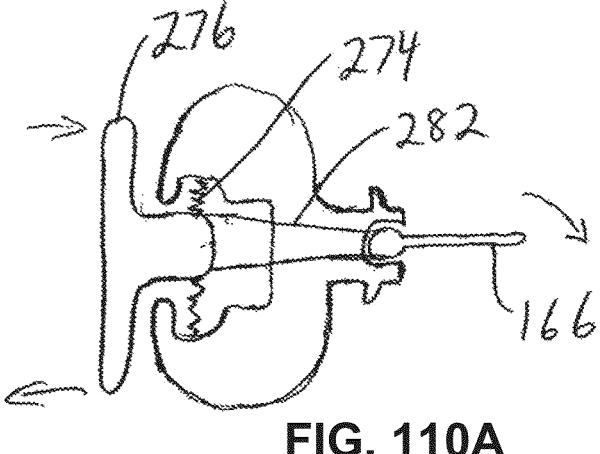
FIGS. 110A-110B show diagnostic extensions or sections which are steerable and rotatable.
Figure 110B:
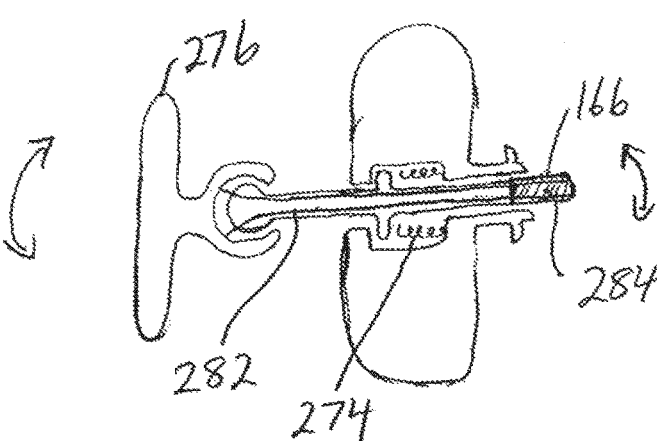

FIG. 110A shows a device which allows rotating the full length of extension. FIG. 110B shows examples of wires (for example Bowden cables) that steer or rotate the tip of an extension (show as the shaded area). This extension can also be extended by the handle. Multiple wires can be incorporated to steer the extension or a portion of the extension in several directions, for example by using two pairs of Bowden cables or other steering means. The handles in both figures can take a variety of forms and can also contain a display to view images while steering the device. Similarly, any positioning rod, for example in previously discussed figures, can contain a display. These extensions may also move or retract when encountering forces, such as when the extensions are pushed into anatomical structures such as the ear canal wall.

FIGS. 111A through 113 show devices with diagnostic extensions that can fit attachments with different lengths. FIGS. 111A-111B show an extension which can be extended to fit longer attachments. The extension may be positioned to fit an ear attachment and can be extended to fit a longer oral attachment. Various means can be used to lock or maintain the extension in place, for example friction, twisting the handle to secure a latch, a lock screw or spring positioning pins. FIG. 112 shows an extendable and retractable extension, in this case that wraps and unwraps from a wheel or coil. FIG. 113 shows a device which retracts to fit shorter attachments. The extension has a larger diameter section to prevent over-insertion into the ear canal even when the ear attachment is not connected. In general it is desired that a main device has features such as this for safety in case an attachment is not used.

Figure 114A:
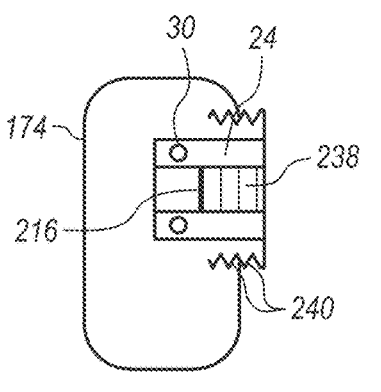
FIGS. 114A-H show a configuration of a main diagnostic device where the diagnostic elements are contained in the body of the main device and not in an extension.
Figure 114B:
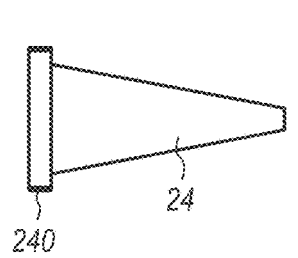
Figure 114C:
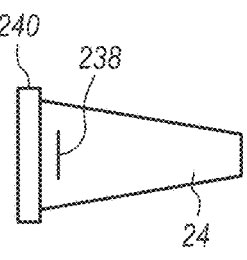
Figure 114F:
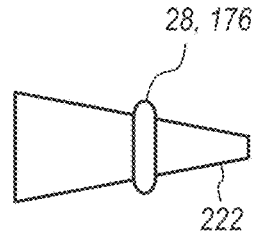
Figure 114G:
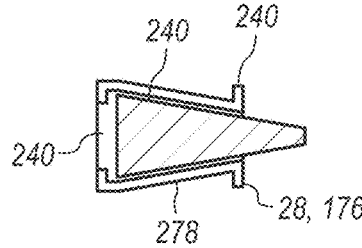
Figure 114D:
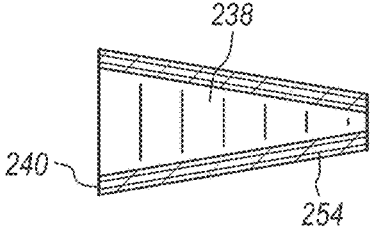
Figure 114E:
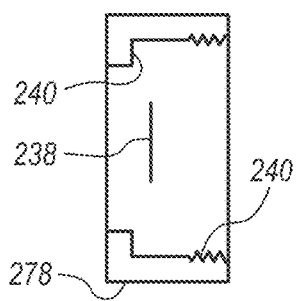
Figure 114H:
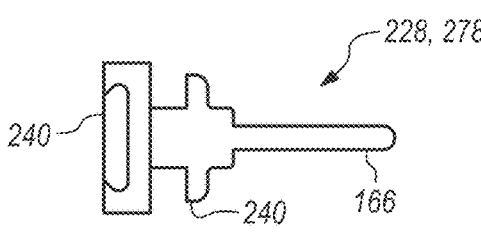

FIGS. 114A-114H show an alternative configuration of a main diagnostic device where the diagnostic elements, i.e. a video chip and LEDs, are contained in the body of the main device and not in an extension. It may be possible to incorporate a larger, higher resolution and/or less expensive video chip, as well as brighter light sources, in this case. The device can be constructed with a variety of connections, for example an internal thread and an external rim to snap or slip attachments onto. The device can connect directly to attachments for certain areas of the body, for example various extensions to image the ear as shown in FIGS. 114B, 114C, 114D. FIG. 114B shows an attachment similar to a standard speculum which can connect to the main device and which has an open channel (access element) running through it to channel light. FIGS. 114C, 114D show variations of a speculum. Attachments can have a lens or lens array in a channel and can also have optical fibers to channel light to the tip. The main device can also be configured to connect to a standard speculum. A variety of attachments can be created, for example as described earlier. Adapters can also connect to the main device which then connect to various attachments. FIG. 114E shows an adapter which has a lens and is configured to connect to standard speculums. FIG. 114F shows an attachment similar to a standard speculum that has a stop to prevent over insertion. This anatomical interface may also be configured to help align the attachment. The stop or anatomical interface may be permanently connected to the speculum (i.e. overmolded) or can be constructed to slide over a speculum. FIG. 114G shows another adapter which has an anatomical interface and stop and which can connect to a standard speculum or be configured to connect to a variety of other attachments. The adapter is open on one side to receive the speculum in from the side due to its tapered shape, rather than in form the end. Additional attachments may be connected to the adapter in addition to the speculum, for example an earbud can connect to the stop. FIG. 114H shows an attachment which is similar to part of the device in FIGS. 90A-90C. This attachment can channel light to and from the tip to the diagnostic elements in the main device, or can contain diagnostic elements and have electrical connections to the main device, or a combination of the two. Additional attachments can connect to this attachment.

FIG. 115 shows an example of a configuration with diagnostic elements in the main body of a device that allows extension and retraction.

FIGS. 116A-116B show a device with various diagnostic elements (i.e. light source, video chips, pressure sensors, infrared sensors) at different locations in a device. For example, the device may have sensors to record temperature by contact to and/or at a distance from the forehead, electrical and/or optical sensors to record other physiologic parameters such as blood pressure, heart rate and pulse oximetry. Alternatively these types of sensors may be incorporated into attachments. One or more of these or similar locations can be used and attachments configured accordingly. Various connection structures can be incorporated into the main device. Different attachments can use different diagnostic elements. For example an ear attachment uses the elements in the thin extension while a skin imaging attachment uses a larger higher resolution chip located to the side of the extension. The elements at the tip of the thin extension may be a video chip and light source or alternatively, as discussed earlier, be configured as lenses that output light from one or more light sources contained away from the tip or within the larger body of the device and gather light at the tip and transfer it to one or more video chips further away from the tip or in the body of the larger section. Multiple elements may be used at the same time. For example, a large chip with wide angle lens is used to image the body and show where a device is being placed while a video chip at a different location is used with an attachment with a zoom lens to image a specific location. The device can be structured in a variety of ways. For example, as discussed elsewhere, a device similar to an earbud, an over the ear piece or a small diameter device as shown in FIGS. 118A, 118B, and 119. The device shown in FIGS. 116A-116B may have imaging chips or other diagnostic elements in the main body.

FIGS. 117-119 show various other configurations of devices and kits.

FIG. 117 shows a small diagnostic device which fits into, snaps into, or otherwise connects to an anatomical interface for imaging the oral cavity and throat. The diagnostic device can be used to image the ear and can connect to other attachments. The device may be an ear bud size device that fits/snaps into an oral device.

FIGS. 118A-118B show another configuration of a main device and attachments. FIG. 118A shows an attachment which has a wire and connection to a main device. The attachment is a small diameter device which can be configured with a tip shape similar to a cotton swab and can be used to image the ear canal or oral cavity. Ideally, this attachment has a stop to prevent over-insertion into the ear canal, such as a flared section or larger diameter section which can be configured in many ways, such as has been described earlier for various anatomical interfaces that serve as a stop and/or to otherwise help position or stabilize the device. A video chip and light source may be located at the tip of the device, or lenses or other inputs/outputs may be located at the tip of the device and one or more video chips and light sources located further away from the tip, for example in the larger diameter section of the device. FIG. 118B shows another attachment to the main device which contains additional diagnostic elements and connections for other attachments. FIGS. 118A-118B may be components within a box containing electronics and other components with attachments for wired devices (or wireless). One example attachment may be a cotton swab style device for imaging the ear. Another example attachment may have more diagnostic elements and connections for other attachments.

FIG. 119 shows a diagnostic device that has a long narrow extension with diagnostic elements at the tip. The tip can be configured similar to a cotton swab, i.e. slightly larger rounded diameter. The main body of this device contains other elements such as a battery, video chip and electronics, for example for partial signal processing. This device can be used to image the ear, oral cavity or other body area. It can also be configured with other diagnostic elements, for example to record temperature by inserting into the ear canal or by pointing towards or contacting the forehead. It can also be configured to connect to attachments for the ear or oral cavity or other area of the body, for example to help position the device or anatomy. Ideally, the device has a stop to prevent over-insertion into the ear canal, for example a larger diameter section. The device may also fit into other attachments, similar to the device in FIG. 117, FIGS. 111A-111B, or FIGS. 102A-102C. The extension, or part of the extension can be flexible and/or elastic. For example, part of the extension can be constructed with a spring wire or coil (i.e. stainless steel or nitinol) or other elastic means that helps maintain a certain shape that can be manipulated or bent, and that then returns to the original shape. The extension can also be structured to allow its shape to be bent and formed into a desired shape which it then maintains.

The various embodiments described above can be combined to provide further embodiments. Aspects of the embodiments can be modified, if necessary to employ concepts of the various patents, application and publications to provide yet further embodiments.

Other objects, advantages and embodiments of the various aspects of the present invention will be apparent to those who are skilled in the field of the invention and are within the scope of the description and the accompanying figure. For example, but without limitation, structural or functional elements might be rearranged, or method steps reordered, consistent with the present invention. Similarly, a device may comprise a single instance of a device or comprise a plurality of devices, such plurality functioning as a single device working in tandem. For example, a computing device may consist of a plurality of computing devices which together provide the desired functionality. The device types described in various embodiments are not meant to limit the possible types of devices that may be used in embodiments of aspects of the present invention, and other types of devices that may accomplish similar tasks may be implemented as well. Similarly, principles according to the present invention, and methods and systems that embody them, could be applied to other examples, which, even if not specifically described here in detail, would nevertheless be within the scope of the present invention.

The following listing identifies elements illustrated in the Figures and provides the respective reference numeral for each of the identified elements.

REFERENCE

Numeral Element

10 Telehealth system
12 Provider
14 Caregiver
16 Subject

18 Diagnostic device
20 Communication component
22 Processing component
24 Accessing element(s)
26 Capturing element(s)
28 Anatomical interface component or feature
30 Light source
32 Speaker
34 Microphone
36 Diaphram
38 Kit
40 Oral device/attachment/component
42 Light emitting
44 Battery
160 Over ear piece
162 Ear bud
164 Ear canal engagement section to fit entrance of ear canal
166 Diagnostic extension
168 Sleeve fitting/component
170 Stop for oral device/attachment
172 Light input
174 Main diagnostic device

REFERENCE

Numeral Element

176 Stop for ear device/attachment
178 Over ear piece
180 Concha part/section
200 Provider system
202 User system
204 Accounts, logistics and infrastructure system
206 Diagnostic information data
210 Diagnostic element(s)
212 Input and/or output
214 Source element
216 Video chip
218 Wireless chip
220 Electronics
222 Ear device/attachment/component
224 Skin device/attachment/component
226 Eye device/attachment/component
228 Stethoscope device/attachment/component
230 Field of view
232 Primary input/output direction (for example, center of field of view or diagnostic view)
234 Electrical contacts
236 Electrical connection/wire
238 Lens or lens system
240 Connection/fitting
242 Leg of device/attachment/component
244 Light shield
246 Temperature sensor
248 Nose device/attachment/component
250 Eye piece
252 Access opening in eye piece
254 Optical fibers
256 Open channel
258 Display/screen
260 Handle or main body section
262 Display attachment
264 Hinge/joint
266 Rotating component/section
268 Seal/gasket
270 Elastic joint or section 272 End of receiving channel
274 Elastic member
276 Positioning structure, rod or handle
278 Adapter
280 Other attachment
282 Steering cable

REFERENCE

Numeral Element

284 Steerable section
286 Otoscope/other viewing instrument
288 Speculum
290 Tongue depressor
292 Stiffer section
294 Inflatable/expandable section
296 Flexible section

What is claimed is:

1. An imaging apparatus for obtaining images for diagnosis of a human subject's condition, the imaging apparatus comprising:
a main body;
a diagnostic extension coupled to the main body and including a tip at a distal end of the diagnostic extension, wherein a cross section area at the tip is larger than a cross section area at the proximal end of the diagnostic extension and wherein the diagnostic extension includes a coil or a wire that elastically bends when external forces are applied to the diagnostic extension and returns the diagnostic extension to an original shape when the external forces are removed;
a light source;
a digital imaging element within the tip of the diagnostic extension, the digital imaging element configured to capture diagnostic information, the diagnostic extension configured to be inserted into the ear canal; and
a first anatomical interface coupled to the main body or the diagnostic extension and shaped to engage the ear canal of the subject's ear, the engagement extending past an entrance to the ear canal.

2. The imaging apparatus according to claim 1, wherein the digital imaging element is a CMOS imaging sensor.

3. The imaging apparatus according to claim 1, wherein the first anatomical interface comprises a stop to prevent over-insertion into the ear canal.

4. The imaging apparatus according to claim 1, wherein the diagnostic extension is flexible.

5. The imaging apparatus according to claim 1, further comprising a second anatomical interface configured to contact the subject's cheek.

6. The imaging apparatus according to claim 1, further comprising a second anatomical interface that is an over ear piece.

7. The imaging apparatus according to claim 1, wherein the first anatomical interface comprises a flexible portion that conforms to the shape of the ear canal.

8. The imaging apparatus according to claim 1, wherein the anatomical interface is one of a plurality of attachments.

9. The imaging apparatus according to claim 8, wherein the diagnostic extension is coupled to the main body or the first anatomical interface via one or more elastic members or joint.

10. The imaging apparatus according to claim 1, wherein the tip has an oval shape.

11. The imaging apparatus according to claim 1, wherein the first anatomical interface defines an opening larger than the diagnostic extension through which the diagnostic extension extends, allowing the diagnostic extension to move within the opening.

12. The imaging apparatus according to claim 1, wherein the diagnostic extension is elastically coupled to the main body and configured to be extended by a user.

13. An imaging apparatus for obtaining images for diagnosis of a human subject's condition, the imaging apparatus comprising:

a main body;

a diagnostic extension coupled to the main body via one or more elastic members to float within the main body, the diagnostic extension including a coil or a wire that elastically bends when external forces are applied to the diagnostic extension and returns the diagnostic extension to an original shape when the external forces are removed, the diagnostic extension including a tip at a distal end of the diagnostic extension, wherein a cross section area at the tip is larger than a cross section area at the proximal end of the diagnostic extension;

a light source; and a digital imaging chip within the tip of the diagnostic extension, the digital imaging chip configured to capture diagnostic information, the diagnostic extension configured to be inserted into the ear canal via an anatomical interface that engages the ear canal including at locations extending past an entrance to the ear canal.

14. The imaging apparatus according to claim 1, wherein the original shape of the extension is substantially straight.

15. The imaging apparatus according to claim 1, wherein the first anatomical interface is configured as a positioning guide, encouraging a preferred position of the diagnostic extension within the canal.

\* \* \* \* \*